(12) United States Patent
Lang et al.

(10) Patent No.: US 6,515,122 B1
(45) Date of Patent: Feb. 4, 2003

(54) TETRACYCLIC BENZIMIDAZOLE DERIVATIVES AND COMBINATORIAL LIBRARIES THEREOF

(75) Inventors: Hengyuan Lang, San Diego, CA (US); Yazhong Pei, Aliso Viejo, CA (US)

(73) Assignee: Lion Bioscience AG (DE)

( * ) Notice: Subject to any disclaimer, the term of this patent is extended or adjusted under 35 U.S.C. 154(b) by 0 days.

(21) Appl. No.: 09/405,357

(22) Filed: Sep. 24, 1999

(51) Int. Cl.[7] .................. C07D 487/00; A61K 31/55; A01N 43/62

(52) U.S. Cl. ........................ 540/494; 514/219

(58) Field of Search ................... 540/494, 555, 540/543; 514/219

(56) References Cited

U.S. PATENT DOCUMENTS

| | | | |
|---|---|---|---|
| 3,642,778 A | * 2/1972 | Helsley et al. | 540/494 |
| 5,288,514 A | 2/1994 | Ellman | 427/2 |
| 5,324,483 A | 6/1994 | Cody et al. | 422/131 |
| 5,506,337 A | 4/1996 | Summerton et al. | 528/391 |
| 5,549,974 A | 8/1996 | Holmes | 428/403 |

OTHER PUBLICATIONS

Ducan et al., J. Heterocyclic Chem., vol. 10, pp. 65–70, 1973.*

Duncan et al., "Synthesis of Indolo– and Benzimidazoquinazolines and Benzodiazepines," *J. Heterocycl. Chem.* 10:65–70 (1973).

Cherkaoui et al., "Triazolobenzoldiazepine Derivative (III): Synthesis of s–Triazolo–[4,3–α]–Benzimidazolo–[1,2–d] [1,4]–Benzodiazepines," *Synth. Commun.* 25:3287–3292 (1995).

Cherkaoui et al., "New s–Triazolobenzodiazepine Derivative (III): Synthesis of s–Triazolo–[4,3–α]Benzimidazolo–[1,2–d] [1,4]Benzodiapines" *Synth. Commun.* 25:1027–1033 (1995).

Goff et al., "Solid–Phase Synthesis of Highly Substituted Peptoid 1(2H)—Isoquinolinones," *J. Org. Chem.* 60:5748–5749 (1995).

Huang et al., "A New "Traceless" Solid–phase Synthesis Strategy: Synthesis of a Benzimidazole Library," *Tetr. Ltrs.* 40:2665–2668 (1999).

Mayer et al., "Solid–Phase Synthesis of Benzimidazoles," *Tetr. Ltrs.* 39:6655–6658 (1998).

Phillips and Wei, "Solid Phase Synthesis of Benzimidazoles," *Tetr. Ltrs.* 37:4887–4890 (1998).

(List continued on next page.)

*Primary Examiner*—Joseph K. McKane
*Assistant Examiner*—Grace Hsu
(74) *Attorney, Agent, or Firm*—Law Office of David Spolter

(57) ABSTRACT

The present invention relates to novel tetracyclic benzimidazole derivative compounds of the following formula:

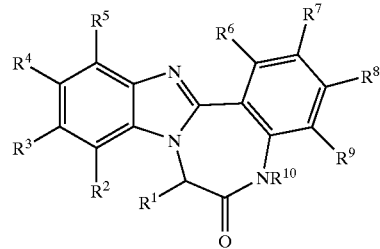

wherein $R^1$ to $R^{10}$ have the meanings described in here.

The invention further relates to combinatorial libraries containing two or more such compounds, as well as methods of preparing tetracyclic benzimidazole derivative compounds.

16 Claims, 1 Drawing Sheet

Reaction Scheme of Tetracyclic Benzimidazole Library

OTHER PUBLICATIONS

Sun and Yan, "Single Bead IR Monitoring of A Novel Benzimidazole Synthesis," *Bioorg. & Med. Chem. Ltrs.* 8:361–364 (1998).

Tumelty et al., "Solid–Phase Synthesis of Substituted Benzimidazoles," *Tetr. Ltrs.* 40:6185–6188 (1999).

Wilson et al., "Solid–supported syntheses of 3–thio–1,2, 4–triazoles," *Molecular Diversity* 3:95–112 (1998).

Yeh and Sun, "Rapid Parallel Synthesis of Benzimidazoles," *Synlett* 6:810–812 (1999).

* cited by examiner

TETRACYCLIC BENZIMIDAZOLE DERIVATIVES AND COMBINATORIAL LIBRARIES THEREOF

BACKGROUND OF THE INVENTION

1. Field of the Invention

The present invention relates generally to the synthesis of compounds comprising heterocyclic rings. In one specific embodiment, the invention provides novel tetracyclic benzimidazole derivative compounds as well as novel combinatorial libraries comprised of such compounds.

2. Background Information

The process of discovering new therapeutically active compounds for a given indication involves the screening of all compounds from available compound collections. From the compounds tested, one or more structures is selected as a promising lead. A large number of related analogs are then synthesized in order to develop a structure-activity relationship and select one or more optimal compounds. With traditional "one-at-a-time" synthesis and biological testing of analogs, this optimization process is long and labor intensive. Adding significant numbers of new structures to the compound collections used in the initial screening step of the discovery and optimization process cannot be accomplished with traditional "one-at-a-time" synthesis methods, except over a time frame of years or even decades. Faster methods are needed that allow for the preparation of up to thousands of related compounds in a matter of days or a few weeks. This need is particularly evident when it comes to synthesizing more complex compounds, such as tetracyclic benzimidazole derivative compounds.

Combinatorial approaches have recently been extended to "organic," or non-peptide, libraries. For example, Zambias et al. (U.S. Pat. No. 5,712,171) describe a method of generating libraries that contain aminimides, oxazolones, sulfonylaminides and phosphonylaminides as the core structure in spatially arranged arrays. Combinatorial chemical methods have been applied to a limited number of heterocyclic compounds, as described, for example, in Wilson et al., *Molecular Diversity*, 3:95–112 (1998); U.S. Pat. Nos. 5,288,514; 5,324,483; and Goff et al., *J. Org. Chem.*, 60:5748–5749 (1995). See also U.S. Pat. Nos. 5,549,974 and 5,506,337. Combinatorial chemical methods have even been extended to benzimidazole compounds, as described, for example, in Tumelty et al., *Tetr. Ltrs.*, 40:6185–6188 (1999); Yeh et al., *Synlett*, 6:810–812 (1999); Sun et al., *Bioorg. & Med. Chem. Ltrs.*, 8:361–364 (1998); Huang et al., *Tetr. Ltrs.*, 40:2665–2668 (1999); Phillips and Wei, *Tetr. Ltrs.*, 37:4887–4890 (1996); and Mayer et al., *Tetr. Ltrs.*, 39:6655–6658 (1998). However, the heterocyclic libraries to date contain compounds of limited diversity and complexity.

Substituent limitations have been overcome for mixtures of peptides and peptidomimetics through the use of solid phase techniques versus solution-phase. An important step in the development of solid-phase techniques was the discovery of methods to prepare large numbers of individual compounds simultaneously, as described, for example, by Houghten in U.S. Pat. No. 4,631,211. These solid phase methods, however, have rarely been applied to the syntheses of complex heterocyclic structures. Therefore a need exists to develop more complex "organic" libraries based on heterocyclic medicinal compounds which would need less time and effort in the synthesis and testing required to bring an organic pharmaceutical product to fruition. In short, improved methods for generating therapeutically useful heterocyclic compounds, such as tetracyclic benzimidazole derivatives, are desired.

Tetracyclic benzimidazole derivative compounds have been the subject of investigation in a number of different biological areas. For example, tetracyclic benzimidazole derivatives have been proposed as useful as antidepressants (DE 2051962 (1971)). Tetracyclic benzimidazole derivatives have also been the subject of serial chemical synthesis. See, for example, DE 2051962 (1971); Herkaoui et al., *Synth. Commun.*, 25:3287–92 (1995); Herkaoui et al., *Synth. Commun.*, 25:1027–33 (1995); and Duncan et al., *J. Heterocycl. Chem.*, 10:65–70 (1973). However, more complex benzimidazole derivatives, especially those that are tetracyclic and, more especially, those that have a substituent other than hydrogen have been difficult to attain.

This invention satisfies this need and provides related advantages as well. The present invention overcomes the known limitations to classical serial organic synthesis of tetracyclic benzimidazole derivatives, for example, as well as the shortcomings of combinatorial chemistry related to tetracyclic benzimidazole derivatives. The present invention allows for rapid generation of large diverse libraries of complex tetracyclic benzimidazole derivatives as discrete molecules. The present invention can utilize a readily available pool of building blocks that can be incorporated into the various regions of the molecule. Furthermore, the method of making the present invention allows for the use of building blocks that contain a wide range of diverse functionality. Such building blocks can provide combinatorial libraries that consist of large numbers as well as combinatorial libraries that are extremely diverse with respect to the functionality contained within those libraries. The present invention combines the techniques of solid-phase synthesis of tetracyclic benzimidazole derivatives and the general techniques of synthesis of combinatorial libraries to prepare highly diverse new tetracyclic benzimidazole derivative compounds.

SUMMARY OF THE INVENTION

The present invention relates to novel tetracyclic benzimidazole derivative compounds of the following formula:

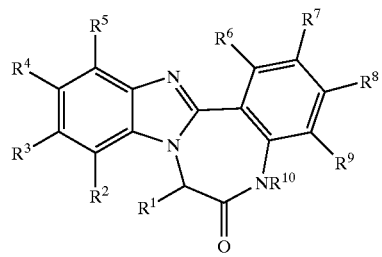

wherein $R^1$ to $R^{10}$ have the meanings provided below.

The invention further relates to combinatorial libraries containing two or more such compounds, and to methods of generating tetracyclic benzimidazole derivative compounds.

BRIEF DESCRIPTION OF THE DRAWING

FIG. 1 shows the reaction scheme for the combinatorial synthesis of tetracyclic benzimidazole derivative compounds.

DETAILED DESCRIPTION OF THE INVENTION

Figure 1:
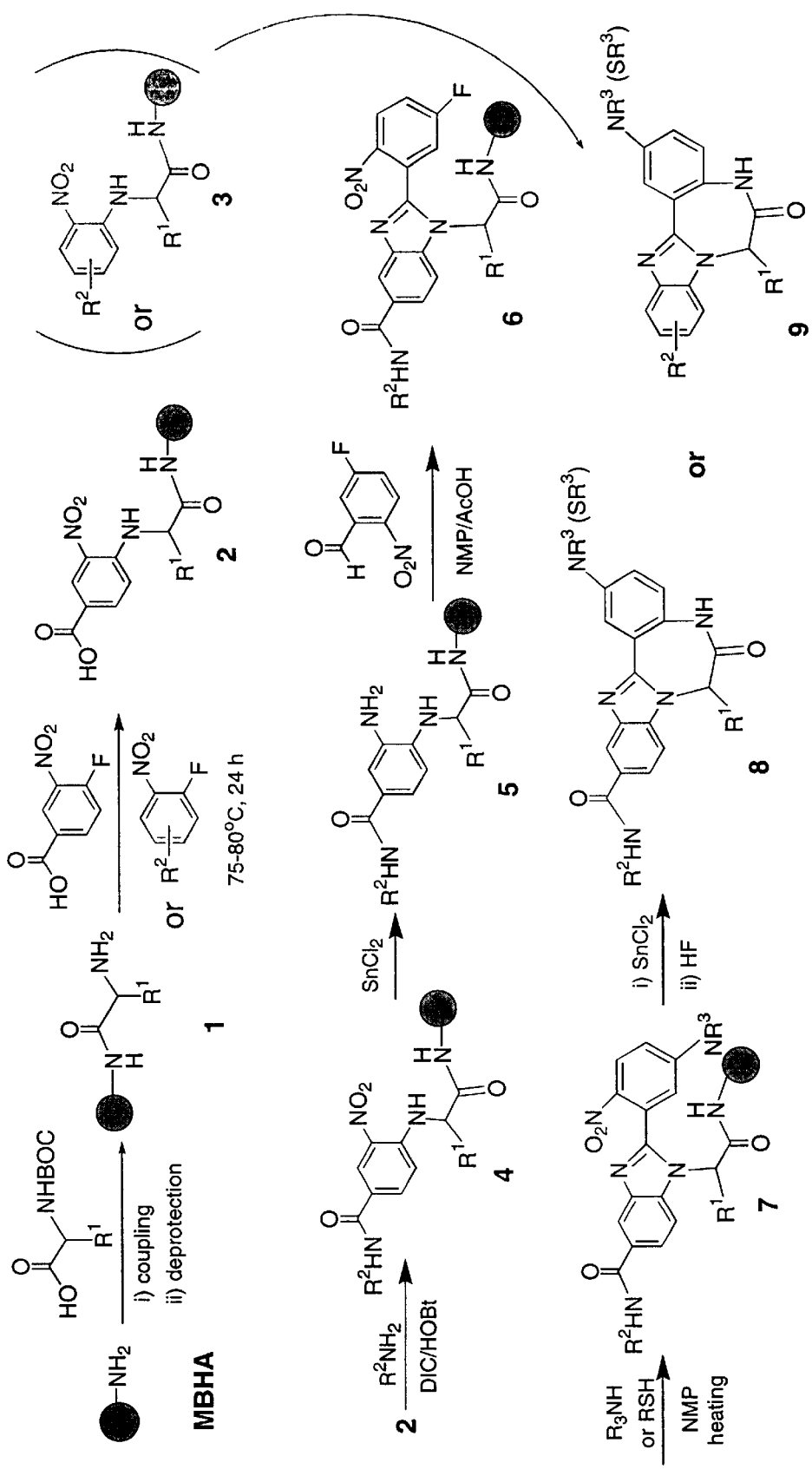
In FIG. 1, described below, as well as the examples, $R^1$ corresponds to $R^1$ of the claimed invention; $R^2$ corresponds to $R^2$ to $R^5$ of the claimed invention; —C(O)NHR$^2$ corresponds to $R^4$ of the claimed invention (which can be —C(O)NR$^{11}$R$^{12}$); and —NHR$^3$ and —SR$^3$ correspond to $R^7$ of the claimed invention (which can be —NR$^{11}$R$^{12}$ or —SR$^{11}$)

The present invention provides compounds and combinatorial libraries of compounds of the formula:

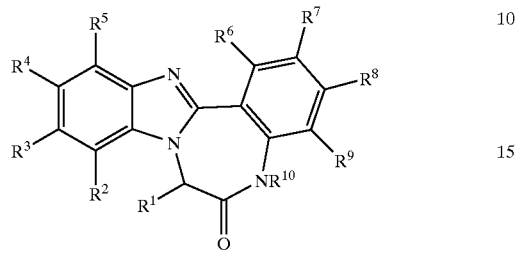

wherein:

R[1] is a hydrogen atom, $C_1$ to $C_{12}$ alkyl, $C_1$ to $C_{12}$ substituted alkyl, phenyl, substituted phenyl, $C_7$ to $C_{18}$ phenylalkyl, $C_7$ to $C_{18}$ substituted phenylalkyl, $C_1$ to $C_{12}$ heterocycloalkyl, $C_1$ to $C_{12}$ substituted heterocycloalkyl, heteroaryl, substituted heteroaryl, cyano, $C_1$ to $C_{12}$ acyl, $C_1$ to $C_{12}$ substituted acyl, $C_1$ to $C_{12}$ alkoxycarbonyl, $C_1$ to $C_{12}$ substituted alkoxycarbonyl, $C_1$ to $C_{12}$ alkylaminocarbonyl, $C_1$ to $C_{12}$ substituted alkylaminocarbonyl, phenylaminocarbonyl, substituted phenylaminocarbonyl, $C_1$ to $C_{10}$ alkylthio, $C_1$ to $C_{10}$ substituted alkylthio, $C_1$ to $C_{10}$ alkylsulfonyl, $C_1$ to $C_{10}$ substituted alkylsulfonyl, $C_1$ to $C_{10}$ alkylsulfoxide, $C_1$ to $C_{10}$ substituted alkylsulfoxide, phenylthio, substituted phenylthio, phenylsulfoxide, substituted phenylsulfoxide, phenylsulfonyl, substituted phenylsulfonyl, heterocycle, substituted heterocycle, cyclic $C_2$ to $C_7$ alkylene, substituted cyclic $C_2$ to $C_7$ alkylene, cyclic $C_2$ to $C_7$ heteroalkylene, substituted cyclic $C_2$ to $C_7$ heteroalkylene, naphthyl, substituted naphthyl, $C_5$ to $C_7$ cycloalkyl, $C_5$ to $C_7$ substituted cycloalkyl, $C_5$ to $C_7$ cycloalkenyl or $C_5$ to $C_7$ substituted cycloalkenyl;

R[2], R[3], R[4], R[5], R[6], R[7], R[8] and R[9] are, independently, a hydrogen atom, halo, hydroxy, protected hydroxy, cyano, $C_1$ to $C_{12}$ alkyl, $C_2$ to $C_{12}$ alkenyl, $C_2$ to $C_{12}$ alkynyl, $C_1$ to $C_{12}$ substituted alkyl, $C_2$ to $C_{12}$ substituted alkenyl, $C_2$ to $C_{12}$ substituted alkynyl, $C_1$ to $C_{12}$ alkoxy, $C_1$ to $C_{12}$ substituted alkoxy, $C_1$ to $C_{12}$ acyloxy, $C_1$ to $C_{12}$ acyl, $C_3$ to $C_7$ cycloalkyl, $C_3$ to $C_7$ substituted cycloalkyl, $C_5$ to $C_7$ cycloalkenyl, $C_5$ to $C_7$ substituted cycloalkenyl, heterocyclic ring, substituted heterocyclic ring, $C_7$ to $C_{18}$ phenylalkyl, $C_7$ to $C_{18}$ substituted phenylalkyl, $C_1$ to $C_{12}$ heterocycloalkyl, $C_1$ to $C_{12}$ substituted heterocycloalkyl, phenyl, substituted phenyl, naphthyl, substituted naphthyl, cyclic $C_2$ to $C_7$ alkylene, substituted cyclic $C_2$ to $C_7$ alkylene, Cyclic $C_2$ to $C_7$ heteroalkylene, substituted cyclic $C_2$ to $C_7$ heteroalkylene, carboxy, protected carboxy, hydroxymethyl, protected hydroxymethyl, amino, protected amino, (monosubstituted)amino, protected (monosubstituted)amino, (disubstituted)amino, $C_1$ to $C_{10}$ alkylamino, $C_1$ to $C_{10}$ alkyl protected amino, $C_1$ to $C_{10}$ alkyl (monosubstituted)amino, $C_1$ to $C_{10}$ alkyl, protected (monosubstituted)amino, $C_1$ to $C_{10}$ alkyl (disubstituted)amino, $C_1$ to $C_{10}$ substituted alkylamino, $C_1$ to $C_{10}$ substituted alkyl protected amino, $C_1$ to $C_{10}$ substituted alkyl (monosubstituted)amino, $C_1$ to $C_{10}$ substituted alkyl protected (monosubstituted)amino, $C_1$ to $C_{10}$ substituted alkyl(disubstituted)amino, carboxamide, protected carboxamide, $C_1$ to $C_{10}$ alkylthio, $C_1$ to $C_{10}$ substituted alkylthio, $C_1$ to $C_{10}$ alkylsulfonyl, $C_1$ to $C_{10}$ substituted alkylsulfonyl, $C_1$ to $C_{10}$ alkylsulfoxide, $C_1$ to $C_{10}$ substituted alkylsulfoxide, phenylthio, substituted phenylthio, phenylsulfoxide, substituted phenylsulfoxide, phenylsulfonyl, substituted phenylsulfonyl or (i) the formula —$C(O)NR^{11}R^{12}$, (ii) the formula —$C(O)R^{11}$, (iii) the formula —$NR^{11}R^{12}$, (iv) the formula —$SR^{11}$, (v) the formula —$OR^{11}$ or (vi) the formula —$C(O)OR^{11}$, wherein $R^{11}$ and $R^{12}$ are, independently, a hydrogen atom, $C_1$ to $C_{12}$ alkyl, $C_1$ to $C_{12}$ substituted alkyl, $C_2$ to $C_{12}$ alkenyl, $C_2$ to $C_{12}$ substituted alkenyl, phenyl, substituted phenyl, naphthyl, substituted naphthyl, $C_7$ to $C_{18}$ phenylalkyl, $C_7$ to $C_{18}$ substituted phenylalkyl, $C_1$ to $C_{12}$ heterocycloalkyl, $C_1$ to $C_{12}$ substituted heterocycloalkyl, heteroaryl, substituted heteroaryl, heterocycle, substituted heterocycle, $C_1$ to $C_{12}$ acyl, $C_1$ to $C_{12}$ substituted acyl, phenylsulfonyl, substituted phenylsulfonyl, $C_1$ to $C_{10}$ alkylsulfonyl, $C_1$ to $C_{10}$ substituted alkylsulfonyl, $C_1$ to $C_{12}$ alkylaminocarbonyl, $C_1$ to $C_{12}$ substituted alkylaminocarbonyl, phenylaminocarbonyl or substituted phenylaminocarbonyl; and R[10] is a hydrogen atom, $C_1$ to $C_{12}$ alkyl, $C_1$ to $C_{12}$ substituted alkyl, $C_2$ to $C_{12}$ alkenyl, $C_2$ to $C_{12}$ substituted alkenyl, $C_7$ to $C_{18}$ phenylalkyl, $C_7$ to $C_{18}$ substituted phenylalkyl, $C_1$ to $C_{12}$ heterocycloalkyl or $C_1$ to $C_{12}$ substituted heterocycloalkyl; or a pharmaceutically acceptable salt of a compound thereof.

In an additional embodiment,

R[1] is a hydrogen atom, $C_1$ to $C_{12}$ alkyl, $C_1$ to $C_{12}$ substituted alkyl, phenyl, substituted phenyl, $C_7$ to $C_{18}$ phenylalkyl, $C_7$ to $C_{18}$ substituted phenylalkyl, $C_1$ to $C_{12}$ heterocycloalkyl, $C_1$ to $C_{12}$ substituted heterocycloalkyl, heteroaryl, substituted heteroaryl, $C_1$ to $C_{10}$ alkylthio, $C_1$ to $C_{10}$ substituted alkylthio, heterocycle or substituted heterocycle.

In a further embodiment,

R[2], R[3], R[4] and R[5] are, independently, a hydrogen atom, halo, hydroxy, protected hydroxy, cyano, $C_1$ to $C_{12}$ alkyl, $C_1$ to $C_{12}$ substituted alkyl, $C_1$ to $C_{12}$ alkoxy, $C_1$ to $C_{12}$ substituted alkoxy, carboxy, protected carboxy, $C_1$ to $C_{10}$ alkylthio, $C_1$ to $C_{10}$ substituted alkylthio, the formula —$C(O)NR^{11}R^{12}$ or the formula —$C(O)R^{11}$, wherein $R^{11}$ and $R^{12}$ join the nitrogen atom depicted in the above formula to form a heterocycle or substituted heterocycle or $R^{11}$ and $R^{12}$ are, independently, a hydrogen atom, $C_1$ to $C_{12}$ alkyl, $C_1$ to $C_{12}$ substituted alkyl, phenyl, substituted phenyl, $C_7$ to $C_{18}$ phenylalkyl, $C_7$ to $C_{18}$ substituted phenylalkyl, $C_1$ to $C_{12}$ heterocycloalkyl, $C_1$ to $C_{12}$ substituted heterocycloalkyl, heteroaryl, substituted heteroaryl, heterocycle or substituted heterocycle.

In another embodiment,

R[2], R[3], and R[5] are each a hydrogen atom, and R[4] is the formula —$C(O)NR^{11}R^{12}$ or the formula —$C(O)R^{11}$, wherein $R^{11}$ and $R^{12}$ join the nitrogen atom depicted in the above formula to form a heterocycle or substituted heterocycle or $R^{11}$ and $R^{12}$ are, independently, a hydrogen atom, $C_1$ to $C_{12}$ alkyl, $C_1$ to $C_{12}$ substituted alkyl, phenyl, substituted phenyl, $C_7$ to $C_{18}$ phenylalkyl, $C_7$ to $C_{18}$ substituted phenylalkyl, $C_1$ to $C_{12}$ heterocycloalkyl, $C_1$ to $C_{12}$ substituted heterocycloalkyl, heteroaryl, substituted heteroaryl, heterocycle or substituted heterocycle.

In a further embodiment, $R^6$, $R^7$, $R^8$ and $R^9$ are, independently, a hydrogen atom, halo, heterocycle, substituted heterocycle the formula —$NR^{11}R^{12}$ or the formula —$SR^{11}$, wherein $R^{11}$ and $R^{12}$ are, independently, a hydrogen atom, $C_1$ to $C_{12}$ alkyl, $C_1$ to $C_{12}$ substituted alkyl, $C_2$ to $C_{12}$ alkenyl, $C_2$ to $C_{12}$ substituted alkenyl, $C_7$ to $C_{18}$ phenylalkyl, $C_7$ to $C_{18}$ substituted phenylalkyl, $C_1$ to $C_{12}$ heterocycloalkyl, $C_1$ to $C_{12}$ substituted heterocycloalkyl, heteroaryl, substituted heteroaryl, heterocycle or substituted heterocycle.

In an additional embodiment, $R^6$, $R^8$ and $R^9$ are each a hydrogen atom, and $R^7$ is halo, heterocycle, substituted heterocycle, the formula —$NR^{11}R^{12}$ or the formula —$SR^{11}$, wherein $R^{11}$ and $R^{12}$ are, independently, a hydrogen atom, $C_1$ to $C_{12}$ alkyl, $C_1$ to $C_{12}$ substituted alkyl, $C_2$ to $C_{12}$ alkenyl, $C_2$ to $C_{12}$ substituted alkenyl, $C_7$ to $C_{18}$ phenylalkyl, $C_7$ to $C_{18}$ substituted phenylalkyl, $C_1$ to $C_{12}$ heterocycloalkyl, $C_1$ to $C_{12}$ substituted heterocycloalkyl, heteroaryl, substituted heteroaryl, heterocycle or substituted heterocycle.

In another embodiment, $R^{10}$ is a hydrogen atom.

Another embodiment provides that $R^1$ is a hydrogen atom, methyl, 2-propyl, 2-butyl, aminocarbonylethyl, 2-methylmercaptoethyl, phenyl, benzyl, cyclohexylmethyl, 4-methoxybenzyl, 4-chlorobenzyl, 3-indolylmethyl, 4-(trifluoroacetyl)aminobutyl or 3-guanidinopropyl;

$R^2$, $R^3$, $R^5$, $R^6$, $R^8$, $R^9$ and $R^{10}$ are each a hydrogen atom;

$R^4$ is the formula —$C(O)NR^{11}R^{12}$, wherein $R^{11}$ and $R^{12}$ join the nitrogen atom in the depicted formula to form one of the following substitients: 1-pyrrolidino, 4-methyl-1-homopiperazino, 4-(4-fluorophenyl)-1-piperazino, 4-(2-hydroxyethoxyethyl)-1-piperazino, 4-(2-pyridyl)-1-piperazino, 4-hydroxy-1-piperidino, 4-amino-2,2,6,6-tetramethyl-1-piperidino, 3-ethoxycarbonyl-1-piperidino, 4-(4-methoxyphenyl)-3-methyl-1-piperazino, 4-aminocarbonyl-1-piperidino, heptamethyleneimino, 4-(2-furoyl)-1-piperazino, 4-(3-trifluoromethylphenyl)-1-piperazino, 3-acetamido-1-pyrrolidino, 4-ethoxycarbonyl-1-piperazino, 4-ethoxycarbonyl-1-piperidino or 4-thiomorpholino, or $R^{11}$ and $R^{12}$ are, independently, a hydrogen atom, (1-ethyl-2-pyrrolidinyl)methyl, 2-thiazolyl, 5-methoxycarbonylpentyl, 2-ethoxycarbonylethyl, 3-(methylthio)phenyl, N-methyl-(1-methyl-4-piperidino), 2-(pyridin-2-yl)ethyl, 2-hydroxyethyl, 4-(trifluoromethyl)benzyl, N,N-dimethylaminoethyl, 3-(2-oxo-1-pyrrolidino)propyl, 1-ethoxycarbonyl-4-piperidino, pyridin-2-ylmethyl, bis(2-methoxyethyl), 2-acetylaminoethyl, 3-(methylthio)propyl, 2-(1-morpholino)ethyl, 5-indazolyl, cyclopropyl, N-ethyl-(pyridin-4-ylmethyl), cycloheptyl, cyclohexyl, pyridin-3-ylmethyl, 4-(trifluoromethyl)benzyl, 2-(thien-2-yl)ethyl, 3-(N-pyrrolidino)propyl or 3-(1-imidazolyl)propyl;

$R^7$ is cyclopropylamino, 2-(1-morpholino)ethylamino, piperazino, 2-methyl-4-(3-methylphenyl)-1-piperazino, 4-aminocarbonylpiperidino, 2-(pyridin-2-yl)ethylamino, 2-(N,N-dimethylamino)ethylamino, 3-(aminomethyl)benzylamino, (5-phenyl-1H-1,2,4-triazol-3-yl)thio, 3-(4-morpholino)propylamino, tetrahydrofurfurylamino, 4-(2,5-dimethylphenyl)-1-piperazino, hexamethyleneimino, N-methyl-2-(pyridin-2-yl)ethylamino, 2-(dimethylamino)ethylamino, 4-(aminomethyl)benzylamino, (3-carboxypyridin-6-yl)thio, 2-acetylaminoethylamino, 2-(ethoxycarbonyl)ethylamino, 4-(2,3-dimethylphenyl)-1-piperazino, 4-(2-pyridyl)-1-piperazino, 3-(2-pipecolino)propylamino, 2-aminoethylamino, cyclohexylamino, imidazol-2-ylthio, 4-ethoxycarbonyl-1-piperazino, 3-methylthiopropylamino, 4-(4-fluorophenyl)piperazino, 1-benzyl-3-pyrrolidinoamino, N-methyl-4-piperidylamino, 3-aminopropylamino, N-benzylmethylamino, (3,5-dimethyl-2,6-pyrimidin-2-yl)thio, 4-acetyl-1-piperazino, 2,3-dimethoxybenzylamino, 4-(3,4-dichlorophenyl)-1-piperazino, 3-ethoxycarbonyl-1-piperidino, pyridin-3-ylmethylamino, N-methyl-2-(diethylamino)ethylamino, N-methylphenethylamino, (5-methyl-1,3,4-thiadiazol-2-yl)thio, 8-amino-3,6-dioxaoctyamino, 3-acetamido-1-pyrrolidino, 4-benzyl-1-piperazino, 4-ethoxycarbonyl-1-piperazino, 2-piperadinoethylamino, 3-dimethylaminopropylamino, cycloheptylamino, (1H-1,2,4-triazol-3-yl)thio, 4-ethoxycarbonylmethyl-1-piperazino, 4-(diethylamino)-2-butenylamino, 4-(4-nitrophenyl)-1-piperazino, 1-ethoxycarbonyl-4-piperidylamino, 1-benzyl-4-piperidylamino, N-methyl-3-(dimethylamino)propylamino, 4-(trifluoromethyl)benzylamino, (4-methyl-1,2,4-triazol-3-yl)thio, 2-ethoxyethylamino, tyramino, 4-(3-trifluoromethylphenyl)-1-piperazino, 1,3,3-trimethyl-6-aza-6-bicyclo(3,2,1)octyl, 3,3'-bis(dimethylamino)dipropylamino, butylamino, 3-(trifluoromethyl)benzylamino, pyridin-2-ylthio, 4-(2-furoyl)-1-piperazino, cyclooctylamino, 4-(4-acetylphenyl)-1-piperazino, 4-(4-methylphenyl)-3-methyl-1-piperazino, 2-fluorophenethylamino, 3-fluorophenethylamino, 4-fluorobenzylamino, fluoro, morpholino, thiomorpholino, 4-(5-chloro-2-methylphenyl)-1-piperazino, (1-ethyl-2-pyrrolidino)methylamino, 2,2,6,6-tetramethyl-4-piperidylamino, diethylamino or 3,3,5-trimethylcyclohexyamino.

In a further embodiment, $R^1$ is a hydrogen atom, methyl, 2-propyl, 2-butyl, aminocarbonylethyl, 2-methylmercaptoethyl, phenyl, benzyl, cyclohexylmethyl, 4-methoxybenzyl, 4-chlorobenzyl, 3-indolylmethyl, 4-(trifluoroacetyl)aminobutyl or 3-guanidinopropyl;

$R^2$, $R^3$, $R^4$ and $R^5$ are, independently, a hydrogen atom, methyl, carboxy, bromo, fluoro, chloro or trifluoromethyl;

$R^6$, $R^8$, $R^9$ and $R^{10}$ are each a hydrogen atom; and $R^7$is cyclopropylamino, 2-(1-morpholino)ethylamino, piperazino, 2-methyl-4-(3-methylphenyl)-1-piperazino, 4-aminocarbonylpiperidino, 2-(pyridin-2-yl)ethylamino, 2-(N,N-dimethylamino)ethylamino, 3-(aminomethyl)benzylamino, (5-phenyl-1H-1,2,4-triazol-3-yl)thio, 3-(4-morpholino)propylamino, tetrahydrofurfurylamino, 4-(2,5-dimethylphenyl)-1-piperazino, hexamethyleneimino, N-methyl-2-(pyridin-2-yl)ethylamino, 2-(dimethylamino)ethylamino, 4-(aminomethyl)benzylamino, (3-carboxypyridin-6-yl)thio, 2-acetylaminoethylamino, 2-(ethoxycarbonyl)ethylamino, 4-(2,3-dimethylphenyl)-1-piperazino, 4-(2-pyridyl)-1-piperazino, 3-(2-pipecolino)

propylamino, 2-aminoethylamino, cyclohexylamino, imidazol-2-ylthio, 4-ethoxycarbonyl-1-piperazino, 3-methylthiopropylamino, 4-(4-fluorophenyl) piperazino, 1-benzyl-3-pyrrolidinoamino, N-methyl-4-piperidylamino, 3-aminopropylamino, N-benzylmethylamino, (3,5-dimethyl-2,6-pyrimidin-2-yl)thio, 4-acetyl-1-piperazino, 2,3-dimethoxybenzylamino, 4-(3,4-dichlorophenyl)-1-piperazino, 3-ethoxycarbonyl-1-piperidino, pyridin-3-ylmethylamino, N-methyl-2-(diethylamino) ethylamino, N-methylphenethylamino, (5-methyl-1,3,4-thiadiazol-2-yl)thio, 8-amino-3,6-dioxaoctyamino, 3-acetamido-1-pyrrolidino, 4-benzyl-1-piperazino, 4-ethoxycarbonyl-1-piperazino, 2-piperadinoethylamino, 3-dimethylaminopropylamino, cycloheptylamino, (1H-1,2,4-triazol-3-yl)thio, 4-ethoxycarbonylmethyl-1-piperazino, 4-(diethylamino)-2-butenylamino, 4-(4-nitrophenyl)-1-piperazino, 1-ethoxycarbonyl-4-piperidylamino, 1-benzyl-4-piperidylamino, N-methyl-3-(dimethylamino)propylamino, 4-(trifluoromethyl) benzylamino, (4-methyl-1,2,4-triazol-3-yl)thio, 2-ethoxyethylamino, tyramino, 4-(3-trifluoromethylphenyl)-1-piperazino, 1,3,3-trimethyl-6-aza-6-bicyclo(3,2,1)octyl, 3,3'-bis(dimethylamino) dipropylamino, butylamino, 3-(trifluoromethyl) benzylamino, pyridin-2-ylthio, 4-(2-furoyl)-1-piperazino, cyclooctylamino, 4-(4-acetylphenyl)-1-piperazino, 4-(4-methylphenyl)-3-methyl-1-piperazino, 2-fluorophenethylamino, 3-fluorophenethylamino, 4-fluorobenzylamino, fluoro, morpholino, thiomorpholino, 4-(5-chloro-2-methylphenyl)-1-piperazino, (1-ethyl-2-pyrrolidino) methylamino, 2,2,6,6-tetramethyl-4-piperidylamino, diethylamino or 3,3,5-trimethylcyclohexyamino.

In any of the above embodiments, $R^7$ can be present, i.e., not hydrogen. Additionally, in any of the above embodiments, $R^4$ can be present, i.e., not hydrogen.

The invention also provides methods for making tetracyclic benzimidazole derivative compounds and libraries. In one method of the invention, tetracyclic benzimidazole derivative compounds can be prepared by:

(a) coupling a first compound having a substituent of the formula —NH—C(O)—C(variable group)—NH$_2$ with a phenyl compound that is substituted with a nitro group and a halo group in an ortho relationship on the phenyl ring, the phenyl compound further optionally substituted with a variable group at one of the remaining 4 positions of the phenyl ring, resulting in a phenyl compound substituted with a nitro group and a monosubstituted amino group;

(b) reducing the nitro group of the phenyl compound resulting from step (a);

(c) coupling the compound resulting from step (b) with a phenyl compound that is substituted with an aldehyde group and a nitro group in a meta relationship on the phenyl ring, the phenyl ring also being optionally substituted with one or more leaving groups at one of the remaining 4 positions of the phenyl ring, resulting in a phenyl substituted benzimidazole derivative compound having a nitro substituted phenyl substituent; and (d) reducing the nitro group of the benzimidazole derivative compound resulting from step (c) to form a five carbon two nitrogen seven-member ring, resulting in a tetracyclic benzimidazole compound.

In another method of the invention, the first compound having a substituent of the formula —NH—C(O)—C (variable group)—NH$_2$ is attached to solid support.

In a further method of the invention, the variable group on the phenyl group in step (a) is a carboxyl.

Another method of the invention provides that the carboxyl group of the phenyl compound resulting from step (a) is coupled with a monosubstituted amine compound, a disubstituted amine compound, a cyclic imino compound or an alcohol, resulting, respectively, in (i) a monosubstituted carboxamido substituent attached to the phenyl compound; (ii) a disubstituted substituent carboxamido attached to the phenyl compound; (iii) a cyclic imino carbonyl substituent attached to the phenyl compound; or (iv) an ester substituent attached to the phenyl compound.

In a further method of the invention, the leaving group of the phenyl substituted benzimidazole derivative compound resulting from step (c) is displaced with a (i) a monosubstituted amine; (ii) a disubstituted amine; (iii) a monosubstituted thiol; (iii) a cyclic imine; (iv) a cyclic thiol; or (v) an alcohol, resulting, respectivley, in a monosubstituted amino, disubstituted amino, cyclic imino, cyclic thio, monosubstituted thio or ether moiety on the phenyl ring.

When the above-described compounds include one or more chiral centers, the stereochemistry of such chiral centers can independently be in the R or S configuration, or a mixture of the two. The chiral centers can be further designated as R or S or R,S or d,D, l,L or d,l, D,L.

Regarding the compounds and combinatorial libraries described herein, the suffix "ene" added to any of the described terms means that two parts of the substituent are each connected to two other parts in the compound (unless the substituent contains only one carbon, in which case such carbon is connected to two other parts in the compound, for example, methylene).

The term "$C_1$ to $C_{12}$ alkyl" denotes such radicals as methyl, ethyl, n-propyl, isopropyl, n-butyl, iso-butyl, sec-butyl, tert-butyl, amyl, tert-amyl, hexyl, heptyl, octyl, nonyl, decyl, undecyl, dodecyl and the like. Preferred "$C_1$ to $C_{12}$ alkyl" groups are methyl, ethyl, iso-butyl, sec-butyl and iso-propyl. Similarly, the term "$C_1$ to $C_{12}$ alkylene" denotes radicals of 1 to 12 carbons connected to two other parts in the compound.

The term "$C_2$ to $C_{12}$ alkenyl" denotes such radicals as vinyl, allyl, 2-butenyl, 3-butenyl, 2-pentenyl, 3-pentenyl, 4-pentenyl, 2-hexenyl, 3-hexenyl, 4-hexenyl, 5-hexenyl, 2-heptenyl, 3-heptenyl, 4-heptenyl, 5-heptenyl, 6-heptenyl, (as well as octenyl, nonenyl, decenyl, undecenyl, dodecenyl radicals attached at any appropriate carbon position and the like) as well as dienes and trienes of straight and branched chains.

The term "$C_2$ to $C_{12}$ alkynyl" denotes such radicals as ethynyl, propynyl, 2-butynyl, 2-pentynyl, 3-pentynyl, 2-hexynyl, 3-hexynyl, 4-hexynyl, 2-heptynyl, 3-heptynyl, 4-heptynyl, 5-heptynyl (as well as octynyl, nonynyl, decynyl, undecynyl, dodecynyl radicals attached at any appropriate carbon position and the like) as well as di- and tri-ynes of straight and branched chains.

The terms "$C_1$ to $C_{12}$ substituted alkyl," "$C_2$ to $C_{12}$ substituted alkenyl," "$C_2$ to $C_{12}$ substituted alkynyl," "$C_1$ to $C_{12}$ substituted alkylene," "$C_2$ to $C_{12}$ substituted alkenylene" and "$C_2$ to $C_{12}$ substituted alkynylene" denote groups are substituted by one or more, and preferably one or two, halogen, hydroxy, protected hydroxy, oxo, protected oxo, $C_3$ to $C_7$ cycloalkyl, phenyl, naphthyl, amino, protected amino, (monosubstituted)amino, protected (monosubstituted)amino, (disubstituted)amino, guanidino, protected guanidino, heterocyclic ring, substituted heterocyclic ring, imidazolyl, indolyl, pyrrolidinyl, $C_1$ to $C_{12}$ alkoxy, $C_1$ to $C_{12}$ acyl, $C_1$ to $C_{12}$ acyloxy, nitro, carboxy, protected carboxy, carbamoyl, carboxamide, protected carboxamide, N—($C_1$ to $C_{12}$ alkyl)carboxamide, protected N—($C_1$ to $C_{12}$ alkyl)carboxamide, N,N-di($C_1$ to $C_{12}$ alkyl) carboxamide, cyano, methylsulfonylamino, thiol, $C_1$ to $C_{10}$ alkylthio or $C_1$ to $C_{10}$ alkylsulfonyl groups. The substituted alkyl groups may be substituted once or more, and preferably once or twice, with the same or with different substituents.

Examples of the above substituted alkyl groups include the 2-oxo-prop-1-yl, 3-oxo-but-1-yl, cyanomethyl, nitromethyl, chloromethyl, hydroxymethyl, tetrahydropyranyloxymethyl, trityloxymethyl, propionyloxymethyl, aminomethyl, carboxymethyl, allyloxycarbonylmethyl, allyloxycarbonylaminomethyl, methoxymethyl, ethoxymethyl, t-butoxymethyl, acetoxymethyl, chloromethyl, bromomethyl, iodomethyl, trifluoromethyl, 6-hydroxyhexyl, 2,4-dichloro(n-butyl), 2-aminopropyl, 1-chloroethyl, 2-chloroethyl, 1-bromoethyl, 2-chloroethyl, 1-fluoroethyl, 2-fluoroethyl, 1-iodoethyl, 2-iodoethyl, 1-chloropropyl, 2-chloropropyl, 3-chloropropyl, 1-bromopropyl, 2-bromopropyl, 3-bromopropyl, 1-fluoropropyl, 2-fluoropropyl, 3-fluoropropyl, 1-iodopropyl, 2-iodopropyl, 3-iodopropyl, 2-aminoethyl, 1-aminoethyl, N-benzoyl-2-aminoethyl, N-acetyl-2-aminoethyl, N-benzoyl-1-aminoethyl, N-acetyl-1-aminoethyl and the like.

Examples of the above substituted alkenyl groups include styrenyl, 3-chloro-propen-1-yl, 3-chloro-buten-1-yl, 3-methoxy-propen-2-yl, 3-phenyl-buten-2-yl, 1-cyano-buten-3-yl and the like. The geometrical isomerism is not critical, and all geometrical isomers for a given substituted alkenyl can be used.

Examples of the above substituted alkynyl groups include phenylacetylen-1-yl, 1-phenyl-2-propyn-1-yl and the like.

The term "oxo" denotes a carbon atom bonded to two additional carbon atoms substituted with an oxygen atom doubly bonded to the carbon atom, thereby forming a ketone moiety.

The term "protected oxo" denotes a carbon atom bonded to two additional carbon atoms substituted with two alkoxy groups or twice bonded to a substituted diol moiety, thereby forming an acyclic or cyclic ketal moiety.

The term "$C_1$ to $C_{12}$ alkoxy" as used herein denotes groups such as methoxy, ethoxy, n-propoxy, isopropoxy, n-butoxy, t-butoxy and like groups. A preferred alkoxy is methoxy. The term "$C_1$ to $C_{12}$ substituted alkoxy" means the alkyl portion of the alkoxy can be substituted in the same manner as in relation to $C_1$ to $C_{12}$ substituted alkyl. Similarly, the term "$C_1$ to $C_{12}$ phenylalkoxy" as used herein means "$C_1$ to $C_{12}$ alkoxy" bonded to a phenyl radical.

The term "$C_1$ to $C_{12}$ acyloxy" denotes herein groups such as formyloxy, acetoxy, propionyloxy, butyryloxy, pivaloyloxy, pentanoyloxy, hexanoyloxy, heptanoyloxy, octanoyloxy, nonanoyloxy, decanoyloxy, undecanoyloxy, dodecanoyloxy and the like.

Similarly, the term "$C_1$ to $C_{12}$ acyl" encompasses groups such as formyl, acetyl, propionyl, butyryl, pentanoyl, pivaloyl, hexanoyl, heptanoyl, octanoyl, nonanoyl, decanoyl, undecanoyl, dodecanoyl, benzoyl and the like. Preferred acyl groups are acetyl and benzoyl.

The term "$C_1$ to $C_{12}$ substituted acyl" denotes the acyl group substituted by one or more, and preferably one or two, halogen, hydroxy, protected hydroxy, oxo, protected oxo, cyclohexyl, naphthyl, amino, protected amino, (monosubstituted)amino, protected (monosubstituted) amino, (disubstituted)amino, guanidino, heterocyclic ring, substituted heterocyclic ring, imidazolyl, indolyl, pyrrolidinyl, $C_1$ to $C_{12}$ alkoxy, $C_1$ to $C_{12}$ acyl, $C_1$ to $C_{12}$ acyloxy, nitro, $C_1$ to $C_{12}$ alkyl ester, carboxy, protected carboxy, carbamoyl, carboxamide, protected carboxamide, N—($C_1$ to $C_{12}$ alkyl)carboxamide, protected N—($C_1$ to $C_{12}$ alkyl)carboxamide, N,N-di($C_1$ to $C_{12}$ alkyl)carboxamide, cyano, methylsulfonylamino, thiol, $C_1$ to $C_{10}$ alkylthio or $C_1$ to $C_{10}$ alkylsulfonyl groups. The substituted acyl groups may be substituted once or more, and preferably once or twice, with the same or with different substituents.

Examples of $C_1$ to $C_{12}$ substituted acyl groups include 4-phenylbutyroyl, 3-phenylbutyroyl, 3-phenylpropanoyl, 2-cyclohexanylacetyl, cyclohexanecarbonyl, 2-furanoyl and 3-dimethylaminobenzoyl.

The substituent term "$C_3$ to $C_7$ cycloalkyl" includes the cyclopropyl, cyclobutyl, cyclopentyl, cyclohexyl or cycloheptyl rings. Similarly, a substituent that can be $C_3$ to $C_7$ cycloalkyl" can also be "$C_5$ to $C_7$ cycloalkyl," which includes the cyclopentyl, cyclohexyl or cycloheptyl rings.

The substituent term "$C_3$ to $C_7$ substituted cycloalkyl" or "$C_5$ to $C_7$ substituted cycloalkyl" indicates the above cycloalkyl rings substituted by one or two halogen, hydroxy, protected hydroxy, $C_1$ to $C_{10}$ alkylthio, $C_1$ to $C_{10}$ alkylsulfoxide, $C_1$ to $C_{10}$ alkylsulfonyl, $C_1$ to $C_{10}$ substituted alkylthio, $C_1$ to $C_{10}$ substituted alkylsulfoxide, $C_1$ to $C_{10}$ substituted alkylsulfonyl, $C_1$ to $C_{12}$ alkyl, $C_1$ to $C_{12}$ alkoxy, $C_1$ to $C_{12}$ substituted alkyl, $C_1$ to $C_{12}$ alkoxy, oxo, protected oxo, (monosubstituted)amino, (disubstituted)amino, trifluoromethyl, carboxy, protected carboxy, phenyl, substituted phenyl, phenylthio, phenylsulfoxide, phenylsulfonyl, amino, or protected amino groups.

The term "cycloalkylene" means a cycloalkyl, as defined above, where the cycloalkyl radical is bonded at two positions connecting together two separate additional groups. Similarly, the term "substituted cycloalkylene" means a cycloalkylene where the cycloalkyl radical is bonded at two positions connecting together two separate additional groups and further bearing at least one additional substituent.

The term "$C_5$ to $C_7$ cycloalkenyl" indicates a 1,2, or 3-cyclopentenyl ring, a 1,2,3 or 4-cyclohexenyl ring or a 1,2,3,4 or 5-cycloheptenyl ring, while the term "substituted $C_5$ to $C_7$ cycloalkenyl" denotes the above $C_5$ to $C_7$ cycloalkenyl rings substituted by a $C_1$ to $C_{12}$ alkyl radical, halogen, hydroxy, protected hydroxy, $C_1$ to $C_{12}$ alkoxy, trifluoromethyl, carboxy, protected carboxy, oxo, protected oxo, (monosubstituted)amino, protected (monosubstituted)amino, (disubstituted)amino, phenyl, substituted phenyl, amino, or protected amino.

The term "$C_5$ to $C_7$ cycloalkenylene" is a cycloalkenyl ring, as defined above, where the cycloalkenyl radical is bonded at two positions connecting together two separate additional groups. Similarly, the term "substituted $C_5$ to $C_7$ cycloalkenylene" means a cycloalkenylene further substituted by halogen, hydroxy, protected hydroxy, $C_1$ to $C_{10}$ alkylthio, $C_1$ to $C_{10}$ alkylsulfoxide, $C_1$ to $C_{10}$ alkylsulfonyl, $C_1$ to $C_{10}$ substituted alkylthio, $C_1$ to $C_{10}$ substituted alkylsulfoxide, $C_1$ to $C_{10}$ substituted alkylsulfonyl, $C_1$ to $C_{12}$ alkyl, $C_1$ to $C_{12}$ alkoxy, $C_1$ to $C_{12}$ substituted alkyl, $C_1$ to $C_{12}$ alkoxy, oxo, protected oxo, (monosubstituted)amino, (disubstituted)amino, trifluoromethyl, carboxy, protected carboxy, phenyl, substituted phenyl, phenylthio, phenylsulfoxide, phenylsulfonyl, amino, or protected amino group.

The term "heterocycle" or "heterocyclic ring" denotes optionally substituted five-membered to eight-membered rings that have 1 to 4 heteroatoms, such as oxygen, sulfur and/or nitrogen, in particular nitrogen, either alone or in conjunction with sulfur or oxygen ring atoms. These five-membered to eight-membered rings may be saturated, fully unsaturated or partially unsaturated, with fully saturated rings being preferred. Preferred heterocyclic rings include morpholino, piperidinyl, piperazinyl, 2-amino-imidazoyl, tetrahydrofurano, pyrrolo, tetrahydrothiophen-yl, hexylmethyleneimino and heptylmethyleneimino.

The term "substituted heterocycle" or "substituted heterocyclic ring" means the above-described heterocyclic ring is substituted with, for example, one or more, and preferably one or two, substituents which are the same or different which substituents can be halogen, hydroxy, protected hydroxy, cyano, nitro, $C_1$ to $C_{12}$ alkyl, $C_1$ to $C_{12}$ alkoxy, $C_1$ to $C_{12}$ substituted alkoxy, $C_1$ to $C_{12}$ acyl, $C_1$ to $C_{12}$ acyloxy, carboxy, protected carboxy, carboxymethyl, protected carboxymethyl, hydroxymethyl, protected hydroxymethyl, amino, protected amino, (monosubstituted)amino, protected (monosubstituted)amino, (disubstituted)amino carboxamide, protected carboxamide, N—($C_1$ to $C_{12}$ alkyl)carboxamide, protected N—($C_1$ to $C_{12}$ alkyl)carboxamide, N,N-di($C_1$ to $C_{12}$ alkyl)carboxamide, trifluoromethyl, N—(($C_1$ to $C_{12}$ alkyl)sulfonyl)amino, N-(phenylsulfonyl) amino, heterocycle or substituted heterocycle groups.

The term "heteroaryl" means a heterocyclic aromatic derivative which is a five-membered or six-membered ring system having from 1 to 4 heteroatoms, such as oxygen, sulfur and/or nitrogen, in particular nitrogen, either alone or in conjunction with sulfur or oxygen ring atoms. Examples of heteroaryls include pyridinyl, pyrimidinyl, and pyrazinyl, pyridazinyl, pyrrolo, furano, oxazolo, isoxazolo, phthalimido, thiazolo and the like.

The term "substituted heteroaryl" means the above-described heteroaryl is substituted with, for example, one or more, and preferably one or two, substituents which are the same or different which substituents can be halogen, hydroxy, protected hydroxy, cyano, nitro, $C_1$ to $C_{12}$ alkyl, $C_1$ to $C_{12}$ alkoxy, $C_1$ to $C_{12}$ substituted alkoxy, $C_1$ to $C_{12}$ acyl, $C_1$ to $C_{12}$ substituted acyl, $C_1$ to $C_{12}$ acyloxy, carboxy, protected carboxy, carboxymethyl, protected carboxymethyl, hydroxymethyl, protected hydroxymethyl, amino, protected amino, (monosubstituted)amino, protected (monosubstituted)amino, (disubstituted)amino, carboxamide, protected carboxamide, N—($C_1$ to $C_{12}$ alkyl)carboxamide, protected N—($C_1$ to $C_{12}$ alkyl)carboxamide, N,N-di($C_1$ to $C_{12}$ alkyl)carboxamide, trifluoromethyl, N—(($C_1$ to $C_{12}$ alkyl)sulfonyl)amino or N-(phenylsulfonyl) amino groups.

The term "$C_7$ to $C_{18}$ phenylalkyl" denotes a $C_1$ to $C_{12}$ alkyl group substituted at any position within the alkyl chain by a phenyl. The definition includes groups of the formula: phenyl-alkyl, -alkyl-phenyl and -alkyl-phenyl-alkyl. Examples of such a group include benzyl, 2-phenylethyl, 3-phenyl(n-propyl), 4-phenylhexyl, 3-phenyl(n-amyl), 3-phenyl(sec-butyl) and the like. Preferred $C_7$ to $C_{18}$ phenylalkyl groups are any one of the preferred alkyl groups described herein combined with a phenyl group.

Similarly, the term "$C_1$ to $C_{12}$ heterocycloalkyl" denotes a $C_1$ to $C_{12}$ alkyl group substituted at any position within the alkyl chain by a "heterocycle," as defined herein. The definition includes groups of the formula: -heterocyclic-alkyl, -alkyl-heterocyclic and -alkyl-heterocyclic-alkyl. Examples of such a group include 2-pyridylethyl, 3-pierydyl (n-propyl), 4-furylhexyl, 3-piperazyl(n-amyl), 3-morpholyl (sec-butyl) and the like. Preferred $C_1$ to $C_{12}$ heterocycloalkyl groups are any one of the preferred alkyl groups described herein combined with any one of the preferred heterocycle groups described herein.

The terms "$C_7$ to $C_{18}$ substituted phenylalkyl" and "$C_1$ to $C_{12}$ substituted heterocycloalkyl" denote a $C_7$ to $C_{18}$ phenylalkyl group or $C_1$ to $C_{12}$ heterocycloalkyl substituted (on the alkyl or, where applicable, phenyl or heterocyclic portion) with one or more, and preferably one or two, groups chosen from halogen, hydroxy, protected hydroxy, oxo, protected oxo, amino, protected amino, (monosubstituted) amino, protected (monosubstituted)amino, (disubstituted) amino, guanidino, protected guanidino, heterocyclic ring, substituted heterocyclic ring, $C_1$ to $C_{12}$ alkyl, $C_1$ to $C_{12}$ substituted alkyl, $C_1$ to $C_{12}$ alkoxy, $C_1$ to $C_{12}$ substituted alkoxy, $C_1$ to $C_{12}$ acyl, $C_1$ to $C_{12}$ substituted acyl, $C_1$ to $C_{12}$ acyloxy, nitro, carboxy, protected carboxy, carbamoyl, carboxamide, protected carboxamide, N—($C_1$ to $C_{12}$ alkyl) carboxamide, protected N—($C_1$ to $C_{12}$ alkyl)carboxamide, N,N—($C_1$ to $C_{12}$ dialkyl)carboxamide, cyano, N—($C_1$ to $C_{12}$ alkylsulfonyl)amino, thiol, $C_1$ to $C_{10}$ alkylthio, $C_1$ to $C_{10}$ alkylsulfonyl groups; and/or the phenyl group may be substituted with one or more, and preferably one or two, substituents chosen from halogen, hydroxy, protected hydroxy, cyano, nitro, $C_1$ to $C_{12}$ alkyl, $C_1$ to $C_{12}$ substituted alkyl, $C_1$ to $C_{12}$ alkoxy, $C_1$ to $C_{12}$ substituted alkoxy, $C_1$ to $C_{12}$ acyl, $C_1$ to $C_{12}$ substituted acyl, $C_1$ to $C_{12}$ acyloxy, carboxy, protected carboxy, carboxymethyl, protected carboxymethyl, hydroxymethyl, protected hydroxymethyl, amino, protected amino, (monosubstituted)amino, protected (monosubstituted)amino, (disubstituted)amino, carboxamide, protected carboxamide, N—($C_1$ to $C_{12}$ alkyl) carboxamide, protected N—($C_1$ to $C_{12}$ alkyl)carboxamide, N,N-di($C_1$ to $C_{12}$ alkyl)carboxamide, trifluoromethyl, N—(($C_1$ to $C_{12}$ alkyl)sulfonyl)amino, N-(phenylsulfonyl) amino, cyclic $C_2$ to $C_{12}$ alkylene or a phenyl group, substituted or unsubstituted, for a resulting biphenyl group. The substituted alkyl, phenyl or heterocyclic groups may be substituted with one or more, and preferably one or two, substituents which can be the same or different.

Examples of the term "$C_7$ to $C_{18}$ substituted phenylalkyl" include groups such as 2-phenyl-1-chloroethyl, 2-(4-methoxyphenyl)ethyl, 4-(2,6-dihydroxy phenyl)n-hexyl, 2-(5-cyano-3-methoxyphenyl)n-pentyl, 3-(2,6-dimethylphenyl)n-propyl, 4-chloro-3-aminobenzyl, 6-(4-methoxyphenyl)-3-carboxy(n-hexyl), 5-(4-aminomethylphenyl)-3-(aminomethyl)n-pentyl, 5-phenyl-3-oxo-n-pent-1-yl and the like.

The term "$C_7$ to $C_{18}$ phenylalkylene" specifies a $C_7$ to $C_{18}$ phenylalkyl, as defined above, where the phenylalkyl radical is bonded at two different positions connecting together two separate additional groups. The definition includes groups of the formula: -phenyl-alkyl- and -alkyl-phenyl-alkyl-. Substitutions on the phenyl ring can be 1,2, 1,3 or 1,4.

Similarly, the term "$C_1$ to $C_{12}$ heterocycloalkylene" specifies a $C_1$ to $C_{12}$ heterocycloalkyl, as defined above, where the heterocycloalkyl radical is bonded at two different positions connecting together two separate additional groups. The definition includes groups of the formula: heterocyclic-alkyl-, -alkyl-heterocyclic and -alkyl-heterocyclic-alkyl-.

The terms "$C_7$ to $C_{18}$ substituted phenylalkylene" and "$C_1$ to $C_{12}$ substituted heterocycloalkylene" means a $C_7$ to $C_{18}$ phenylalkylene or $C_1$ to $C_{12}$ heterocycloalkylene as defined above that is further substituted by halogen, hydroxy, protected hydroxy, $C_1$ to $C_{10}$ alkylthio, $C_1$ to $C_{10}$ alkylsulfoxide, $C_1$ to $C_{10}$ alkylsulfonyl, $C_1$ to $C_{10}$ substituted alkylthio, $C_1$ to $C_{10}$ substituted alkylsulfoxide, $C_1$ to $C_{10}$ substituted alkylsulfonyl, $C_1$ to $C_{12}$ alkyl, $C_1$ to $C_{12}$ alkoxy, $C_1$ to $C_{12}$ substituted alkyl, $C_1$ to $C_{12}$ alkoxy, oxo, protected oxo, (monosubstituted)amino, (disubstituted)amino, trifluoromethyl, carboxy, protected carboxy, phenyl, substituted phenyl, phenylthio, phenylsulfoxide, phenylsulfonyl, amino, or protected amino group on the phenyl ring or on the alkyl group.

The term "substituted phenyl" specifies a phenyl group substituted with one or more, and preferably one or two, moieties chosen from the groups consisting of halogen, hydroxy, protected hydroxy, cyano, nitro, $C_1$ to $C_{12}$ alkyl, $C_1$ to $C_{12}$ substituted alkyl, $C_1$ to $C_{12}$ alkoxy, $C_1$ to $C_{12}$ substituted alkoxy, $C_1$ to $C_{12}$ acyl, $C_1$ to $C_{12}$ substituted acyl, $C_1$ to $C_{12}$ acyloxy, carboxy, protected carboxy, carboxymethyl, protected carboxymethyl, hydroxymethyl, protected hydroxymethyl, amino, protected amino, (monosubstituted)amino, protected (monosubstituted) amino, (disubstituted)amino, carboxamide, protected carboxamide, N—($C_1$ to $C_{12}$ alkyl)carboxamide, protected N—($C_1$ to $C_{12}$ alkyl)carboxamide, N,N-di($C_1$ to $C_{12}$ alkyl) carboxamide, trifluoromethyl, N—(($C_1$ to $C_{12}$ alkyl) sulfonyl)amino, N-(phenylsulfonyl)amino or phenyl, wherein the phenyl is substituted or unsubstituted, such that, for example, a biphenyl results.

Examples of the term "substituted phenyl" includes a mono- or di(halo)phenyl group such as 2, 3 or 4-chlorophenyl, 2,6-dichlorophenyl, 2,5-dichlorophenyl, 3,4-dichlorophenyl, 2, 3 or 4-bromophenyl, 3,4-dibromophenyl, 3-chloro-4-fluorophenyl, 2, 3 or 4-fluorophenyl and the like; a mono or di(hydroxy)phenyl group such as 2, 3 or 4-hydroxyphenyl, 2,4-dihydroxyphenyl, the protected-hydroxy derivatives thereof and the like; a nitrophenyl group such as 2, 3 or 4-nitrophenyl; a cyanophenyl group, for example, 2, 3 or 4-cyanophenyl; a mono- or di(alkyl)phenyl group such as 2, 3 or 4-methylphenyl, 2,4-dimethylphenyl, 2, 3 or 4-(isopropyl)phenyl, 2, 3 or 4-ethylphenyl, 2, 3 or 4-(n-propyl) phenyl and the like; a mono or di(alkoxyl)phenyl group, for example, 2,6-dimethoxyphenyl, 2, 3 or 4-methoxyphenyl, 2, 3 or 4-ethoxyphenyl, 2, 3 or 4-(isopropoxy)phenyl, 2, 3 or 4-(t-butoxy)phenyl, 3-ethoxy-4-methoxyphenyl and the like; 2, 3 or 4-trifluoromethylphenyl; a mono- or dicarboxyphenyl or (protected carboxy)phenyl group such as 2, 3 or 4-carboxyphenyl or 2,4-di(protected carboxy)phenyl; a mono-or di(hydroxymethyl)phenyl or (protected hydroxymethyl)phenyl such as 2, 3, or 4-(protected hydroxymethyl)phenyl or 3,4-di(hydroxymethyl)phenyl; a mono- or di(aminomethyl)phenyl or (protected aminomethyl)phenyl such as 2, 3 or 4-(aminomethyl)phenyl or 2,4-(protected aminomethyl)phenyl; or a mono- or di(N-(methylsulfonylamino))phenyl such as 2, 3 or 4-(N-(methylsulfonylamino))phenyl. Also, the term "substituted phenyl" represents disubstituted phenyl groups wherein the substituents are different, for example, 3-methyl-4-hydroxyphenyl, 3-chloro-4-hydroxyphenyl, 2-methoxy-4-bromophenyl, 4-ethyl-2-hydroxyphenyl, 3-hydroxy-4-nitrophenyl, 2-hydroxy 4-chlorophenyl and the like.

The term "phenoxy" denotes a phenyl bonded to an oxygen atom, wherein the binding to the rest of the molecule is through the oxygen atom. The term "substituted phenoxy" specifies a phenoxy group substituted with one or more, and preferably one or two, moieties chosen from the groups consisting of halogen, hydroxy, protected hydroxy, cyano, nitro, $C_1$ to $C_{12}$ alkyl, $C_1$ to $C_{12}$ alkoxy, $C_1$ to $C_{12}$ substituted alkoxy, $C_1$ to $C_{12}$ acyl, $C_1$ to $C_{12}$ acyloxy, carboxy, protected carboxy, carboxymethyl, protected carboxymethyl, hydroxymethyl, protected hydroxymethyl, amino, protected amino, (monosubstituted)amino, protected (monosubstituted)amino, (disubstituted)amino, carboxamide, protected carboxamide, N—($C_1$ to $C_{12}$ alkyl) carboxamide, protected N—($C_1$ to $C_{12}$ alkyl)carboxamide, N,N-di($C_1$ to $C_{12}$ alkyl)carboxamide, trifluoromethyl, N—(($C_1$ to $C_{12}$ alkyl)sulfonyl)amino and N-(phenylsulfonyl)amino.

Examples of substituted phenoxy include 2-methylphenoxy, 2-ethylphenoxy, 2-propylphenoxy, 2-isopropylphenoxy, 2-sec-butylphenoxy, 2-tert-butylphenoxy, 2-allylphenoxy, 2-propenylphenoxy, 2-cyclopentylphenoxy, 2-fluorophenoxy, 2-(trifluoromethyl) phenoxy, 2-chlorophenoxy, 2-bromophenoxy, 2-methoxyphenoxy, 2-ethoxyphenoxy, 2-isopropoxyphenoxy, 3-methylphenoxy, 3-ethylphenoxy, 3-isopropylphenoxy, 3-tert-butylphenoxy, 3-pentadecylphenoxy, 3-(trifluoromethyl)phenoxy, 3-fluorophenoxy, 3-chlorophenoxy, 3-bromophenoxy, 3-iodophenoxy, 3-methoxyphenoxy, 3-(trifluoromethoxy) phenoxy, 4-methylphenoxy, 4-ethylphenoxy, 4-propylphenoxy, 4-isopropylphenoxy, 4-sec-butylphenoxy, 4-tert-butylphenoxy, 4-tert-amylphenoxy, 4-nonylphenoxy, 4-dodecylphenoxy, 4-cyclopenylphenoxy, 4-(trifluoromethyl)phenoxy, 4-fluorophenoxy, 4-chlorophenoxy, 4-bromophenoxy, 4-iodophenoxy, 4-methoxyphenoxy, 4-(trifluoromethoxy)phenoxy, 4-ethoxyphenoxy, 4-propoxyphenoxy, 4-butoxyphenoxy, 4-hexyloxyphenoxy, 4-heptyloxyphenoxy, 2,3-dimethylphenoxy, 5,6,7,8-tetrahydro-1-naphthoxy, 2,3-dichlorophenoxy, 2,3-dihydro-2,2-dimethyl-7-benzofuranoxy, 2,3-dimethoxyphenoxy, 2,6-dimethylphenoxy, 2,6-diisopropylphenoxy, 2,6-di-sec-butylphenoxy, 2-tert-butyl-6-methylphenoxy, 2,6-di-tert-butylphenoxy, 2-allyl-6-methylphenoxy, 2,6-difluorophenoxy, 2,3-difluorophenoxy, 2,6-dichlorophenoxy, 2,6-dibromophenoxy, 2-fluoro-6-methoxyphenoxy, 2,6-dimethoxyphenoxy, 3,5-dimethylphenoxy, 5-isopropyl-3-methylphenoxy, 3,5-di-tert-butylphenoxy, 3,5-bis(trifluoromethyl)phenoxy, 3,5-difluorophenoxy, 3,5-dichlorophenoxy, 3,5-dimethoxyphenoxy, 3-chloro-5-methoxyphenoxy, 3,4-dimethylphenoxy, 5-indanoxy, 5,6,7,8-tetrahydro-2-naphthoxy, 4-chloro-3-methylphenoxy, 2,4-dimethylphenoxy, 2,5-dimethylphenoxy, 2-isopropyl-5-methylphenoxy, 4-isopropyl-3-methylphenoxy, 5-isopropyl-2-methylphenoxy, 2-tert-butyl-5-methylphenoxy, 2-tert-butyl-4-methylphenoxy, 2,4-di-tert-butylphenoxy, 2,4-di-tert-amylphenoxy, 4-fluoro-2-methylphenoxy, 4-fluoro-3-methylphenoxy, 2-chloro-4-methylphenoxy, 2-chloro-5-methylphenoxy, 4-chloro-2-methylphenoxy, 4-chloro-3-ethylphenoxy, 2-bromo-4-methylphenoxy, 4-iodo-2-methylphenoxy, 2-chloro-5-(trifluoromethyl)phenoxy, 2,4-difluorophenoxy, 2,5-difluorophenoxy, 3,4-difluorophenoxy, 4-chloro-2-fluorophenoxy, 3-chloro-4-fluorophenoxy, 4-chloro-3-fluorophenoxy, 2-bromo-4-fluorophenoxy, 4-bromo-2-fluorophenoxy, 2-bromo-5-fluorophenoxy, 2,4-dichlorophenoxy, 3,4-dichlorophenoxy, 2,5-dichlorophenoxy, 2-bromo-4-chlorophenoxy, 2-chloro-4-fluorophenoxy, 4-bromo-2-chlorophenoxy, 2,4-dibromophenoxy, 2-methoxy-4-methylphenoxy, 4-allyl-2-methylphenoxy, trans-2-ethoxy-5-(1-propenyl)phenoxy, 2-methoxy-4-propenylphenoxy, 3,4-dimethoxyphenoxy, 3-ethoxy-4-methoxyphenoxy, 4-allyl-2,6-dimethoxyphenoxy, 3,4-methylenedioxyphenoxy, 2,3,6-trimethylphenoxy, 2,4-dichloro-3-methylphenoxy, 2,3,4-trifluorophenoxy, 2,3,6-trifluorophenoxy, 2,3,5-trifluorophenoxy, 2,3,4-trichlorophenoxy, 2,3,6-trichlorophenoxy, 2,3,5-trimethylphenoxy, 3,4,5-trimethylphenoxy, 4-chloro-3,5-dimethylphenoxy, 4-bromo-3,5-dimethylphenoxy, 2,4,6-trimethylphenoxy, 2,6-bis(hydroxymethyl)-4-methylphenoxy, 2,6-di-tert-butyl-4-methylphenoxy, 2,6-di-tert-butyl-4-methoxyphenoxy, 2,4,5-trifluorophenoxy, 2-chloro-3,5-difluorophenoxy, 2,4,6-trichlorophenoxy, 3,4,5-trimethoxyphenoxy, 2,3,5- trichlorophenoxy, 4-bromo-2,6-dimethylphenoxy, 4-bromo-6-chloro-2-methylphenoxy, 2,6-dibromo-4-methylphenoxy, 2,6-dichloro-4-fluorophenoxy, 2,6-dibromo-4-fluorophenoxy, 2,4,6-tribromophenoxy, 2,4,6-triiodophenoxy, 2-chloro-4,5-dimethylphenoxy, 4-chloro-2-isopropyl-5-methylphenoxy, 2-bromo-4,5-difluorophenoxy, 2,4,5-trichlorophenoxy, 2,3,5,6-tetrafluorophenoxy and the like.

The term "$C_7$ to $C_{18}$ substituted phenylalkoxy" denotes a $C_7$ to $C_{18}$ phenylalkoxy group bonded to the rest of the molecule through the oxygen atom, wherein the phenylalkyl portion is substituted with one or more, and preferably one or two, groups selected from halogen, hydroxy, protected hydroxy, oxo, protected oxo, amino, protected amino, (monosubstituted)amino, protected (monosubstituted) amino, (disubstituted)amino, guanidino, heterocyclic ring, substituted heterocyclic ring, $C_1$ to $C_{12}$ alkoxy, $C_1$ to $C_{12}$ acyl, $C_1$ to $C_{12}$ acyloxy, nitro, carboxy, protected carboxy, carbamoyl, carboxamide, protected carboxamide, N—($C_1$ to $C_{12}$ alkyl)carboxamide, protected N—($C_1$ to $C_{12}$ alkyl)carboxamide, N,N—($C_1$ to $C_{12}$ dialkyl)carboxamide, cyano, N—($C_1$ to $C_{12}$ alkylsulfonyl)amino, thiol, $C_1$ to $C_{10}$ alkylthio, $C_1$ to $C_{10}$ alkylsulfonyl groups; and/or the phenyl group can be substituted with one or more, and preferably one or two, substituents chosen from halogen, hydroxy, protected hydroxy, cyano, nitro, $C_1$ to $C_{12}$ alkyl, $C_1$ to $C_{12}$ alkoxy, $C_1$ to $C_{12}$ acyl, $C_1$ to $C_{12}$ acyloxy, carboxy, protected carboxy, carboxymethyl, protected carboxymethyl, hydroxymethyl, protected hydroxymethyl, amino, protected amino, (monosubstituted)amino, protected (monosubstituted)amino, (disubstituted)amino, carboxamide, protected carboxamide, N—($C_1$ to $C_{12}$ alkyl) carboxamide, protected N—($C_1$ to $C_{12}$ alkyl) carboxamide, N,N-di($C_1$ to $C_{12}$ alkyl)carboxamide, trifluoromethyl, N—(($C_1$ to $C_{12}$ alkyl)sulfonyl)amino, N-(phenylsulfonyl) amino or a phenyl group, substituted or unsubstituted, for a resulting biphenyl group. The substituted alkyl or phenyl groups may be substituted with one or more, and preferably one or two, substituents which can be the same or different.

Examples of the term "$C_7$ to $C_{18}$ substituted phenylalkoxy" include groups such as 2-(4-hydroxyphenyl)ethoxy, 4-(4-methoxyphenyl)butoxy, (2R)-3-phenyl-2-amino-propoxy, (2S)-3-phenyl-2-amino-propoxy, 2-indanoxy, 6-phenyl-1-hexanoxy, cinnamyloxy, (+/−)-2-phenyl-1-propoxy, 2,2-dimethyl-3-phenyl-1-propoxy and the like.

The term "phthalimide" means a cyclic imide which is made from phthalic acid, also called 1,2-benzenedicarboxylic acid. The term "substituted phthalimide" specifies a phthalimide group substituted with one or more, and preferably one or two, moieties chosen from the groups consisting of halogen, hydroxy, protected hydroxy, cyano, nitro, $C_1$ to $C_{12}$ alkyl, $C_1$ to $C_{12}$ alkoxy, $C_1$ to $C_{12}$ substituted alkoxy, $C_1$ to $C_{12}$ acyl, $C_1$ to $C_{12}$ acyloxy, carboxy, protected carboxy, carboxymethyl, protected carboxymethyl, hydroxymethyl, protected hydroxymethyl, amino, protected amino, (monosubstituted)amino, protected (monosubstituted)amino, (disubstituted)amino, carboxamide, protected carboxamide, N—($C_1$ to $C_{12}$ alkyl) carboxamide, protected N—($C_1$ to $C_{12}$ alkyl)carboxamide, N,N-di($C_1$ to $C_{12}$ alkyl)carboxamide, trifluoromethyl, N—(($C_1$ to $C_{12}$ alkyl)sulfonyl)amino and N-(phenylsulfonyl)amino.

Examples of substituted phthalimides include 4,5-dichlorophthalimido, 3-fluorophthalimido, 4-methoxyphthalimido, 3-methylphthalimido, 4-carboxyphthalimido and the like.

The term "substituted naphthyl" specifies a naphthyl group substituted with one or more, and preferably one or two, moieties either on the same ring or on different rings chosen from the groups consisting of halogen, hydroxy, protected hydroxy, cyano, nitro, $C_1$ to $C_6$ alkyl, $C_1$ to $C_7$ alkoxy, $C_1$ to $C_7$ acyl, $C_1$ to $C_7$ acyloxy, carboxy, protected carboxy, carboxymethyl, protected carboxymethyl, hydroxymethyl, protected hydroxymethyl, amino, protected amino, (monosubstituted)amino, protected (monosubstituted)amino, (disubstituted)amino, carboxamide, protected carboxamide, N—($C_1$ to $C_{12}$ alkyl) carboxamide, protected N—($C_1$ to $C_{12}$ alkyl)carboxamide, N,N-di($C_1$ to $C_{12}$ alkyl)carboxamide, trifluoromethyl, N—(($C_1$ to $C_{12}$ alkyl)sulfonyl)amino or N-(phenylsulfonyl) amino.

Examples of the term "substituted naphthyl" includes a mono or di(halo)naphthyl group such as 1, 2, 3, 4, 5, 6, 7 or 8-chloronaphthyl, 2,6-dichloronaphthyl, 2,5-dichloronaphthyl, 3,4-dichloronaphthyl, 1, 2, 3, 4, 5, 6, 7 or 8-bromonaphthyl, 3,4-dibromonaphthyl, 3-chloro-4-fluoronaphthyl, 1, 2, 3, 4, 5, 6, 7 or 8-fluoronaphthyl and the like; a mono or di(hydroxy)naphthyl group such as 1, 2, 3, 4, 5, 6, 7 or 8-hydroxynaphthyl, 2,4-dihydroxynaphthyl, the protected-hydroxy derivatives thereof and the like; a nitronaphthyl group such as 3- or 4-nitronaphthyl; a cyanonaphthyl group, for example, 1, 2, 3, 4, 5, 6, 7 or 8-cyanonaphthyl; a mono- or di(alkyl)naphthyl group such as 2, 3, 4, 5, 6, 7 or 8-methylnaphthyl, 1,2,4-dimethylnaphthyl, 1, 2, 3, 4, 5, 6, 7 or 8-(isopropyl)naphthyl, 1, 2, 3, 4, 5, 6, 7 or 8-ethylnaphthyl, 1, 2, 3, 4, 5, 6, 7 or 8-(n-propyl)naphthyl and the like; a mono or di(alkoxy) naphthyl group, for example, 2,6-dimethoxynaphthyl, 1, 2, 3, 4, 5, 6, 7 or 8-methoxynaphthyl, 1, 2, 3, 4, 5, 6, 7 or 8-ethoxynaphthyl, 1, 2, 3, 4, 5, 6, 7 or 8-(isopropoxy) naphthyl, 1, 2, 3, 4, 5, 6, 7 or 8-(t-butoxy)naphthyl, 3-ethoxy-4-methoxynaphthyl and the like; 1, 2, 3, 4, 5, 6, 7 or 8-trifluoromethylnaphthyl; a mono- or dicarboxynaphthyl or (protected carboxy)naphthyl group such as 1, 2, 3, 4, 5, 6, 7 or 8-carboxynaphthyl or 2,4-di(-protected carboxy) naphthyl; a mono-or di(hydroxymethyl)naphthyl or (protected hydroxymethyl)naphthyl such as 1, 2, 3, 4, 5, 6, 7 or 8-(protected hydroxymethyl)naphthyl or 3,4-di (hydroxymethyl)naphthyl; a mono- or di(amino)naphthyl or (protected amino)naphthyl such as 1, 2, 3, 4, 5, 6, 7 or 8-(amino)naphthyl or 2,4-(protected amino)-naphthyl, a mono- or di(aminomethyl)naphthyl or (protected aminomethyl)naphthyl such as 2, 3, or 4-(aminomethyl) naphthyl or 2,4-(protected aminomethyl)-naphthyl; or a mono- or di-(N-methylsulfonylamino) naphthyl such as 1, 2, 3, 4, 5, 6, 7 or 8-(N-methylsulfonylamino)naphthyl. Also, the term "substituted naphthyl" represents disubstituted naphthyl groups wherein the substituents are different, for example, 3-methyl-4-hydroxynaphth-1-yl, 3-chloro-4-hydroxynaphth-2-yl, 2-methoxy-4-bromonaphth-1-yl, 4-ethyl-2-hydroxynaphth-1-yl, 3-hydroxy-4-nitronaphth-2-yl, 2-hydroxy-4-chloronaphth-1-yl, 2-methoxy-7-bromonaphth-1-yl, 4-ethyl-5-hydroxynaphth-2-yl, 3-hydroxy-8-nitronaphth-2-yl, 2-hydroxy-5-chloronaphth-1-yl and the like.

The term "naphthylene" means a naphthyl radical bonded at two positions connecting together two separate additional groups. Similarly, the term "substituted napthylene" means a naphthylene group that is further substituted by halogen, hydroxy, protected hydroxy, $C_1$ to $C_{10}$ alkylthio, $C_1$ to $C_{10}$ alkylsulfoxide, $C_1$ to $C_{10}$ alkylsulfonyl, $C_1$ to $C_{10}$ substituted alkylthio, $C_1$ to $C_{10}$ substituted alkylsulfoxide, $C_1$ to $C_{10}$ substituted alkylsulfonyl, $C_1$ to $C_{12}$ alkyl, $C_1$ to $C_{12}$ alkoxy, $C_1$ to $C_{12}$ substituted alkyl, $C_1$ to $C_{12}$ alkoxy, oxo, protected oxo, (monosubstituted)amino, (disubstituted)amino, trifluoromethyl, carboxy, protected carboxy, phenyl, substituted phenyl, phenylthio, phenylsulfoxide, phenylsulfonyl, amino, or protected amino group.

The terms "halo" and "halogen" refer to the fluoro, chloro, bromo or iodo atoms. There can be one or more halogens, which are the same or different. Preferred halogens are chloro and fluoro.

The term "(monosubstituted)amino" refers to an amino group with one substituent chosen from the group consisting of phenyl, substituted phenyl, $C_1$ to $C_{12}$ alkyl, $C_1$ to $C_{12}$ substituted alkyl, $C_1$ to $C_{12}$ acyl, $C_1$ to $C_{12}$ substituted acyl, $C_2$ to $C_{12}$ alkenyl, $C_2$ to $C_{12}$ substituted alkenyl, $C_2$ to $C_{12}$ alkynyl, $C_2$ to $C_{12}$ substituted alkynyl, $C_7$ to $C_{18}$ phenylalkyl, $C_7$ to $C_{18}$ substituted phenylalkyl, heterocyclic ring, substituted heterocyclic ring, $C_1$ to $C_{12}$ heterocycloalkyl and $C_1$ to $C_{12}$ substituted heterocycloalkyl. The (monosubstituted)amino can additionally have an amino-protecting group as encompassed by the term "protected (monosubstituted)amino."

The term "(disubstituted)amino" refers to an amino group with two substituents chosen from the group consisting of phenyl, substituted phenyl, $C_1$ to $C_{12}$ alkyl, $C_1$ to $C_{12}$ substituted alkyl, $C_1$ to $C_{12}$ acyl, $C_2$ to $C_{12}$ alkenyl, $C_2$ to $C_{12}$ alkynyl, $C_7$ to $C_{18}$ phenylalkyl, $C_7$ to $C_{18}$ substituted phenylalkyl, $C_1$ to $C_{12}$ heterocycloalkyl and $C_1$ to $C_{12}$ substituted heterocycloalkyl. The two substituents can be the same or different.

The term "amino-protecting group" as used herein refers to substituents of the amino group commonly employed to block or protect the amino functionality while reacting other functional groups of the molecule. The term "protected (monosubstituted)amino" means there is an amino-protecting group on the monosubstituted amino nitrogen atom. In addition, the term "protected carboxamide" means there is an amino-protecting group on the carboxamide nitrogen. Similarly, the term "protected N—($C_1$ to $C_{12}$ alkyl)carboxamide" means there is an amino-protecting group on the carboxamide nitrogen.

Examples of such amino-protecting groups include the formyl ("For") group, the trityl group, the phthalimido group, the trichloroacetyl group, the chloroacetyl, bromoacetyl, and iodoacetyl groups, urethane-type blocking groups, such as t-butoxycarbonyl ("Boc"), 2-(4-biphenylyl)propyl-2-oxycarbonyl ("Bpoc"), 2-phenylpropyl-2-oxycarbonyl ("Poc"), 2-(4-xenyl)isopropoxycarbonyl, 1,1-diphenylethyl-1-oxycarbonyl, 1,1-diphenylpropyl-1-oxycarbonyl, 2-(3,5-dimethoxyphenyl)propyl-2-oxycarbonyl ("Ddz"), 2-(p-toluyl)propyl-2-oxycarbonyl, cyclopentanyloxycarbonyl, 1-methylcyclopentanyloxycarbonyl, cyclohexanyloxycarbonyl, 1-methylcyclohexanyloxycarbonyl, 2-methylcyclohexanyloxycarbonyl, 2-(4-toluylsulfonyl)-ethoxycarbonyl, 2-(methylsulfonyl)ethoxycarbonyl, 2-(triphenylphosphino)-ethoxycarbonyl, 9-fluorenylmethoxycarbonyl ("Fmoc"), 2-(trimethylsilyl)ethoxycarbonyl, allyloxycarbonyl, 1-(trimethylsilylmethyl)prop-1-enyloxycarbonyl, 5-benzisoxalylmethoxycarbonyl, 4-acetoxybenzyl-oxycarbonyl, 2,2,2-trichloroethoxycarbonyl, 2-ethynyl-2-propoxycarbonyl, cyclopropylmethoxycarbonyl, isobornyloxycarbonyl, 1-piperidyloxycarbonyl, benzyloxycarbonyl ("Cbz"), 4-phenylbenzyloxycarbonyl, 2-methylbenzyloxy-carbonyl, -2,4,5,-tetramethylbenzyloxycarbonyl ("Tmz"), 4-methoxybenzyloxycarbonyl, 4-fluorobenzyloxycarbonyl, 4-chlorobenzyloxycarbonyl, 3-chlorobenzyloxycarbonyl, 2-chlorobenzyloxycarbonyl, 2,4-dichlorobenzyloxycarbonyl, 4-bromobenzyloxycarbonyl, 3-bromobenzyloxycarbonyl, 4-nitrobenzyloxy-carbonyl, 4-cyanobenzyloxycarbonyl, 4-(decyloxy) benzyloxycarbonyl and the like; the benzoylmethylsulfonyl group, dithiasuccinoyl ("Dts"), the 2-(nitro)phenylsulfenyl group ("Nps"), the diphenyl-phosphine oxide group and like amino-protecting groups. The species of amino-protecting group employed is not critical so long as the derivatized amino group is stable to the conditions of the subsequent reaction(s) and can be removed at the appropriate point without disrupting the remainder of the compounds. Preferred amino-protecting groups are Boc, Cbz and Fmoc. Further examples of amino-protecting groups embraced by the above term are well known in organic synthesis and the peptide art and are described by, for example, T. W. Greene and P. G. M. Wuts, "Protective Groups in Organic Synthesis," 2nd ed., John Wiley and Sons, New York, N.Y., 1991, Chapter 7, M. Bodanzsky, "Principles of Peptide Synthesis," 1st and 2nd revised ed., Springer-Verlag, New York, N.Y., 1984 and 1993, and Stewart and Young, "Solid Phase Peptide Synthesis," 2nd ed., Pierce Chemical Co., Rockford, Ill., 1984, each of which is incorporated herein by reference. The related term "protected amino" defines an amino group substituted with an amino-protecting group discussed above.

The term "protected guanidino" as used herein refers to an "amino-protecting group" on one or two of the guanidino nitrogen atoms. Examples of "protected guanidino" groups are described by T. W. Greene and P. G. M. Wuts; M. Bodanzsky; and Stewart and Young, supra.

The term "carboxy-protecting group" as used herein refers to one of the ester derivatives of the carboxylic acid group commonly employed to block or protect the carboxylic acid group while reactions are carried out on other functional groups on the compound. Examples of such carboxylic acid protecting groups include t-butyl, 4-nitrobenzyl, 4-methoxybenzyl, 3,4-dimethoxybenzyl, 2,4-dimethoxybenzyl, 2,4,6-trimethoxybenzyl, 2,4,6-trimethylbenzyl, pentamethylbenzyl, 3,4-methylenedioxybenzyl, benzhydryl, 4,4'-dimethoxytrityl, 4,4',4"-trimethoxytrityl, 2-phenylpropyl, trimethylsilyl, t-butyldimethylsilyl, phenacyl, 2,2,2-trichloroethyl, -(trimethylsilyl)ethyl, -(di(n-butyl)methylsilyl)ethyl, p-toluenesulfonylethyl, 4-nitrobenzylsulfonylethyl, allyl, cinnamyl, 1-(trimethylsilylmethyl)-propenyl and like moieties. The species of carboxy-protecting group employed is not critical so long as the derivatized carboxylic acid is stable to the conditions of subsequent reaction(s) and can be removed at the appropriate point without disrupting the remainder of the molecule. Further examples of these groups are found in E. Haslam, "Protective Groups in Organic Chemistry," J. G. W. McOmie, Ed., Plenum Press, New York, N.Y., 1973, Chapter 5, and T. W. Greene and P. G. M. Wuts, "Protective Groups in Organic Synthesis," 2nd ed., John Wiley and Sons, New York, N.Y., 1991, Chapter 5, each of which is incorporated herein by reference. A related term is "protected carboxy," which refers to a carboxy group substituted with one of the above carboxy-protecting groups.

The term "hydroxy-protecting group" refers to readily cleavable groups bonded to hydroxyl groups, such as the tetrahydropyranyl, 2-methoxypropyl, 1-ethoxyethyl, methoxymethyl, 2-methoxyethoxymethyl, methylthiomethyl, t-butyl, t-amyl, trityl, 4-methoxytrityl, 4,4'-dimethoxytrityl, 4,4',4"-trimethoxytrityl, benzyl, allyl, trimethylsilyl, (t-butyl)dimethylsilyl, 2,2,2-trichloroethoxycarbonyl groups and the like. The species of hydroxy-protecting groups is not critical so long as the derivatized hydroxyl group is stable to the conditions of subsequent reaction(s) and can be removed at the appropriate point without disrupting the remainder of the molecule. Further examples of hydroxy-protecting groups are described by C. B. Reese and E. Haslam, "Protective Groups in Organic Chemistry," J. G. W. McOmie, Ed., Plenum Press, New York, N.Y., 1973, Chapters 3 and 4, respectively, and T. W. Greene and P. G. M. Wuts, "Protective Groups in Organic Synthesis," 2nd ed., John Wiley and Sons, New York, N.Y., 1991, Chapters 2 and 3. Related terms are "protected hydroxy," and "protected hydroxymethyl" which refer to a hydroxy or hydroxymethyl substituted with one of the above hydroxy-protecting groups.

The term "$C_1$ to $C_{10}$ alkylthio" refers to sulfide groups such as methylthio, ethylthio, n-propylthio, isopropylthio, n-butylthio, t-butylthio and like groups. The term "$C_1$ to $C_{10}$ alkylsulfoxide" indicates sulfoxide groups such as methylsulfoxide, ethylsulfoxide, n-propylsulfoxide, isopropylsulfoxide, n-butylsulfoxide sec-butylsulfoxide and the like. The term "$C_1$ to $C_{10}$ alkylsulfonyl" encompasses groups such as methylsulfonyl, ethylsulfonyl, n-propylsulfonyl, isopropylsulfonyl, n-butylsulfonyl, t-butylsulfonyl and the like. it should also be understood that the above thio, sulfoxide or sulfonyl groups can be at any point on the alkyl chain (e.g., 2-methylmercaptoethyl).

The terms "$C_1$ to $C_{10}$ substituted alkylthio," "$C_1$ to $C_{10}$ substituted alkylsulfoxide," and "$C_1$ to $C_{10}$ substituted alkylsulfonyl," denote the $C_1$ to $C_{10}$ alkyl portion of these groups may be substituted as described above in relation to "substituted alkyl."

The terms "phenylthio," "phenylsulfoxide," and "phenylsulfonyl" specify a thiol, a sulfoxide, or sulfone, respectively, containing a phenyl group. The terms "substituted phenylthio," "substituted phenylsulfoxide," and "substituted phenylsulfonyl" means that the phenyl of these groups can be substituted as described above in relation to "substituted phenyl."

The term "$C_1$ to $C_{12}$ alkylaminocarbonyl" means a $C_1$ to $C_{12}$ alkyl attached to a nitrogen of the aminocarbonyl group. Examples of $C_1$ to $C_{12}$ alkylaminocarbonyl include methylaminocarbonyl, ethylaminocarbonyl, propylaminocarbonyl and butylaminocarbonyl. The term "$C_1$ to $C_{12}$ substituted alkylaminocarbonyl" denotes a substituted alkyl bonded to a nitrogen of the aminocarbonyl group, which alkyl may be substituted as described above in relation to $C_1$ to $C_{12}$ substituted alkyl. Examples of $C_1$ to $C_{12}$ substituted alkylaminocarbonyl include, for example, methoxymethylaminocarbonyl, 2-chloroethylaminocarbonyl, 2-oxopropylaminocarbonyl and 4-phenylbutylaminocarbonyl.

The term "$C_1$ to $C_{12}$ alkoxycarbonyl" means a "$C_1$ to $C_{12}$ alkoxy" group attached to a carbonyl group. The term "$C_1$ to $C_{12}$ substituted alkoxycarbonyl" denotes a substituted alkoxy bonded to the carbonyl group, which alkoxy may be substituted as described above in relation to "$C_1$ to $C_{12}$ substituted alkyl."

The term "phenylaminocarbonyl" means a phenyl attached to a nitrogen of the aminocarbonyl group. The term "substituted phenylaminocarbonyl" denotes a substituted phenyl bonded to a nitrogen of the aminocarbonyl group, which phenyl may be substituted as described above in relation to substituted phenyl. Examples of substituted phenylaminocarbonyl include 2-chlorophenylaminocarbonyl, 3-chlorophenylaminocarbonyl, 2-nitorphenylaminocarbonyl, 4-biphenylaminocarbonyl, and 4-methoxyphenylaminocarbonyl.

The term "$C_1$ to $C_{12}$ alkylaminothiocarbonyl" means a $C_1$ to $C_{12}$ alkyl attached to an aminothiocarbonyl group, wherein the alkyl has the same meaning as defined above. Examples of $C_1$ to $C_{12}$ alkylaminothiocarbonyl include methylaminothiocarbonyl, ethylaminothiocarbonyl, propylaminothiocarbonyl and butylaminothiocarbonyl.

The term "$C_1$ to $C_{12}$ substituted alkylaminothiocarbonyl" denotes a substituted alkyl bonded to an aminothiocarbonyl group, wherein the alkyl may be substituted as described above in relation to $C_1$ to $C_{12}$ substituted alkyl. Examples of $C_1$ to $C_{12}$ substituted alkylaminothiocarbonyl include, for example, methoxymethylaminothiocarbonyl, 2-chloroethylaminothiocarbonyl, 2-oxopropylaminothiocarbonyl and 4-phenylbutylaminothiocarbonyl.

The term "phenylaminothiocarbonyl" means a phenyl attached to an aminothiocarbonyl group, wherein the phenyl has the same meaning as defined above.

The term "substituted phenylaminothiocarbonyl" denotes a substituted phenyl bonded to an aminothiocarbonyl group, wherein phenyl may be substituted as described above in relation to substituted phenyl. Examples of substituted phenylaminothiocarbonyls include 2-chlorophenylaminothiocarbonyl, 3-chlorophenylaminothiocarbonyl, 2nitorphenylaminothiocarbonyl, 4-biphenylaminothiocarbonyl and 4-methoxyphenylaminothiocarbonyl.

The term "phenylene" means a phenyl group where the phenyl radical is bonded at two positions connecting together two separate additional groups. Examples of "phenylene" include 1,2-phenylene, 1,3-phenylene, and 1,4-phenylene.

The term "substituted phenylene" means a phenyl group where the phenyl radical is bonded at two positions connecting together two separate additional groups, wherein the phenyl is substituted as described above in relation to "substituted phenyl."

The term "substituted $C_1$ to $C_{12}$ alkylene" means a $C_1$ to $C_{12}$ alkyl group where the alkyl radical is bonded at two positions connecting together two separate additional groups and further bearing an additional substituent. Examples of "substituted $C_1$ to $C_{12}$ alkylene" includes aminomethylene, 1-(amino) -1,2-ethyl, 2-(amino)-1,2-ethyl, 1-(acetamido)-1, 2-ethyl, 2-(acetamido)-1,2-ethyl, 2-hydroxy-1,1-ethyl, 1-(amino) -1,3-propyl.

The terms "Cyclic $C_2$ to $C_7$ alkylene," "substituted cyclic $C_2$ to $C_7$ alkylene," "cyclic $C_2$ to $C_7$ heteroalkylene," and "substituted cyclic $C_2$ to $C_7$ heteroalkylene," defines such a cyclic group bonded ("fused") to the phenyl radical resulting in a bicyclic ring system. The cyclic group may be saturated or contain one or two double bonds. Furthermore, the cyclic group may have one or two methylene or methine groups replaced by one or two oxygen, nitrogen or sulfur atoms which are the cyclic $C_2$ to $C_7$ heteroalkylene.

The cyclic alkylene or heteroalkylene group may be substituted once or twice by the same or different substituents which, if appropriate, can be connected to another part of the compound (e.g., alkylene) selected from the group consisting of the following moieties: hydroxy, protected hydroxy, carboxy, protected carboxy, oxo, protected oxo, $C_1$ to $C_4$ acyloxy, formyl, $C_1$ to $C_{12}$ acyl, $C_1$ to $C_{12}$ alkyl, $C_1$ to $C_7$ alkoxy, $C_1$ to $C_{10}$ alkylthio, $C_1$ to $C_{10}$ alkylsulfoxide, $C_1$ to $C_{10}$ alkylsulfonyl, halo, amino, protected amino, (monosubstituted)amino, protected (monosubstituted) amino, (disubstituted)amino, hydroxymethyl or a protected hydroxymethyl.

The cyclic alkylene or heteroalkylene group fused onto the benzene radical can contain two to ten ring members, but it preferably contains three to six members. Examples of such saturated cyclic groups are when the resultant bicyclic ring system is 2,3-dihydroindanyl and a tetralin ring. When the cyclic groups are unsaturated, examples occur when the resultant bicyclic ring system is a naphthyl ring or indolyl. Examples of fused cyclic groups which each contain one nitrogen atom and one or more double bond, preferably one or two double bonds, are when the benzene radical is fused to a pyridino, pyrano, pyrrolo, pyridinyl, dihydropyrrolo, or dihydropyridinyl ring. Examples of fused cyclic groups which each contain one oxygen atom and one or two double bonds are when the benzene radical ring is fused to a furo, pyrano, dihydrofurano, or dihydropyrano ring. Examples of fused cyclic groups which each have one sulfur atom and contain one or two double bonds are when the benzene radical is fused to a thieno, thiopyrano, dihydrothieno or dihydrothiopyrano ring. Examples of cyclic groups which contain two heteroatoms selected from sulfur and nitrogen and one or two double bonds are when the benzene radical ring is fused to a thiazolo, isothiazolo, dihydrothiazolo or dihydroisothiazolo ring. Examples of cyclic groups which contain two heteroatoms selected from oxygen and nitrogen and one or two double bonds are when the benzene ring is fused to an oxazolo, isoxazolo, dihydrooxazolo or dihydroisoxazolo ring. Examples of cyclic groups which contain two nitrogen heteroatoms and one or two double bonds occur when the benzene ring is fused to a pyrazolo, imidazolo, dihydropyrazolo or dihydroimidazolo ring or pyrazinyl.

The term "carbamoyl" means an —NCO— group where the radical is bonded at two positions connecting two separate additional groups.

One or more of the compounds of the invention, even within a given library, may be present as a salt. The term "salt" encompasses those salts that form with the carboxylate anions and amine nitrogens and include salts formed with the organic and inorganic anions and cations discussed below. Furthermore, the term includes salts that form by standard acid-base reactions with basic groups (such as amino groups) and organic or inorganic acids. Such acids include hydrochloric, hydrofluoric, trifluoroacetic, sulfuric, phosphoric, acetic, succinic, citric, lactic, maleic, fumaric, palmitic, cholic, pamoic, mucic, D-glutamic, D-camphoric, glutaric, phthalic, tartaric, lauric, stearic, salicyclic, methanesulfonic, benzenesulfonic, sorbic, picric, benzoic, cinnamic, and like acids.

The term "organic or inorganic cation" refers to counterions for the carboxylate anion of a carboxylate salt. The counter-ions are chosen from the alkali and alkaline earth metals, (such as lithium, sodium, potassium, barium, aluminum and calcium); ammonium and mono-, di- and tri-alkyl amines such as trimethylamine, cyclohexylamine; and the organic cations, such as dibenzylammonium, benzylammonium, 2-hydroxyethylammonium, bis(2-hydroxyethyl)ammonium, phenylethylbenzylammonium, dibenzylethylenediammonium, and like cations. See, for example, "Pharmaceutical Salts," Berge et al., J. Pharm. Sci., 66:1–19 (1977), which is incorporated herein by reference. Other cations encompassed by the above term include the protonated form of procaine, quinine and N-methylglucosamine, and the protonated forms of basic amino acids such as glycine, ornithine, histidine, phenylglycine, lysine and arginine. Furthermore, any zwitterionic form of the instant compounds formed by a carboxylic acid and an amino group is referred to by this term. For example, a cation for a carboxylate anion will exist when a position is substituted with a (quaternary ammonium)methyl group. A preferred cation for the carboxylate anion is the sodium cation.

The compounds of the invention can also exist as solvates and hydrates. Thus, these compounds may crystallize with, for example, waters of hydration, or one, a number of, or any fraction thereof of molecules of the mother liquor solvent. The solvates and hydrates of such compounds are included within the scope of this invention.

One or more compounds of the invention, even when in a library, can be in the biologically active ester form, such as the non-toxic, metabolically-labile ester-form. Such ester forms induce increased blood levels and prolong the efficacy of the corresponding non-esterified forms of the compounds. Ester groups which can be used include the lower alkoxymethyl groups, for example, methoxymethyl, ethoxymethyl, isopropoxymethyl and the like; the —($C_1$ to $C_{12}$) alkoxyethyl groups, for example methoxyethyl, ethoxyethyl, propoxyethyl, isopropoxyethyl and the like; the 2-oxo-1,3-diooxlen-4-ylmethyl groups, such as 5-methyl-2-oxo-1,3-dioxolen-4-ylmethyl, 5-phenyl-2-oxo-1,3-dioxolen-4-ylmethyl and the like; the $C_1$ to $C_{10}$ alkylthiomethyl groups, for example methylthiomethyl, ethylthiomethyl, isopropylthiomethyl and the like; the acyloxymethyl groups, for example pivaloyloxymethyl, pivaloyloxyethyl, -acetoxymethyl and the like; the ethoxycarbonyl-1-methyl group; the -acetoxyethyl; the 1-($C_1$ to $C_{12}$ alkyloxycarbonyloxy)ethyl groups such as the 1-(ethoxycarbonyloxy)ethyl group; and the 1-($C_1$ to $C_{12}$ alkylaminocarbonyloxy)ethyl groups such as the 1-(methylaminocarbonyloxy)ethyl group.

The term "amino acid" includes any one of the twenty naturally-occurring amino acids or the D-form of any one of the naturally-occurring amino acids. In addition, the term "amino acid" also includes other non-naturally occurring amino acids besides the D-amino acids, which are functional equivalents of the naturally-occurring amino acids. Such non-naturally-occurring amino acids include, for example, norleucine ("Nle"), norvaline ("Nva"), L- or D-naphthalanine, ornithine ("Orn"), homoarginine (homoArg) and others well known in the peptide art, such as those described in M. Bodanzsky, "Principles of Peptide Synthesis," 1st and 2nd revised ed., Springer-Verlag, New York, N.Y., 1984 and 1993, and Stewart and Young, "Solid Phase Peptide Synthesis," 2nd ed., Pierce Chemical Co., Rockford, Ill., 1984, both of which are incorporated herein by reference. Amino acids and amino acid analogs can be purchased commercially (Sigma Chemical Co.; Advanced Chemtech) or synthesized using methods known in the art.

The term "functionalized resin" means any resin, crosslinked or otherwise, where functional groups have been introduced into the resin, as is common in the art. Such resins include, for example, those functionalized with amino, alkylhalo, formyl or hydroxy groups. Such resins which can serve as solid supports are well known in the art and include, for example, 4-methylbenzhydrylamine-copoly (styrene-1% divinylbenzene) (MBHA), 4-hydroxymethylphenoxymethyl-copoly(styrene-1% divinylbenzene), 4-oxymethyl-phenyl-acetamido-copoly (stryene-1% divinylbenzene)(Wang), 4-(oxymethyl)-phenylacetamido methyl (Pam), and Tentagel™, from Rapp Polymere Gmbh, trialkoxy-diphenyl-methyl ester-copoly (styrene-1% divinylbenzene)(RINK) all of which are commercially available. Other functionalized resins are known in the art and can be use without departure from the scope of the current invention. Such resins may include those described in Jung, G., Combinatorial Peptide and Nonpeptide Libraries, A Handbook (VCH Verlag, 1996) or Bunin, B.

A., The Combinatorial Index (Academic Press, 1998) and are incorporated herein by reference.

As used herein, a "combinatorial library" is an intentionally created collection of differing molecules which can be prepared by the means provided below or otherwise and screened for biological activity in a variety of formats (e.g., libraries of soluble molecules, libraries of compounds attached to resin beads, silica chips or other solid supports). A "combinatorial library," as defined above, involves successive rounds of chemical syntheses based on a common starting structure. The combinatorial libraries can be screened in any variety of assays, such as those detailed below as well as others useful for assessing their biological activity. The combinatorial libraries will generally have at least one active compound and are generally prepared such that the compounds are in equimolar quantities.

Compounds disclosed in previous work that are not disclosed as part of a collection of compounds or not disclosed as intended for use as part of such a collection are not part of a "combinatorial library" of the invention. In addition, compounds that are in an unintentional or undesired mixture are not part of a "combinatorial library" of the invention.

A combinatorial library of the invention can contain two or more of the above-described compounds. The invention further provides a combinatorial library containing three, four or five or more of the above-described compounds. In another embodiment of the invention, a combinatorial library can contain ten or more of the above-described compounds. In yet another embodiment of the invention, a combinatorial library can contain fifty or more of the above-described compounds. If desired, a combinatorial library of the invention can contain 100,000 or more, or even 1,000,000 or more, of the above-described compounds.

By way of example, the preparation of the combinatorial libraries can use the "split resin approach." The split resin approach is described by, for example, U.S. Pat. No. 5,010,175 to Rutter, WO PCT 91/19735 to Simon, and Gallop et al., *J. Med. Chem.*, 37:1233–1251 (1994), all of which are incorporated herein by reference.

The amino acids are indicated herein by either their full name or by the commonly known three letter code. Further, in the naming of amino acids, "D-" designates an amino acid having the "D" configuration, as opposed to the naturally occurring L-amino acids. Where no specific configuration is indicated, one skilled in the art would understand the amino acid to be an L-amino acid. The amino acids can, however, also be in racemic mixtures of the D- and L-configuration or the D-amino acid can readily be substituted for that in the L-configuration.

For preparing pharmaceutical compositions containing compounds of the invention, inert, pharmaceutically acceptable carriers are used. The pharmaceutical carrier can be either solid or liquid. Solid form preparations include, for example, powders, tablets, dispersible granules, capsules, cachets, and suppositories.

A solid carrier can be one or more substances which can also act as diluents, flavoring agents, solubilizers, lubricants, suspending agents, binders, or tablet disintegrating agents; it can also be an encapsulating material.

In powders, the carrier is generally a finely divided solid which is in a mixture with the finely divided active component. In tablets, the active compound is mixed with the carrier having the necessary binding properties in suitable proportions and compacted in the shape and size desired.

For preparing pharmaceutical composition in the form of suppositories, a low-melting wax such as a mixture of fatty acid glycerides and cocoa butter is first melted and the active ingredient is dispersed therein by, for example, stirring. The molten homogeneous mixture is then poured into convenient-sized molds and allowed to cool and solidify.

Powders and tablets preferably contain between about 5% to about 70% by weight of the active ingredient. Suitable carriers include, for example, magnesium carbonate, magnesium stearate, talc, lactose, sugar, pectin, dextrin, starch, tragacanth, methyl cellulose, sodium carboxymethyl cellulose, a low-melting wax, cocoa butter and the like.

The pharmaceutical compositions can include the formulation of the active compound with encapsulating material as a carrier providing a capsule in which the active component (with or without other carriers) is surrounded by a carrier, which is thus in association with it. In a similar manner, cachets are also included. Tablets, powders, cachets, and capsules can be used as solid dosage forms suitable for oral administration.

Liquid pharmaceutical compositions include, for example, solutions suitable for oral or parenteral administration, or suspensions, and emulsions suitable for oral administration. Sterile water solutions of the active component or sterile solutions of the active component in solvents comprising water, ethanol, or propylene glycol are examples of liquid compositions suitable for parenteral administration.

Sterile solutions can be prepared by dissolving the active component in the desired solvent system, and then passing the resulting solution through a membrane filter to sterilize it or, alternatively, by dissolving the sterile compound in a previously sterilized solvent under sterile conditions.

Aqueous solutions for oral administration can be prepared by dissolving the active compound in water and adding suitable flavorants, coloring agents, stabilizers, and thickening agents as desired. Aqueous suspensions for oral use can be made by dispersing the finely divided active component in water together with a viscous material such as natural or synthetic gums, resins, methyl cellulose, sodium carboxymethyl cellulose, and other suspending agents known to the pharmaceutical formulation art.

Preferably, the pharmaceutical composition is in unit dosage form. In such form, the composition is divided into unit doses containing appropriate quantities of the active tetracyclic benzimidazole compound. The unit dosage form can be a packaged preparation, the package containing discrete quantities of the preparation, for example, packeted tablets, capsules, and powders in vials or ampules. The unit dosage form can also be a capsule, cachet, or tablet itself, or it can be the appropriate number of any of these packaged forms.

As pharmaceutical compositions for treating infections, pain, or any other indication the compounds of the present invention are generally in a pharmaceutical composition so as to be administered to a subject at dosage levels of from 0.7 to 7000 mg per day, and preferably 1 to 500 mg per day, for a normal human adult of approximately 70 kg of body weight, this translates into a dosage of from 0.01 to 100 mg/kg of body weight per day. The specific dosages employed, however, can be varied depending upon the requirements of the patient, the severity of the condition being treated, and the activity of the compound being employed. The determination of optimum dosages for a particular situation is within the skill of the art.

The compounds of and combinatorial libraries of the invention can be prepared as set forth in FIG. 1 and as described below.

Variant tetracyclic benzimidazole derivative compounds and combinatorial libraries can be prepared in order to achieve a high level of diversity. For instance, a protected amino acid can be coupled to amine compound and then deprotected, resulting in a carboxamido substituted amino compound having a substituent of the formula —NH—C(O)—C(variable group)—NH$_2$ (see step 1 of FIG. 1).

The amine compound can be attached to solid support, such as a functionalized resin (e.g., methylbenzhydrylamine (MBHA).

The carboxamido substituted amino compound can then be coupled to a phenyl compound with a nitro and a halo group at ortho positions, resulting in a phenyl compound substituted with a nitro group and a monosubstituted amino group. The phenyl compound being coupled can also have one to four additional substituents, such as carboxyl, halo, alkyl, etc. (see steps 2 and 3 of FIG. 1).

Where the phenyl compound also has a carboxyl substituent, this substituent can be reacted with a (i) monosubstituted amine; (ii) disubstituted amine; (iii) cyclic imide; or (iv) alcohol; resulting, respectively, in a (i) monosubstituted carboxamido substituent; (ii) disubstituted carboxamido substituent; (iii) cyclic imido carbonyl substituent; or (iv) ester substituent attached to the phenyl compound (see step 4 of FIG. 1). It should be understood that such a substituent can be at any one to four of the available positions on the phenyl ring.

The nitro group of the phenyl compound can be reduced (see step 5 of FIG. 1). The resulting compound can be coupled with a phenyl compound that is substituted with an aldehyde group and a nitro group at meta positions on the phenyl ring, resulting in a phenyl substituted benzimidazole derivative compound having a nitro substituted phenyl substituent (see step 6 of FIG. 1). The phenyl compound that is substituted with an aldehyde group and a nitro group can also be substituted with one to four leaving groups at the one to four remaining positions on the phenyl ring (see, for example, the fluoro group of the phenyl compound between steps 5 and 6 of FIG. 1).

Where the phenyl group has a leaving group, it can be reacted with a monosubstituted amine, a disubstituted amine, a monosubstituted thiol and an alcohol, resulting, respectively, in a monosubstituted amino, disubstituted amino, monosubstituted thio or ether moiety on the phenyl ring (see step 7 of FIG. 1).

The nitro group of the benzimidazole derivative compound (see step 6) can be reduced, resulting in a tetracyclic benzimidazole derivative compound (see steps 8 and 9 of FIG. 1). In addition, the imino group in the resulting seven-member ring can be substituted. For example, the imino group can be alkylated with an alkyl halide or substituted alkyl halide.

Resin-bound tetracyclic benzimidazole derivative compounds can be cleaved by treating them, for example, with HF gas (see Example 1, Step 6; and steps 7 to 8 of FIG. 1). The compounds can then be extracted from the spent resin, for example, with AcOH (see Example Example 1, Step 6).

Tetracyclic benzimidazole derivative compounds and libraries, such as those of the present invention, can be made utilizing individual polyethylene bags, referred to as "tea bags" (see Houghten et al., *Proc. Natl. Acad. Sci. USA* 82: 5131 (1985); *Biochemistry*, 32:11035 (1993); and U.S. Pat. No. 4,631,211, all of which are incorporated herein by reference).

The nonsupport-bound combinatorial libraries can be screened as single compounds. In addition, the nonsupport-bound combinatorial libraries can be screened as mixtures in solution in assays such as radio-receptor inhibition assays, anti-bacterial assays, anti-fungal assays, calmodulin-dependent phosphodiesterase (CaMPDE) assays and phosphodiesterase (PDE) assays, as described in detail below. Deconvolution of highly active mixtures can then be carried out by iterative or positional scanning methods. These techniques, the iterative approach or the positional scanning approach, can be utilized for finding other active compounds within the combinatorial libraries of the present invention using any one of the below-described assays or others well known in the art.

The iterative approach is well-known and is set forth in general in Houghten et al., *Nature*, 354, 84–86 (1991) and Dooley et al., *Science*, 266, 2019–2022 (1994), both of which are incorporated herein by reference. In the iterative approach, for example, sub-libraries of a molecule having three variable groups are made wherein the first variable is defined. Each of the compounds with the defined variable group is reacted with all of the other possibilities at the other two variable groups. These sub-libraries are each tested to define the identity of the second variable in the sub-library having the highest activity in the screen of choice. A new sub-library with the first two variable positions defined is reacted again with all the other possibilities at the remaining undefined variable position. As before, the identity of the third variable position in the sub-library having the highest activity is determined. If more variables exist, this process is repeated for all variables, yielding the compound with each variable contributing to the highest desired activity in the screening process. Promising compounds from this process can then be synthesized on larger scale in traditional single-compound synthetic methods for further biological investigation.

The positional-scanning approach has been described for various combinatorial libraries as described, for example, in R. Houghten et al. PCT/US91/08694 and U.S. Pat. No. 5,556,762, both of which are incorporated herein by reference. In the positional scanning approach, sublibraries are made defining only one variable with each set of sublibraries and all possible sublibraries with each single variable defined (and all other possibilities at all of the other variable positions), made and tested. From the instant description one skilled in the art could synthesize combinatorial libraries wherein two fixed positions are defined at a time. From the testing of each single-variable defined combinatorial library, the optimum substituent at that position can be determined, pointing to the optimum or at least a series of compounds having a maximum of the desired biological activity. Thus, the number of sublibraries for compounds with a single position defined will be the number of different substituents desired at that position, and the number of all the compounds in each sublibrary will be the product of the number of substituents at each of the other variables.

Individual compounds and pharmaceutical compositions containing the compounds, as well as methods of using the same, are included within the scope of the present invention. The compounds of the present invention can be used for a variety of purposes and indications and as medicaments for any such purposes and indications. For example, tetracyclic benzimidazole derivative compounds of the present invention can be used as pesticides, acaricides, receptor agonists or antagonists and antimicrobial agents, including antibacterial or antiviral agents. For example, the libraries can be screened in any variety of melanocortin receptor and related activity assays, such as those detailed below as well as others known in the art. Additionally, the subject compounds can be useful as analgesics. Assays which can be used to test the biological activity of the instant compounds include antimicrobial assays, a competitive enzyme-linked immunoabsorbent assay and radio-receptor assays, as described below.

The melanocortin (MC) receptors are a group of cell surface proteins that mediate a variety of physiological effects, including regulation of adrenal gland function such as production of the glucocorticoids cortisol and aldosterone; control of melanocyte growth and pigment production; thermoregulation; immunomodulation; and analgesia. Five distinct MC receptors have been cloned and are expressed in a variety of tissues, including melanocytes, adrenal cortex, brain, gut, placenta, skeletal muscle, lung, spleen, thymus, bone marrow, pituitary, gonads and adipose tissue (Tatro, *Neuroimmunomodulation* 3:259–284 (1996)). Three MC receptors, MCR-1, MCR-3 and MCR-4, are expressed in brain tissue (Xia et al., *Neuroreport* 6:2193–2196 (1995)).

A variety of ligands termed melanocortins function as agonists that stimulate the activity of MC receptors. The melanocortins include melanocyte-stimulating hormones (MSH) such as α-MSH, β-MSH and γ-MSH, as well as adrenocorticotropic hormone (ACTH). Individual ligands can bind to multiple MC receptors with differing relative affinities. The variety of ligands and MC receptors with differential tissue-specific expression likely provides the molecular basis for the diverse physiological effects of melanocortins and MC receptors. For example, α-MSH antagonizes the actions of immunological substances such as cytokines and acts to modulate fever, inflammation and immune responses (Catania and Lipton, *Annals N. Y. Acad. Sci.* 680:412–423 (1993)).

The role of certain specific MC receptors in some of the physiological effects described above for MC receptors has been elucidated. For example, MCR-1 is involved in pain and inflammation. MCR-1 mRNA is expressed in neutrophils (Catania et al., *Peptides* 17:675–679 (1996)). The anti-inflammatory agent α-MSH was found to inhibit migration of neutrophils. Thus, the presence of MCR-1 in neutrophils correlates with the anti-inflammatory activity of α-MSH.

An interesting link of MC receptors to regulation of food intake and obesity has recently been described. The brain MC receptor MCR-4 has been shown to function in the regulation of body weight and food intake. Mice in which MCR-4 has been knocked out exhibit weight gain (Huszar et al., *Cell* 88:131–141 (1997)). In addition, injection into brain of synthetic peptides that mimic melanocortins and bind to MCR-4 caused suppressed feeding in normal and mutant obese mice (Fan et al., *Nature* 385:165–168 (1997)). These results indicate that the brain MC receptor MCR-4 functions in regulating food intake and body weight.

Due to the varied physiological activities of MC receptors, high affinity ligands of MC receptors could be used to exploit the varied physiological responses of MC receptors by functioning as potential therapeutic agents or as lead compounds for the development of therapeutic agents. Furthermore, due to the effect of MC receptors on the activity of various cytokines, high affinity MC receptor ligands could also be used to regulate cytokine activity.

A variety of assays can be used to identify or characterize MC receptor ligands of the invention. For example, the ability of a tetracyclic benzimidazole derivative compound to compete for binding of a known MC receptor ligand can be used to assess the affinity and specificity of a tetracyclic benzimidazole compound for one or more MC receptors. Any MC receptor ligand can be used so long as the ligand can be labeled with a detectable moiety. The detectable moiety can be, for example, a radiolabel, fluorescent label or chromophore, or any detectable functional moiety so long as the MC receptor ligand exhibits specific MC receptor binding. A particularly useful detectable MC receptor ligand for identifying and characterizing other MC receptor ligands is $^{125}$I-HP 467, which has the amino acid sequence Ac-Nle-Gln-His-(p(I)-D-Phe)-Arg-(D-Trp)-Gly-NH$_2$ and is described in Dooley et al., "Melanocortin Receptor Ligands and Methods of Using Same," U.S. patent application Ser. No. 09/027,108, U.S. Pat. No. 6,350,430 filed Feb. 20, 1998, which is incorporated herein by reference. HP 467 is a para-iodinated form of HP 228.

Using assay methods such as those described above, binding kinetics and competition with radiolabeled HP 467 can confirm that tetracyclic benzimidazole compounds of the invention bind to one or more MC receptors. Furthermore, tetracyclic benzimidazole derivative compounds of the invention can exhibit a range of affinities and specificity for various MC receptors.

The invention provides MC receptor ligands that can bind to several MC receptors with similar affinity. In addition, the invention also provides MC receptor ligands that can be selective for one or more MC receptors. As used herein, the term "selective" means that the affinity of a MC receptor ligand differs between one MC receptor and another by about 10-fold, generally about 20- to 50-fold, and particularly about 100-fold. In some cases, a MC receptor ligand having broad specificity is desired. In other cases, it is desirable to use MC receptor ligands having selectivity for a particular MC receptor. For example, MCR-1 ligands are particularly useful for treating pain and inflammation, whereas MCR-4 ligands are useful for treating obesity. The binding characteristics and specificity of a given MC receptor ligand can be selected based on the particular disease or physiological effect that is desired to be altered.

Another assay useful for identifying or characterizing MC receptor ligands measures signaling of MC receptors. MC receptors are G protein-coupled receptors that couple to adenylate cyclase and produce cAMP. Therefore, measuring cAMP production in a cell expressing a MC receptor and treated with a MC receptor ligand can be used to assess the function of the MC receptor ligand in activating a MC receptor.

Ligands for MC-3 that can alter the activity of an MC-3 receptor can be useful for treating sexual dysfunction and other conditions or conditions associated with MC-3 such as inflammation. Other MC-3-associated conditions that can be treated with the MC-3 receptor ligands include disuse deconditioning; organ damage such as organ transplantation or ischemic injury; adverse reactions associated with cancer chemotherapy; diseases such as atherosclerosis that are mediated by free radicals and nitric oxide action; bacterial endotoxic sepsis and related shock; adult respiratory distress syndrome; and autoimmune or other patho-immunogenic diseases or reactions such as allergic reactions or anaphylaxis, rheumatoid arthritis, inflammatory bowel disease, ulcerative colitis, glomerulonephritis, systemic lupus erythematosus, transplant atherosclerosis and parasitic mediated immune dysfunctions such as Chagas's Disease.

The invention further provides a method for treating an MC-3-associated condition in a subject. The term "MC-3-associated condition" includes any condition or condition mediated by MC-3 or can be affected by binding an MC-3 ligand. Such conditions include inflammation and sexual dysfunction.

The term "sexual dysfunction" herein means any condition that inhibits or impairs normal sexual function, including coitus. However, the term need not be limited to physiological conditions, but may include psychogenic conditions or perceived impairment without a formal diagnosis of pathology.

In males, sexual dysfunction includes erectile dysfunction. The term "erectile dysfunction" or "impotence" means herein the inability or impaired ability to attain or sustain an erection that would be of satisfactory rigidity for coitus. Sexual dysfunction in males can also include premature ejaculation and priapism, which is a condition of prolonged and sometimes painful erection unrelated to sexual activity, often associated with sickle-cell disease.

In females, sexual dysfunction includes sexual arousal disorder. The term "sexual arousal disorder" means herein a persistent or recurrent failure to attain or maintain the lubrication-swelling response of sexual excitement until completion of sexual activity. Sexual dysfunction in females can also include inhibited orgasm and dyspareunia, which is painful or difficult coitus. Sexual dysfunction can also be manifested as inhibited sexual desire or inhibited lordosis behavior in animals.

In addition, the ability of the compounds to inhibit bacterial growth, and therefore be useful to that infection, can be determined by methods well known in the art. Compounds of the present invention were shown to have antimicrobial activity by the in vitro antimicrobial activity assay described below and, therefore, are useful as antimicrobial agents (see Example 16).

In addition, an exemplary in vitro antimicrobial activity assay is described in Blondelle and Houghten, *Biochemistry* 30:4671–4678 (1991), which is incorporated herein by reference. In brief, *Staphylococcus aureus* ATCC 29213 (Rockville, Md.) is grown overnight at 37° C. in Mueller-Hinton broth, then re-inoculated and incubated at 37° C. to reach the exponential phase of bacterial growth (i.e., a final bacterial suspension containing $10^5$ to $5 \times 10^5$ colony-forming units/ml). The concentration of cells is established by plating 100 μl of the culture solution using serial dilutions (e.g., $10^{-2}$, $10^{-3}$ and $10^{-4}$) onto solid agar plates. In 96-well tissue culture plates, compounds, individual or in mixtures, are added to the bacterial suspension at concentrations derived from serial two-fold dilutions ranging from 1500 to 2.9 μg/ml. The plates are incubated overnight at 37° C. and the growth determined at each concentration by $OD_{620}$ nm. The $IC_{50}$ (the concentration necessary to inhibit 50% of the growth of the bacteria) can then be calculated.

The competitive ELISA method which can be used here is a modification of the direct ELISA technique described previously in Appel et al., *J. Immunol.* 144:976–983 (1990), which is incorporated herein by reference. It differs only in the MAb addition step. Briefly, multi-well microplates are coated with the antigenic peptide (Ac-GASPYPNLSNQQT-NH$_2$) at a concentration of 100 pmol/50 μl. After blocking, 25 μl of a 1.0 mg/ml solution of each mixture of a synthetic combinatorial library (or individual compound) is added, followed by MAb 125-10F3 (Appel et al., supra) (25 μl per well). The MAb is added at a fixed dilution in which the bicyclic guanidine in solution effectively competes for MAb binding with the antigenic peptide adsorbed to the plate. The remaining steps are the same as for direct ELISA. The concentration of compound necessary to inhibit 50% of the MAb binding to the control peptide on the plate ($IC_{50}$) is determined by serial dilutions of the compound.

Alternative screening can be done with radio-receptor assays. The radio-receptor assay, can be selective for any one of the μ, κ, or δ opiate receptors. Compounds of the present invention can be useful in vitro for the diagnosis of relevant opioid receptor subtypes, such as κ, in the brain and other tissue samples. Similarly, the compounds can be used in vivo diagnostically to localize opioid receptor subtypes.

The radio-receptor assays are also an indication of the compounds' analgesic properties as described, for example, in Dooley et al., *Proc. Natl. Acad. Sci.*, 90:10811–10815 (1993). For example, it can be envisioned that these compounds can be used for therapeutic purposes to block the peripheral effects of a centrally acting pain killer. For instance, morphine is a centrally acting pain killer. Morphine, however, has a number of deleterious effects in the periphery which are not required for the desired analgesic effects, such as constipation and pruritus (itching). While it is known that the many compounds do not readily cross the blood-brain barrier and, therefore, elicit no central effect, the subject compounds can have value in blocking the periphery effects of morphine, such as constipation and pruritus. Accordingly, the subject compounds can also be useful as drugs, namely as analgesics, or to treat pathologies associated with other compounds which interact with the opioid receptor system.

Additionally, such compounds can be tested in a σ receptor assay. Ligands for the σ receptor can be useful as antipsychotic agents, as described in Abou-Gharbia et al., *Annual Reports in Medicinal Chemistry*, 28:1–10 (1993).

Radio-receptor assays can be performed with particulate membranes prepared using a modification of the method described in Pasternak et al., *Mol. Pharmacol.* 11:340–351 (1975), which is incorporated herein by reference. Rat brains frozen in liquid nitrogen can be obtained from Rockland (Gilbertsville, Pa.). The brains are thawed, the cerebella removed and the remaining tissue weighed. Each brain is individually homogenized in 40 ml Tris-HCl buffer (50 mM, pH 7.4, 4° C.) and centrifuged (Sorvallo® RC5C SA-600: Du Pont, Wilmington, Del.) (16,000 rpm) for 10 minutes. The pellets are resuspended in fresh Tris-HCl buffer and incubated at 37° C. for 40 minutes. Following incubation, the suspensions are centrifuged as before, the resulting pellets resuspended in 100 volumes of Tris buffer and the suspensions combined. Membrane suspensions are prepared and used in the same day. Protein content of the crude homogenates generally range from 0.15–0.2 mg/ml as determined using the method described in Bradford, M. M., *Anal. Biochem.* 72:248–254 (1976), which is incorporated herein by reference.

Binding assays are carried out in polypropylene tubes, each tube containing 0.5 ml of membrane suspension. 8 nM of $^3$H-[D-Ala$^2$,Me-Phe$^4$,Gly-ol$^5$]enkephalin (DAMGO) (specific activity=36 Ci/mmol, 160,000 cpm per tube; which can be obtained from Multiple Peptide Systems, San Diego, Calif., through NIDA drug distribution program 271-90-7302) and 80 μg/ml of bicyclic guanidine, individual or as a mixture and Tris-HCl buffer in a total volume of 0.65 ml. Assay tubes are incubated for 60 mins. at 25° C. The reaction is terminated by filtration through GF-B filters on a Tomtec harvester (Orange, Conn.). The filters are subsequently washed with 6 ml of Tris-HCl buffer, 4° C. Bound radioactivity is counted on a Pharmacia Biotech Betaplate Liquid Scintillation Counter (Piscataway, N.J.) and expressed in cpm. To determine inter- and intra-assay variation, standard curves in which $^3$H-DAMGO is incubated in the presence of a range of concentrations of unlabeled DAMGO (0.13–3900 nM) are generally included in each plate of each assay (a 96-well format). Competitive inhibition assays are performed as above using serial dilutions of the bicyclic guanidines, individually or in mixtures. $IC_{50}$ values (the concentration necessary to inhibit 50% of $^3$H-DAMGO binding) are then calculated. $IC_{50}$ values of less than 1000 nM are indicative of highly active opioid compounds which bind to the μ receptor, with particularly active compounds having $IC_{50}$ values of 100 nM or less and the most active compounds with values of less than 10 nM.

As opposed to this μ receptor selective assay, which can be carried out using ³H-DAMGO as radioligand, as described above, assays selective for κ receptors can be carried out using [³H]-U69,593 (3 nM, specific activity 62 Ci/mmol) as radioligand. Assays selective for δ opiate receptors can be carried out using tritiated DSLET ([D-Ser², D-Leu⁵]-threonine-enkephalin) as radioligand. Assays selective for the a opiate receptor can use radiolabeled pentazocine as ligand.

Screening of combinatorial libraries and compounds of the invention can be done with an anti-fungal assay. Compounds of the present invention can be useful for treating fungal infections.

Screening of combinatorial libraries and compounds of the invention also can be done with a calmodulin-dependent phosphodiesterase (CaMPDE) assay. Compounds of the present invention can be useful as calmodulin antagonists.

Calmodulin (CaM), which is the major intracellular calcium receptor, is involved in many processes that are crucial to cellular viability. In particular, calmodulin is implicated in calcium-stimulated cell proliferation. Calmodulin antagonists are, therefore, useful for treating conditions associated with increased cell proliferation, for example, cancer. In addition, calmodulin antagonists such as compounds of the subject invention are useful both in vitro and in vivo for identifying the role of calmodulin in other biological processes. The disadvantages of known antagonists such as trifluoperazine and N-(4-aminobutyl)-5-chloro-2-naphthalenesulfonamide (W13) include their non-specificity and toxicity. In contrast, advantages of the combinatorial libraries and compounds of the subject invention as calmodulin antagonists include their reduced flexibility and ability to generate broader conformational space of interactive residues as compared to their linear counterparts.

An example of an assay that identifies CaM antagonists is a CaMPDE assay. In brief, samples are mixed with 50 μl of assay buffer (360 mM Tris, 360 mM Imidazole, 45 mM Mg(CH₃COO)₂, pH 7.5) and 10 μl of CaCl₂ (4.5 mM) to a final volume of 251 μl. 25 μl of calmodulin stock solution (Boehringer Mannheim; 0.01 μg/pl) is then added and the samples then sit at room temperature for 10 minutes. 14 μl of PDE (Sigma; 2 Units dissolved in 4 ml of water; stock concentration: 0.0005 Units/μl) is then added, followed by 50 μl of 5'-nucleotidase (Sigma; 100 Units dissolved in 10 ml of 10 mM Tris-HCl containing 0.5 mM Mg(CH₃COO)₂, pH 7.0; stock concentration: 10 Units/ml). The samples are then incubated for 10 minutes at 30° C. 50 μl of adenosine 3',5'-cyclic monophosphate (cAMP) (20 mM in water at pH 7.0) is added, the samples incubated for 1 hour at 30° C. and then vortexed. 200 μl of trichloroacetic acid (TCA) (55% in water) is added to a 200 μl sample aliquot, which is then vortexed and centrifuged for 10 minutes. 80 μl of the resulting supernatants of each sample is transferred to a 96-well plate, with 2 wells each containing 80 μl of each sample. 80 μl of ammonium molybdate (1.1% in 1.1N H₂SO₄) is then added to all the wells, and the OD of each were determined at 730 nm, with the values later subtracted to the final OD reading. 16 μl of reducing agent (6 g sodium bisulfite, 0.6 g sodium sulfite and 125 mg of 1-amino-2-naphtol-4-sulfonic acid in 50 ml of water) is then added to one of each sample duplicate and 16 μl of water is added to the other duplicate. After sitting for 1 hour at room temperature, the OD of each well is determined at 730 nm. The percent inhibition of calmodulin activity is then calculated for each sample, using as 0% inhibition a control sample containing all reagents without any test samples and as 100% inhibition a control sample containing test samples and all reagents except calmodulin. In addition, the percent inhibition of phosphodiesterase activity was determined by following a similar protocol as the CaMPDE assay described above, except not adding calmodulin to the sample mixture and calculating the percent inhibition by using as 0% inhibition a control reagent without any test samples and as 100% inhibition a control sample containing test samples and all reagents except cAMP.

The following examples are provided to illustrate but not limit the present invention. In the examples, the following abreviations have the corresponding meanings:
MBHA: 4-methylbenzhydrylamine;
DMF: dimethylforamide;
HoBt: 1-hydroxybenzotriazole;
DMSO: dimethylsulfoxide;
Boc: tert-butoxycarbonyl;
FMOC: 9-fluorenyl-methoxycarbonyl;
DMAP: 4-dimethylamino-pyridine;
DIC: N,N'-diisopropylcarbodiimide;
TFA: trifluoroacetic acid;
DIEA: diisopropylethylamine;
DCM: dichloromethane;
TMOF: trimethylorthoformate;
HATU: azabenzotriazolyl-N,N,N',N'-tetramethyluronium hexafluorophosphate;

EXAMPLE 1

Preparation of a Combinatorial Library of 70 Tetracyclic Bezimidazole Derivative Compounds (pyrrolidinyl 7-phenylmethyl-2-substituted-5H-benzimidazol[1,2,d][1,4]benzodiazepin-6(7H)-one-10-Carboxamides)

This example describes 70 substituted amino variations at the $R^7$ position, the side chain of phenylalanine (Ph—CH₂) providing the $R^1$ position, pyrrolidinocarbonyl at the $R^4$ position and hydrogen at the remaining R positions.

Step 1

Coupling of N-protected Amino Acid to MBHA Resin 1.0 g of MBHA resin (1.3 meq/g) was placed in a porous polypropylene packet (Tea-bag, 60 mm×60mm, 65μ). The packet was washed with 5% DIEA/DCM (2×60 mL) in a 65 mL plastic bottle. DMF (40 mL), Boc-phenylalanine (3.45 g, 13 mmol), DIC (2.52 g, 20 mmol), HOBt (1.75 g, 13 mmol) were added sequentially. After shaking for 12 hours, the packet was washed alternatively with DMF (40 mL) and MeOH (40 m L) for 3 cycles followed by DCM (40 mL) and MeOH (40 mL). The packet was dried in air for 1 h. The packet was shaken with 55% TFA/DCM (40 mL) at room temperature for 40 minutes and washed with DCM (3×40 mL), 5% DIEA/DCM (2×40 mL) and MeOH (3×40 mL).

Step 2

N-Arylation with 4-fluoro-3-nitrobenzoic Acid

The packet resulting from the reaction described in step 1 was heated in a solution of 4-fluoro-3-nitrobenzoic acid (2.40 g, 13 mmol) and DIEA (1.64 g, 13 mmol) in N-methylpyrrolidinone (40 mL) at 70° C. for 24 hours. The packet was washed alternatively with DMF (40 mL) and MeOH (40 mL) for 3 cycles followed by washing with DCM (40 mL) and MeOH (2×40 mL). The packet was dried in air for 2 hours.

Step 3

Coupling Pyrrolidine

The packet resulting from the reaction described in step 2 was shaken with a solution of pyrrolidine (0.92 g, 13 mmol), DIC (2.52 g, 20 mmol) and HOBt (1.75 g, 13 mmol) in DMF (40 mL) for 24 hours. The packet was washed alternatively with DMF (40 mL) and MeOH (40 mL) for 3 cycles followed by DCM (40 mL) and MeOH (2×40 mL). The packet was dried in air for 2 hours.

Step 4

Reduction of the Nitro Group to Amine

The packet resulting from the reaction described in step 3 was shaken with a 2.0 M solution of tin(II) chloride dihydrate in N-Methylpyrrolidinone (40 mL) for 24 hours at room temperature. The packet was washed with DMF (6×40 mL), 10% DIEA/DCM (4×40 mL), MeOH, (2×40 mL), DMF (40 mL), MeOH (40 mL), DCM (2×40 mL) and MeOH (2×40 mL) and dried in air for 2 hours.

Step 5

Reaction with Aldehyde to Form Benzimidazole

The packet resulting from the reaction described in step 4 was heated in a solution of 5-fluoro-2-nitrobenzaldehyde (2.21 g, 13 mmol) in N-methylpyrrolidinone (20 mL) and acetic acid (20 mL) at 70° C. for 72 hours. The packet was washed alternatively with DMF (40 mL) and MeOH (40 mL) for 3 cycles followed by washing with DCM (40 mL) and MeOH (2×40 mL). The packet was dried in air for 2 hours.

Step 6

Displacement of Fluoro Substituent by One of 70 Amines

The packet resulting from the reaction described in step 5 was cut open and the resin was suspended in N-methylpyrrolidinone (30 mL). The suspension was distributed equally into 70 wells of a microtiter plate (2 mL×96). One of 70 amines in N-methylpyrrolidinone (100 μL×1.0 M) were added to each well. The plate was tightly capped, shaken and incubated at 75° C. for 72 hours. The resin was washed alternatively with DMF (3×1 mL/well) and MeOH (2×1 mL/well) for 5 cycles and MeOH (5×1 mL/well). The plate was dried in air for two days and under vacuum for 4 hours. To cleave the resulting compounds, the plate was treated with gaseous HF at room temperature for 2 hours. After complete removal of HF under a nitrogen stream followed by vacuum, the plate was extracted with AcOH (4×0.5 mL/well). The extractions were then lyophilized. The 70 amines were as follows:

1-(2-furoyl)-piperazine
1-(2-pyridyl)piperazine
1-(4-fluorophenyl)piperazine
piperazine
N-acetylethylenediamine
ethylenediamine
ethyl isonipecotate
N-(3-aminopropyl)morpholine
3-(trifluoromethyl)benzylamine
cyclohexylamine
p-xylylenediamine
1-methyl-4-(methylamino)piperidine
1-(ethoxycarbonylmethyl)piperazine
β-alanine ethylester
N-(2-aminoethyl)morpholine
cyclooctylamine
3-fluorophenethylamine
2-fluorophenethylamine
N-(3-trifluoromethylphenyl)piperazine
3,3,5-trimethylcyclohexylamine
1-benzylpiperazine
ethyl nipecotate
2-(2-methylaminoethyl)pyridine
2-(2-aminoethyl)pyridine
4-amino-1-benzylpiperidine
1,8-diamino-3,6-dioxaoctane
tyramine
N,N-dimethylethylenediamine
N-methylphenethylamine
diethylamine
4-(trifluoromethyl)benzylamine
2-(aminomethyl)-1-ethylpyrrolidine
N,N-dimethyl-1,3-propanediamine
N,N,N'-trimethyl-1,3-propanediamine
3,3'-bis(dimethylamino)-dipropylamine
1-(4-nitrophenyl)-piperazine
4-piperazinoacetophenone
3-(aminomethyl)pyridine
ethyl 4-amino-1-piperidinecarboxylate
thiomorpholine
m-xylylenediamine
N,N-diethyl-2-butene-1,4-diamine
1-(4-methoxyphenyl)-2-methylpiperazine
N-(3,4-dichlorophenyl)piperazine
tetrahydrofurfurylamine
1-acetylpiperazine
1,3-diaminopropane
2,3-dimethoxybenzylamine
2-methyl-1-(3-methylphenyl)piperazine
1,3,3-trimethyl-6-azabicyclo[3.2.1]octane
1-(5-chloro-ortho-tolyl)-piperazine
hexamethyleneimine
cycloheptylamine
3-acetamidopyrrolidine
1-benzyl-3-aminopyrrolidine
1-(2-aminoethyl)piperidine
1-ethoxycarbonylpiperazine
4-amino-2,2,6,6-tetramethylpiperidine
N-methylbenzylamine
2-ethoxyethylamine
3-(methylthio)propylamine
4-fluorobenzylamine
butylamine
isonipecotamide
N,N-diethyl-n'-methylethylenediamine
1-(3-aminopropyl)-2-pipecoline
morpholine
1-(2,5-dimethylphenyl)piperazine
1-(2,3-dimethylphenyl)-piperazine
cyclopropylamine

EXAMPLE 2

Preparation of a Combinatorial Library of 83 Tetracyclic Benzimidazole Derivative Compounds (bis(methoxyethyl)amino 7-(3-Indolylmethyl)-2-substituted-5H-benzimidazol[1,2,d][1,4]benzodiazepin-6(7H)-one-10-carboxamides)

Using the same experimental procedures as described in Example 1, an additional combinatorial library of 83 tetracyclic benzimidazole derivative compounds were synthesized. This example describes 83 substituted amino variations at the $R^7$ position, the side chain of tryptophan providing the $R^1$ position, bis(methoxyethyl)aminocarbonyl at the $R^4$ position and hydrogen at the remaining R positions. The 83 amines used were as follows:
1-(2-furoyl)piperazine
1-(2-pyridyl)piperazine
1-(4-fluorophenyl)piperazine
piperazine
N-acetylethylenediamine
ethylenediamine
tryptamine
ethyl isonipecotate
ethanolamine
4-(3-aminopropyl)morpholine
p-phenylenediamine
3-(trifluoromethyl)benzylamine
N-ethylmethylamine
cyclohexylamine
p-xylylenediamine
1-methyl-4-(methylamino)piperidine
1-(ethoxycarbonylmethyl)piperazine
beta alanine-ethyl ester
4-(2-aminoethyl)morpholine
cyclooctylamine
3-fluorophenethylamine
2-fluorophenethylamine
N-(3-trifluoromethylphenyl)piperazine
3,3,5-trimethylcyclohexylamine
1-benzylpiperazine
ethyl nipecotate
2-(2-methylaminoethyl)pyridine
2-(2-aminoethyl)pyridine
4-amino-1-benzylpiperidine
decahydroquinoline
trans-1,4-diaminocyclohexane
4-methoxybenzylamine
2,2-(ethylenedioxy)bis(ethylamine)
tyramine
N,N-dimethylethylenediamine
N-methylphenethylamine
diethylamine
2-(aminomethyl)-1-ethylpyrrolidine
3-dimethylaminopropylamine
N,N,N'-trimethyl-1,3-propanediamine
3,3'-bis(dimethylamino)-dipropylamine
1-(4-nitrophenyl)piperazine
4-piperazinoacetophenone
3-(aminomethyl)pyridine
2-(aminomethyl)pyridine
ethyl 4-amino-1-piperidinecarboxylate
thiomorpholine
m-xylylenediamine
N,N-diethyl-2-butene-1,4-diamine
N-methyl-N-propylamine
N-butylbenzylamine
1-(4-methoxyphenyl)-2-methylpiperazine
N-(3,4-dichlorophenyl)piperazine
tetrahydrofurfurylamine
1-acetylpiperazine
1,3-diaminopropane
2,3-dimethoxybenzylamine
2-methyl-1-(3-methylphenyl)piperazine
1,3,3-trimethyl-6-azabicyclo(3.2.1)octane
1-(5-chloro-ortho-tolyl)-piperazine
hexamethyleneimine
N,N,N'-trimethylethylenediamine
cycloheptylamine
3-acetamidopyrrolidine
1-benzyl-3-aminopyrrolidine
bis(2-methoxyethyl)amine
N-(2-aminoethyl)piperadine
ethyl 1-piperazine carboxylate
4-amino-2,2,6,6-tetramethylpiperadine
N-benzylmethylamine
2-ethoxyethylamine
3-(2-ethylhexyloxy)propylamine
3-methylthiopropylamine
4-fluorobenzylamine
cyclopentylamine
ethyl 4-amino-1-piperidinecarboxylate
pyrrolidine
butylamine
isonipecotamide
N,N-diethyl-N'-methylethylenediamine
1-(3-aminopropyl)-2-pipecoline
bis(3-aminopropyl)ether
cyclopropylamine

EXAMPLE 3

Preparation of a Combinatorial Library of Tetracyclic Benzimidazole Derivative Compounds (pyrrolidinyl 7-Phenylmethyl-2-substituted-5H-benzimidazol[1,2,d][1,4]b enzodiazepin-6(7H)-one-10-carboxamides)

Using the same experimental procedures as described in Example 1, an additional combinatorial library of 8 tetracyclic benzimidazole derivative compounds were synthesized. This example describes 8 substituted thio variations at the $R^7$ position, the side chain of phenylalanine providing the $R^1$ position, pyrrolidinocarbonyl at the $R^4$ position and hydrogen at the remaining R positions. The 8 thiols used were as follows:
5-phenyl-1H-1,2,4-triazole-3-thiol
6-mercaptonicotinic acid
2-mercaptoimidazole
4-6-dimethyl-2-mercaptopyrimidine
2-mercapto-5-methyl-1,3,4-thiadiazole
3-mercapto-1,2,4-triazole
3-mercapto-4-methyl-1,2,4-triazole
2-mercaptopyridine

EXAMPLE 4

Preparation of a Combinatorial Library of Tetracyclic Benzimidazole Derivative Compounds (1'-Ethylpyrrolidino-2'-methylamino 2-Morpholino-7-substituted-5H-benzimidazol[1,2,d][1,4]ben zodiazepin-6(7H)-one-10-carboxamides)

Using the same experimental procedures as described in Example 1, an additional combinatorial library of 15 tetracyclic benzimidazole derivative compounds were synthesized. This example describes the side chain of 15 different amino acids providing the $R^1$ position, 2-(aminomethyl)-1-ethylpyrrolidinocarbonyl at the $R^4$ position, 1-morpholino at the $R^7$ position and hydrogen at the remaining R positions. The 15 amino acids used were as follows:
Boc-glycine
Boc-L-alanine
Boc-L-valine
Boc-L-isoleucine
Boc-L-glutamine Boc-L-methionine
Boc-L-phenylglycine
Boc-L-phenylalanine
Boc-D-phenylalanine
Boc-L-cyclohexylalanine
Boc-O-methyl-L-tyrosine
Boc-4-chloro-L-phenylalanine
Boc-$N^{in}$-formal-L-tryptophan
$N^\alpha$-Boc-Nε-trifluoroacetyl-L-lysine
$N^\alpha$-Boc-$N^g$-4-tosyl-L-arginine

EXAMPLE 5

Preparation of a Combinatorial Library of Tetracyclic Benzimidazole Derivative Compounds (4'-(2-Furoyl)piperazinyl 2-Morpholino-7-substituted-5H-benzimidazol[1,2,d][1,4]ben zodiazepin-6(7H)-one-10-carboxamides)

Using the same experimental procedures as described in Example 1, an additional combinatorial library of 15 tetracyclic benzimidazole derivative compounds were synthesized. This example describes the side chain of 15 different amino acids providing the $R^1$ position, 1-(2-furoyl)piperazinocarbonyl at the $R^4$ position, 1-morpholino at the $R^7$ position and hydrogen at the remaining R positions. The 15 amino acids used were as follows:
Boc-glycine
Boc-L-alanine
Boc-L-valine
Boc-L-isoleucine
Boc-L-glutamine
Boc-L-methionine
Boc-L-phenylglycine
Boc-L-phenylalanine
Boc-D-phenylalanine
Boc-L-cyclohexylalanine
Boc-O-methyl-L-tyrosine
Boc-4-chloro-L-phenylalanine
Boc-$N^{in}$-formal-L-tryptophan
$N^\alpha$-Boc-$N^\epsilon$-trifluoroacetyl-L-lysine
$N^\alpha$-Boc-$N^g$-4-tosyl-L-arginine

EXAMPLE 6

Preparation of a Combinatorial Library of Tetracyclic Benzimidazole Derivative Compounds (2-Morpholino-7-phenylmethyl-5H-benzimidazol[1,2,d][1,4]benzodiazepin-6(7H)-one-10-carboxamides)

Using the same experimental procedures as described in Example 1, an additional combinatorial library of 43 tetracyclic benzimidazole derivative compounds were synthesized. This example describes 43 substituted amino variations as building blocks for the $R^4$ position, the side chain of L-phenylalanine providing the $R^1$ position, 1-morpholino at the $R^7$ position and hydrogen at the remaining R positions. The 43 amines used were as follows:
2-(aminomethyl)-1-ethylpyrrolidine
2-aminothiazole
methyl 6-aminocaproate
beta-alanine ethyl ester
pyrrolidine
N-methylhomopiperazine
1-(4-fluorophenyl)piperazine
1-hydroxyethylethoxypiperazine
3-(methylthio)aniline
1-(2-pyridyl)piperazine
1-methyl-4-(methylamino)piperidine
2-(2-aminoethyl)pyridine
4-hydroxypiperidine
2-ethanolamine
4-(trifluoromethyl)benzylamine
4-amino-2,2,6,6-tetramethylpiperidine
ethyl nipecotate
1-(4-methoxyphenyl)-2-methylpiperazine
N,N-dimethylethylenediamine
1-(3-aminopropyl)-2-pyrrolidinone
isonipecotamide
ethyl 4-amino-1-piperidinecarboxylate
heptamethyleneimine
2-(aminomethyl)pyridine
1-(2-furoyl)-piperazine
bis(2-methoxyethyl)amine
N-(3-trifluoromethylphenyl)piperazine
3-acetamidopyrrolidine
1-ethoxycarbonylpiperazine
N-acetylethylenediamine
N-(2-aminoethyl)morpholine
5-aminoindazole
cyclopropylamine
4-(ethylaminomethyl)pyridine
cyclopentylamine
cycloheptylamine
3-(aminomethyl)pyridine
3-(trifluoromethyl)benzylamine
ethyl isonipecotate
thiomorpholine
thiophene-2-ethylamine
1-pyrrolidinepropanamine
N-(3-aminopropyl)imidazole

EXAMPLE 7

Preparation of a Combinatorial Library of Tetracyclic Benzimidazole Derivative Compounds (2-Morpholino-7-aminocarbonylethyl-5H-benzimidazol[1,2,d][1,4]benzodiazepin-6(7H)-one-10-carboxamides)

Using the same experimental procedures as described in Example 1, an additional combinatorial library of 40 tetracyclic benzimidazole derivative compounds were synthesized. This example describes 40 substituted amino variations used as building blocks for the $R^4$ position, the side chain of L-glutamine providing the $R^1$ position, 1-morpholino at the $R^7$ position and hydrogen at the remaining R positions. The 40 amines used were as follows:
2-(aminomethyl)-1-ethylpyrrolidine
2-aminothiazole
methyl 6-aminocaproate hydrochloride
beta-alanine ethyl ester hydrochloride
pyrrolidine
N-methylhomopiperazine
1-(4-fluorophenyl)piperazine
3-(methylthio)aniline
1-(2-pyridyl)piperazine
1-methyl-4-(methylamino)piperidine
2-(2-aminoethyl)pyridine
4-hydroxypiperidine
4-amino-2,2,6,6-tetramethylpiperidine
ethyl nipecotate
1-(4-methoxyphenyl)-2-methylpiperazine
N,N-dimethylethylenediamine
1-(3-aminopropyl)-2-pyrrolidinone
isonipecotamide
ethyl 4-amino-1-piperidinecarboxylate heptamethyleneimine
2-(aminomethyl)pyridine
1-(2-furoyl)-piperazine
bis(2-methoxyethyl)amine
N-(3-trifluoromethylphenyl)piperazine
3-acetamidopyrrolidine
1-ethoxycarbonylpiperazine
N-acetylethylenediamine
N-(2-aminoethyl)morpholine
5-aminoindazole
cyclopropylamine
4-(ethylaminomethyl)pyridine
cyclopentylamine
cycloheptylamine
3-(aminomethyl)pyridine
3-(trifluoromethyl)benzylamine
ethyl isonipecotate
thiomorpholine
thiophene-2-ethylamine
1-pyrrolidinepropanamine
N-(3-aminopropyl)imidazole

EXAMPLE 8

Preparation of a Combinatorial Library of Tetracyclic Benzimidazole Derivative Compounds (9- or 10-Substituted-2-morpholino-7-phenylmethyl-5H-benzimidazol[1,2,d][1,4]benzodiazepin-6(7H)-one)

This example describes 7 variations at the 9- or 10-position of the tetracyclic benzimidazole derivative compounds, with 7 different 2-fluoronitrobenzene compounds providing the $R^3$ or $R^4$ positions, the side chain of phenylalanine providing the $R^1$ position, 1-morpholino at the $R^7$ position and hydrogen at the remaining R positions.

Step 1

Coupling N-protected Amino Acid to MBHA Resin 1.0 g of MBHA resin (1.3 meq/g) was placed in a porous polypropylene packet (Tea-bag, 60 mm×60 mm, 65µ). The packet was washed with 5% DIEA/DCM (2×60 mL) in a 65 mL plastic bottle. DMF (40 mL), BOC-phenylalanine (3.45 g, 13 mmol), DIC (2.52 g, 20 mmol), HOBt (1.75 g, 13 mmol) were added sequentially. After shaking for 12 hours, the packet was washed alternatively with DMF (40 mL) and MeOH (40 mL) 3 cycles followed by DCM (40 mL) and MeOH (40 mL). The packet was dried in air for 1 h. The packet was shaken with 55% TFA/DCM (40 mL) at room temperature for 40 minutes and washed with DCM (3×40 mL), 5% DIEA/DCM (2×40 mL) and MeOH (3×40 mL).

Step 2

N-Arylation with Substituted or Unsubstituted 2-fluoronitrobenze

The packet resulting from step 1 was heated in a solution of a 2-fluoronitrobenzoic acid (2.40 g, 13 mmol) and DIEA (1.64 g, 13 mmol) in N-methylpyrrolidinone (40 mL) at 80° C. for 24 hours. The packet was washed alternatively with DMF (40 mL) and MeOH (40 mL) for 3 cycles followed by washing with DCM (40 mL) and MeOH (2×40 mL). The packet was dried in air for 2 hours. The 7 2-fluoronitrobenzoic acids used were as follows:
4-fluoro-3-nitrobenzoic acid
5-bromo-2-fluoronitrobenzene
2-fluoronitrobenzene
2,5-difluoronitrobenzene
4-fluoro-3-nitrobenzotrifluoride
3-fluoro-4-nitrotoluene
4-chloro-2-fluoronitrobenzene The resulting compounds were then prepared by following steps 4 to 6, as described in Example 1.

EXAMPLE 9

Preparation of a Combinatorial Library of Tetracyclic Benzimidazole Derivative Compounds (9- or 10-Substituted-2-morpholino-7-aminocarbonylethyl-5H-benzimidazol[1,2,d][1,4]benzodiazepin-6(7H)-one)

Using the procedures described in Example 8, this example describes 7 variations at the 9- or 10-position of the tetracyclic benzimidazole derivative compounds, with 7 different 2-fluoronitrobenzene compounds providing the $R^3$ or $R^4$ positions, the side chain of glutamine providing the $R^1$ position, 1-morpholino at the $R^7$ position and hydrogen at the remaining R positions. The 7 2-fluoronitrobenzoic acids used were as follows:
4-fluoro-3-nitrobenzoic acid
5-bromo-2-fluoronitrobenzene
2-fluoronitrobenzene
2,5-difluoronitrobenzene
4-fluoro-3-nitrobenzotrifluoride
3-fluoro-4-nitrotoluene
4-chloro-2-fluoronitrobenzene The resulting compounds were then prepared by following steps 4 to 6, as described in Example 1.

EXAMPLE 10

Preparation of a Combinatorial Library of 61,200 Tetracyclic Benzimidazole Derivative Compounds Using the same experimental procedures described above, an additional combinatorial library of 61,200 (15×51×80) tetracyclic benzimidazole derivative compounds were synthesized. The side chain of any one of the 15 amino acids listed in Examples 4 and 5 provided the $R^1$ position. The 43 amines listed in Example 6 plus 3-(methylthio)propylamine and the 7 different 2-nitrofluorobenzene compounds listed in Examples 8 and 9 provided the 51 building blocks at the $R^4$ or $R^3$ position. The following 80 compounds provided the building blocks at the $R^7$ position:
cyclopropylamine
4-(2-aminoethyl)morpholine
piperazine
2-methyl-1-(3-methylphenyl)piperazine
isonipecotamide
2-(2-aminoethyl)pyridine
N,N-dimethylethylenediamine
m-xylylenediamine
5-phenyl-1H-1,2,4-triazole-3-thiol
4-(3-aminopropyl)morpholine
tetrahydrofurfurylamine
1-(2,5-dimethylphenyl)piperazine
hexamethyleneimine
2-(2-methylaminoethyl)pyridine
N,N,N'-trimethylethylenediamine
p-xylylenediamine
6-mercaptonicotinic acid
N-acetylethylenediamine
β-alanine-ethyl ester
1-(2,3-dimethylphenyl)piperazine 1-(2-pyridyl)piperazine
1-(3-aminopropyl)-2-pipecoline
ethylenediamine
cyclcohexylamine
2-mercaptoimidazole
ethyl 1-piperazine carboxylate
3-methylthiopropylamine
1-(4-fluorophenyl)piperazine
1-benzyl-3-aminopyrrolidine
1-methyl-4-(methylamino)piperidine
1,3-diaminopropane
N-benzylmethylamine
4-6-dimethyl-2-mercaptopyrimidine
1-acetylpiperazine
2,3-dimethoxybenzylamine
N-(3,4-dichlorophenyl)piperazine
ethyl nipecotate
3-(aminomethyl)pyridine
N,N-diethyl-N'-methylethylenediamine
N-methylphenethylamine
2-mercapto-5-methyl-1,3,4-thiadiazole
2,2'-(ethylenedioxy)bis(ethylamine)
3-acetamidopyrrolidine
1-benzylpiperazine
ethyl isopecotate
N-(2-aminoethyl)piperidine
3-dimethylaminopropylamine
cycloheptylamine
3-mercapto-1,2,4-triazole
1-(ethoxycarbonylmethyl)piperazine
N,N-diethyl-2-butene-1,4-diamine
1-(4-nitrophenyl)piperazine
ethyl 4-amino-1-piperidinocarboxylate
4-amino-1-benzyl piperidine
N,N,N'-trimethyl-1,3-propanediamine
4-(trifluoromethyl)benzylamine
3-mercapto-4-methyl-1,2,4-triazole
2-ethoxyethylamine
tyramine
N-(3-trifluoromethylphenyl)piperazine
1,3,3-trimethyl-6-azabicyclo(3.2.1)octane
3,3'-bis(dimethylamino)-dipropylamine
butylamine
3-(trifluoromethyl)benzylamine
2-mercaptopyridine
1-(2-furoyl)piperazine
cyclooctylamine
4-piperazinoacetophenone
1-(4-methylphenyl)-2-methylpiperazine
2-fluorophenethylamine
3-fluorophenethylamine
4-fluorobenzylamine
hydrofluoric acid
morpholine
thiomorpholine
1-(5-chloro-ortho-tolyl)-piperazine
2-(aminoethyl)-1-ethylpyrrolidine
4-amino-2,2,6,6-tetramethylpiperidine
diethylamine
3,3,5-trimethylcyclohexylamine

EXAMPLE 11

Melanocortin Receptor Assay

This example describes methods for assaying binding to MC receptors.

All cell culture media and reagents were obtained from GibcoBRL (Gaithersburg Md.), except for COSMIC CALF SERUM (HyClone; Logan Utah). HEK 293 cell lines were transfected with the human MC receptors hMCR-1, hMCR-3, and hMCR-4 (Gantz et al., *Biochem. Biophys. Res. Comm.* 200:1214–1220 (1994); Gantz et al., *J. Biol. Chem.* 268:8246–8250 (1993); Gantz et al. *J. Biol. Chem.* 268:15174–15179 (1993); Haskell-Leuvano et al., *Biochem. Biophys. Res. Comm.* 204:1137–1142 (1994); each of which is incorporated herein by reference). Vectors for construction of an hMCR-5 expressing cell line were obtained, and a line of HEK 293 cells expressing hMCR-5 was constructed (Gantz, supra, 1994). hMCR-5 has been described previously (Franberg et al., *Biochem. Biophys. Res. Commun.* 236:489–492 (1997); Chowdhary et al., *Cytogenet. Cell Genet.* 68:1–2 (1995); Chowdhary et al., *Cytogenet. Cell Genet.* 68:79–81 (1995), each of which is incorporated herein by reference). HEK 293 cells were maintained in DMEM, 25 mM HEPES, 2 mM glutamine, non-essential amino acids, vitamins, sodium pyruvate, 10% COSMIC CALF SERUM, 100 units/ml penicillin, 100 µg/ml streptomycin and 0.2 mg/ml G418 to maintain selection.

Before assaying, cells were washed once with phosphate buffered saline ("PBS"; without $Ca^{2+}$ and $Mg^{2+}$), and stripped from the flasks using 0.25% trypsin and 0.5 mM EDTA. Cells were suspended in PBS, 10% COSMIC CALF SERUM and 1 mM $CaCl_2$. Cell suspensions were prepared at a density of $2\times10^4$ cells/ml for HEK 293 cells expressing hMCR-3, hMCR-4 or hMCR-5, and $1\times10^5$ cells/ml for HEK 293 cells expressing hMCR-1. Suspensions were placed in a water bath and allowed to warm to 37° C. for 1 hr.

Binding assays were performed in a total volume of 250 µl for HEK 293 cells. Control and test compounds were dissolved in distilled water. $^{125}$I-HP 467 (50,000 dpm) (2000 Ci/mmol) (custom labeled by Amersham; Arlington Heights Ill.) was prepared in 50 mM Tris, pH 7.4, 2 mg/ml BSA, 10 mM $CaCl_2$, 5 mM $MgCl_2$, 2 mM EDTA and added to each tube. To each tube was added $4\times10^3$ HEK 293 cells expressing hMCR-3, hMCR-4 or hMCR-5, or $2\times10^4$ cells expressing hMCR-1. Assays were incubated for 2.5 hr at 37° C.

GF/B filter plates were prepared by soaking for at least one hour in 5 mg/ml BSA and 10 mM $CaCl_2$. Assays were filtered using a Brandel 96-well cell harvester (Brandel Inc.; Gaithersburg, Md.). The filters were washed four times with cold 50 mM Tris, pH 7.4, the filter plates were dehydrated for 2 hr and 35 µl of MICROSCINT was added to each well. Filter plates were counted using a Packard Topcount (Packard Instrument Co.) and data analyzed using GraphPad PRISM v2.0 (GraphPad Software Inc.; San Diego Calif.) and Microsoft EXCEL v5.0a (Microsoft Corp.; Redmond Wash.).

To assay tetracyclic benzimidazole derivative compounds, binding assays were performed in duplicate in a 96 well format. HP 467 was prepared in 50 mM Tris, pH 7.4, and $^{125}$I-HP 467 was diluted to give 100,000 dpm per 50 µl. A tetracyclic benzimidazole derivative compound, synthesized as described in Examples 1 to 9, was added to the well in 25 µl aliquots. A 25 µl aliquot of $^{125}$I-HP 467 was added to each well. A 0.2 ml aliquot of suspended cells was added to each well to give the cell numbers indicate above, and the cells were incubated at 37° C. for 2.5 hr. Cells were harvested on GF/B filter plates as described above and counted.

EXAMPLE 12

Anti-microbial Screen

Streptococcus pyogenes (ATCC# 97-03 14289) were grown in Todd Hewitt Broth (THB) (Difco Laboratories

0492-17-6) overnight until they reached an optical density of (OD=0.636@ 570 nm) by reading 0.1 ml in a 96 well microtiter plate in a Molecular Devices Thermomax. This preparation was kept frozen as stocks in 30% v/v glycerol in 1.5 ml aliquots at −70 C° until used. Prior to screening, 1.5 ml aliquots were thawed and diluted into 50 ml THB. 200 μl of this dilution was added to 92 wells of microtiter plate. To three wells THB (200 μl) was added to serve as a blank and a sterility control. Test compounds in DMSO and appropriate concentrations of DMSO were added to Growth/Solvent Controls at 0 time. Plates were read at 0 time at 570 nm in the Molecular Devices plate reader to obtain compounds correction factors for insoluble or colored compounds. Plates were read again at 4 hrs.

Compounds were assayed at a concentration of 170 μg/ml. Percent inhibition for each compound was calculated using the following formulae:

Color correct=(O.D. 0 hr−Blank 0 hr)−(Solvent Control 0 hr−Blank 0 hr)

% Inhibition=100−(O.D. test compound 4 hr−Blank 4 hr−color correct) divided by (O.D. growth/solvent control 4 hr−Blank 4 hr)

Percent inhibition of tetracyclic benzimidazole compounds of the invention are provided in the table below:

| | Sample ID | % Inhibition |
|---|---|---|
| 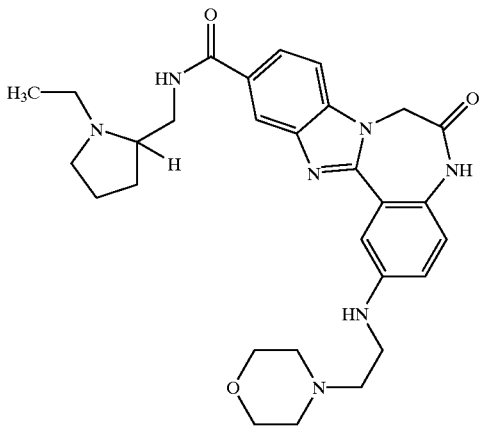 | 6000#00002 | 96.27253571 |
| 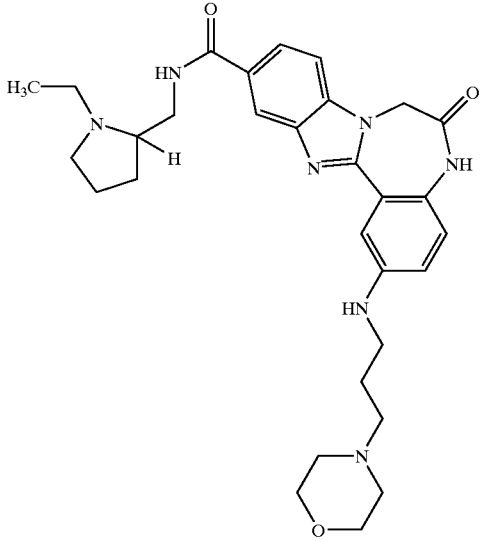 | 6000#00010 | 95.74806837 |

-continued
| Sample ID | % Inhibition |
|---|---|
| 6000#00007 | 95.22360103 |
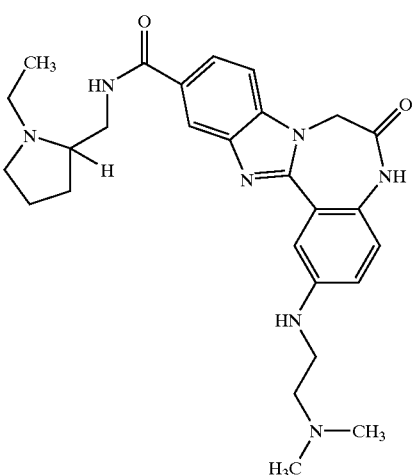
| Sample ID | % Inhibition |
|---|---|
| 6000#00015 | 96.27253571 |
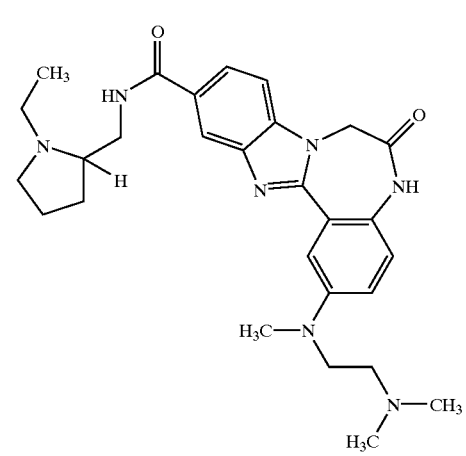
| Sample ID | % Inhibition |
|---|---|
| 6000#04048 | 95.018226 |
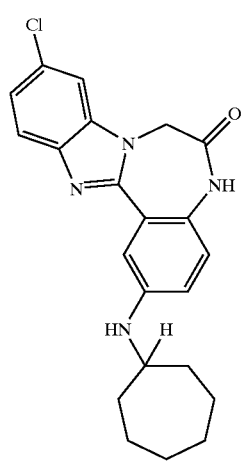

-continued
| | Sample ID | % Inhibition |
|---|---|---|
| 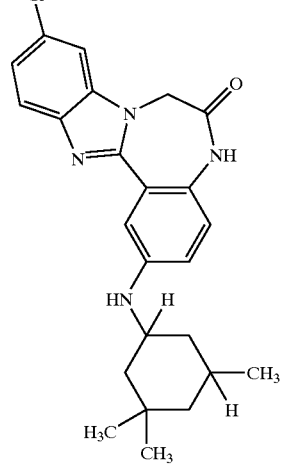 | 6000#04080 | 95.26123937 |
| Chiral 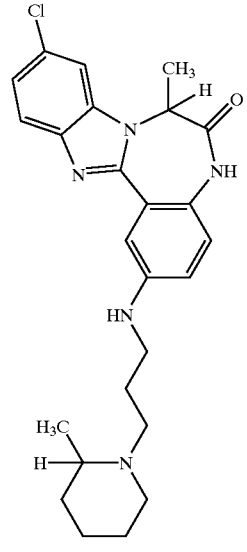 | 6000#08102 | 95.11228534 |
| Chiral 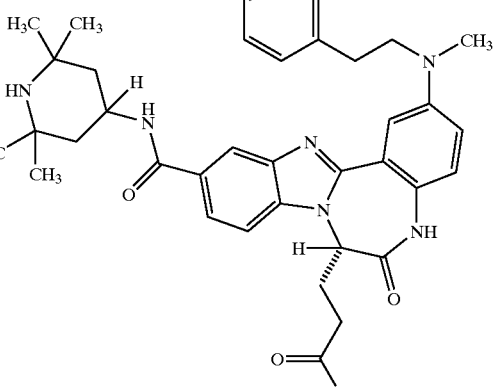 | 6000#17560 | 98.55845466 |

-continued

| | Sample ID | % Inhibition |
|---|---|---|
| Chiral | 6000#17584 | 97.17457114 |
| Chiral | 6000#38375 | 95.0815739 |
| Chiral | 6000#36335 | 100.0474834 |

-continued
| | Sample ID | % Inhibition |
|---|---|---|
| Chiral 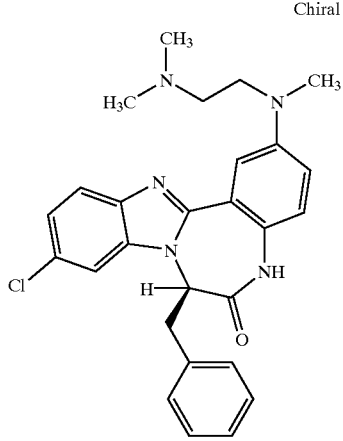 | 6000#36655 | 96.84542587 |
| Chiral 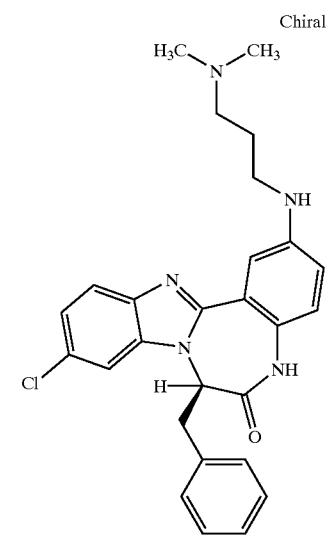 | 6000#36687 | 96.06891531 |
| Chiral 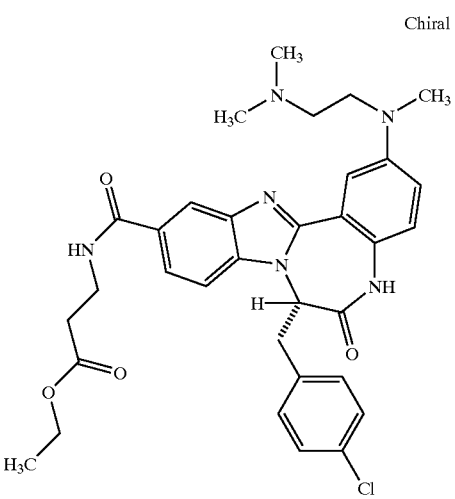 | 6000#45135 | 97.84335982 |

-continued
| | Sample ID | % Inhibition |
|---|---|---|
| Chiral 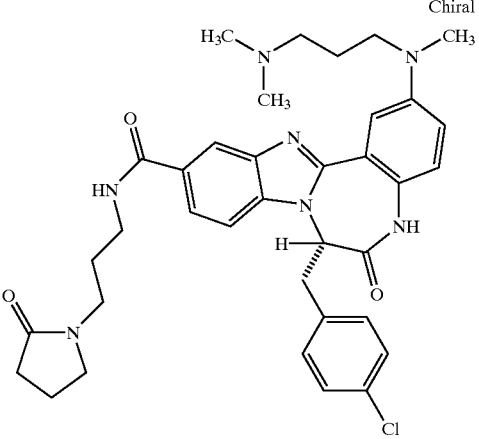 | 6000#46455 | 96.78362573 |
| Chiral 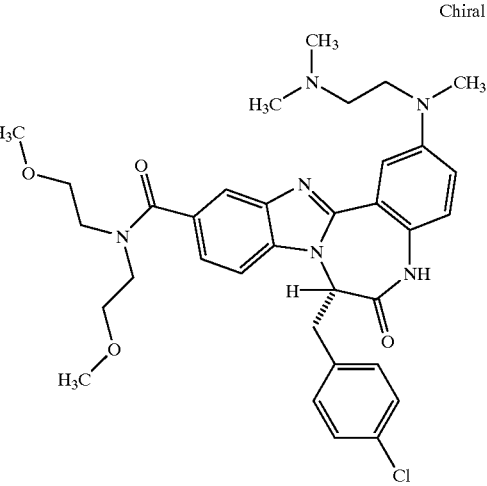 | 6000#46895 | 96.13561794 |
| Chiral 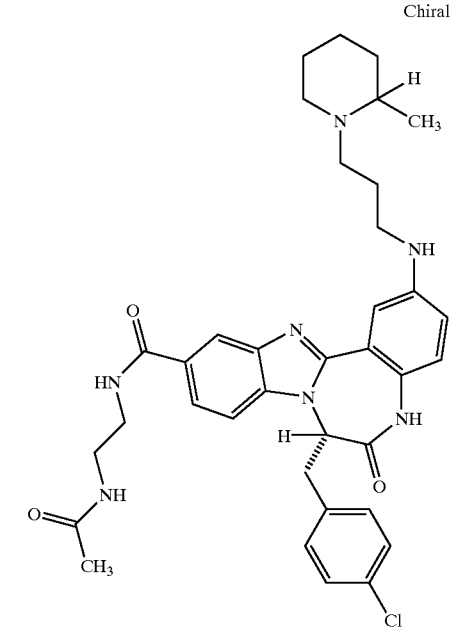 | 6000#47222 | 95.71960298 |

-continued
| | Sample ID | % Inhibition |
|---|---|---|
| 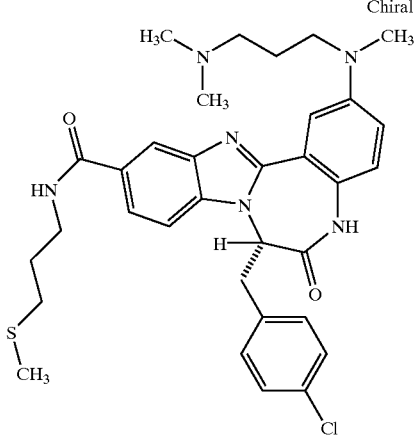 | 6000#47335 | 96.22973925 |
| 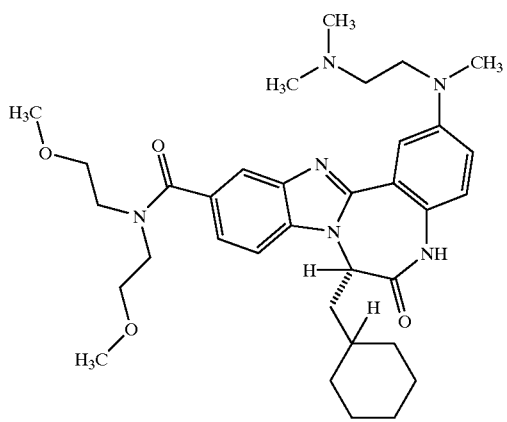 | 6000#38735 | 96.74772036 |
| 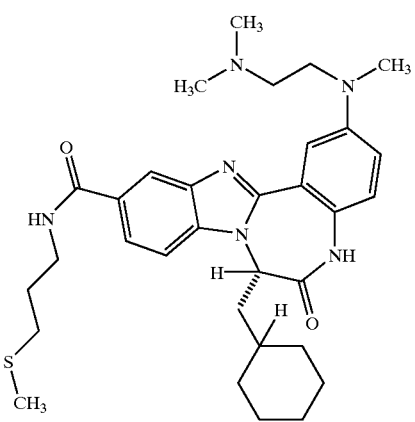 | 6000#39135 | 98.1392557 |

-continued
| | Sample ID | % Inhibition |
|---|---|---|
| 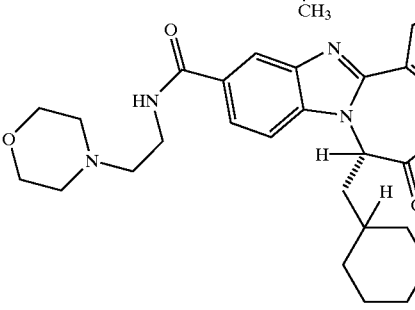 Chiral | 6000#39255 | 95.24831392 |
| 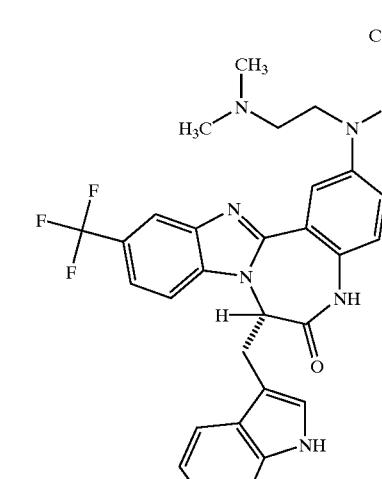 Chiral | 6000#52815 | 98.75111508 |
| 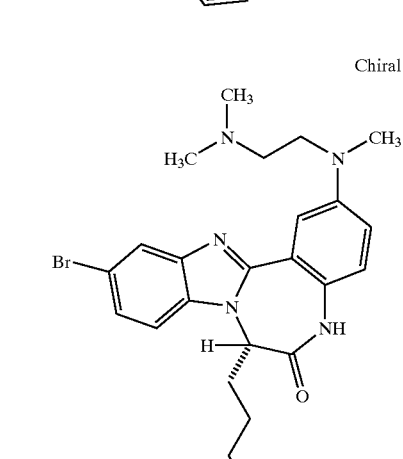 Chiral | 6000#56655 | 97.83451842 |

| | Sample ID | % Inhibition |
|---|---|---|
| 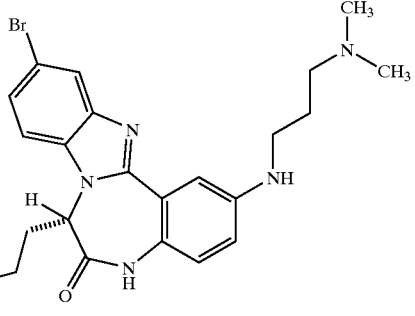 Chiral | 6000#56687 | 96.80025856 |
| 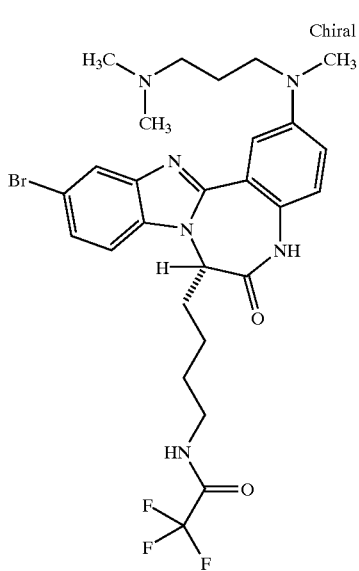 Chiral | 6000#56695 | 95.76599871 |

-continued
| | Sample ID | % Inhibition |
|---|---|---|
| Chiral 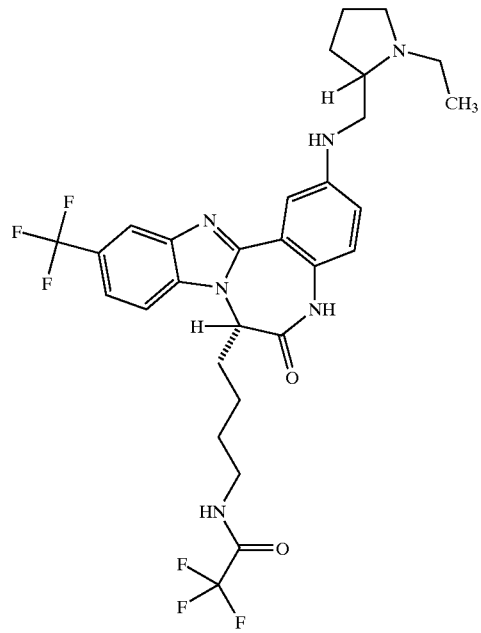 | 6000#56957 | 97.41584495 |
| Chiral 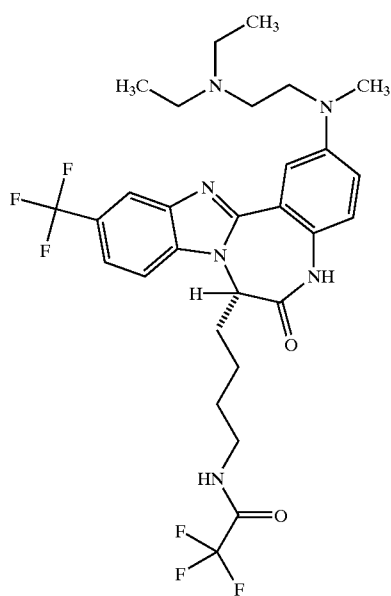 | 6000#56919 | 95.78374702 |

-continued
| | Sample ID | % Inhibition |
|---|---|---|
| 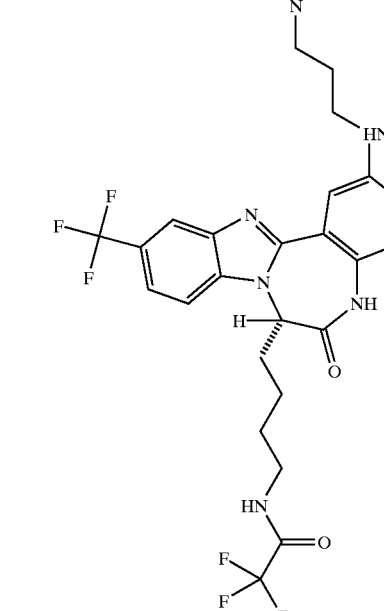 | 6000#56927 | 96.32777967 |
| 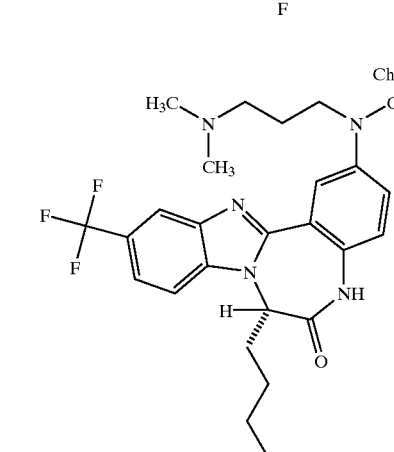 | 6000#56935 | 95.78374702 |

-continued
| | Sample ID | % Inhibition |
|---|---|---|
| Chiral 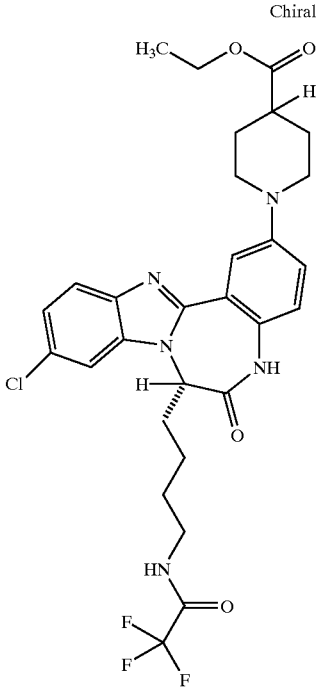 | 6000#57085 | 96.66778862 |
| Chiral 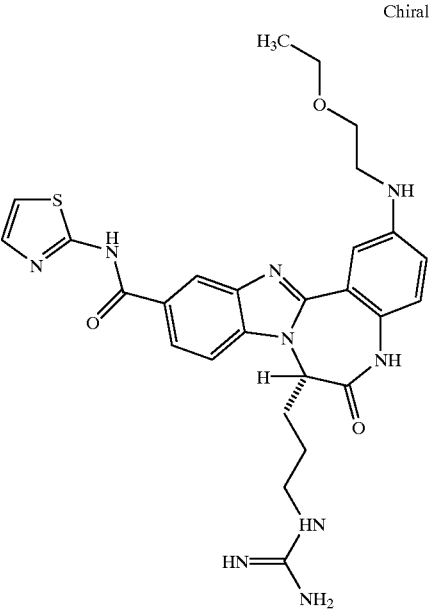 | 6000#57258 | 96.89629069 |

-continued
| | Sample ID | % Inhibition |
|---|---|---|
| Chiral 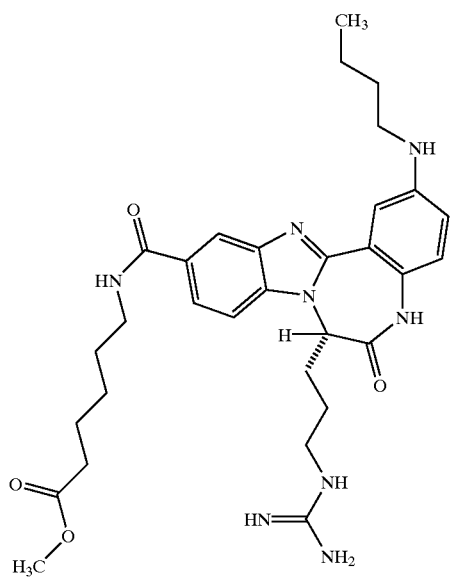 | 6000#57343 | 100.0732869 |
| Chiral 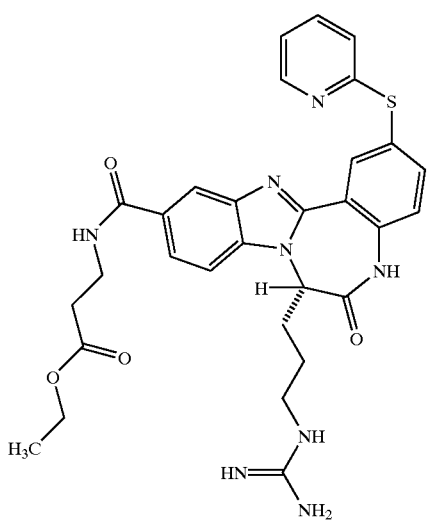 | 6000#57425 | 97.78172138 |

-continued
| | Sample ID | % Inhibition |
|---|---|---|
| Chiral 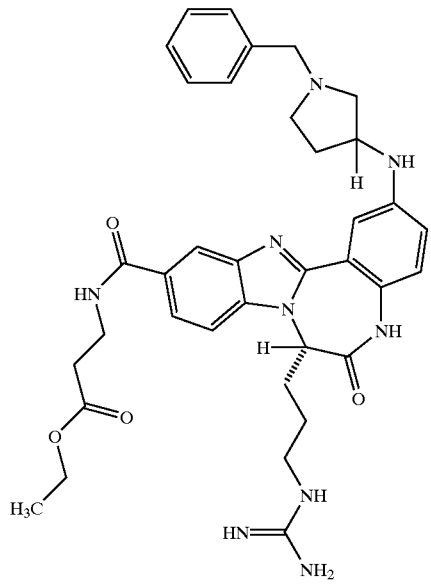 | 6000#57389 | 97.30848861 |
| Chiral 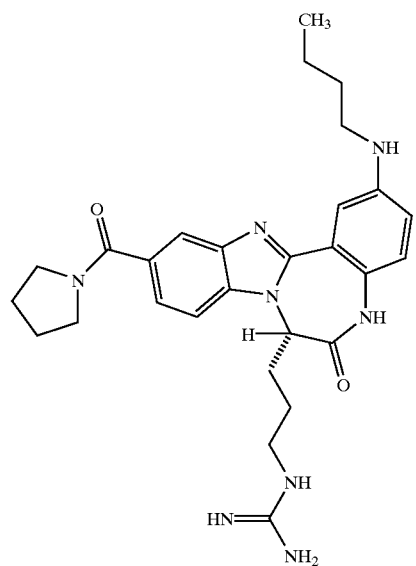 | 6000#57503 | 97.38476626 |

-continued
| | Sample ID | % Inhibition |
|---|---|---|
| 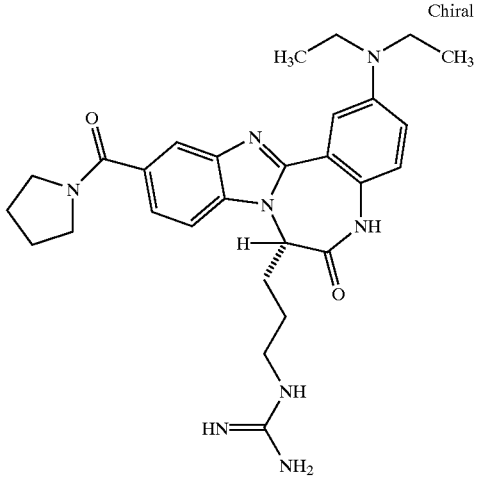 Chiral | 6000#57519 | 100 |
| 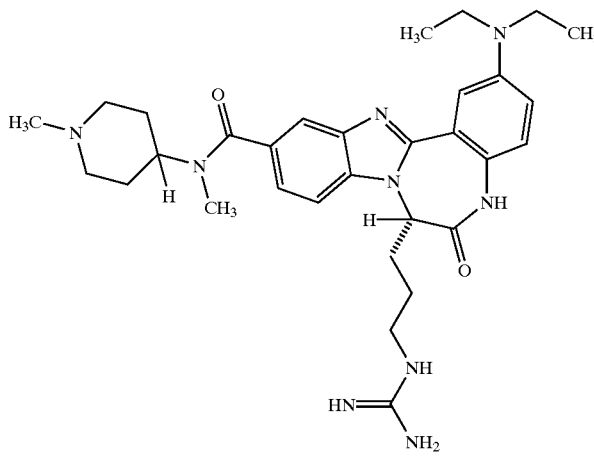 Chiral | 6000#57999 | 95.14101257 |
| 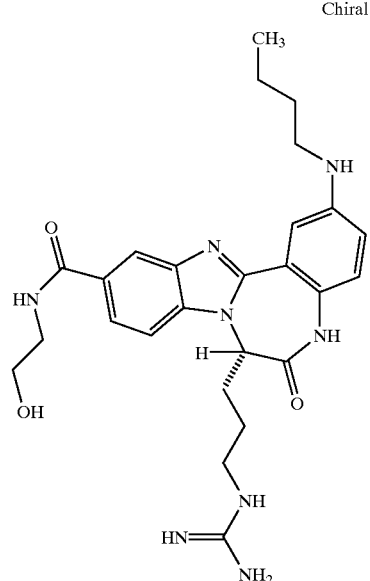 Chiral | 6000#58223 | 97.04081633 |

| | Sample ID | % Inhibition |
|---|---|---|
| 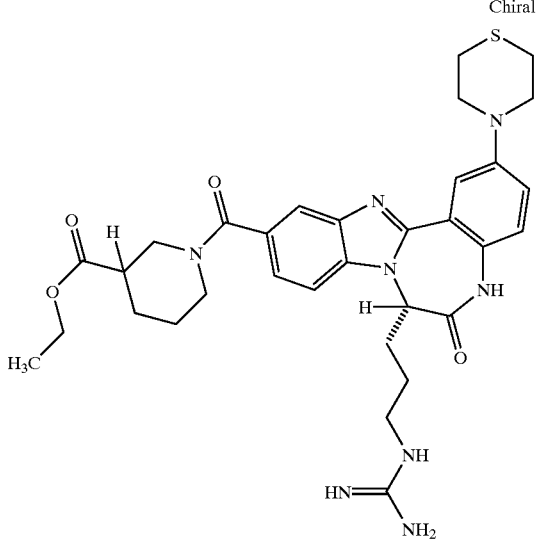 Chiral | 6000#58475 | 99.05619906 |
| 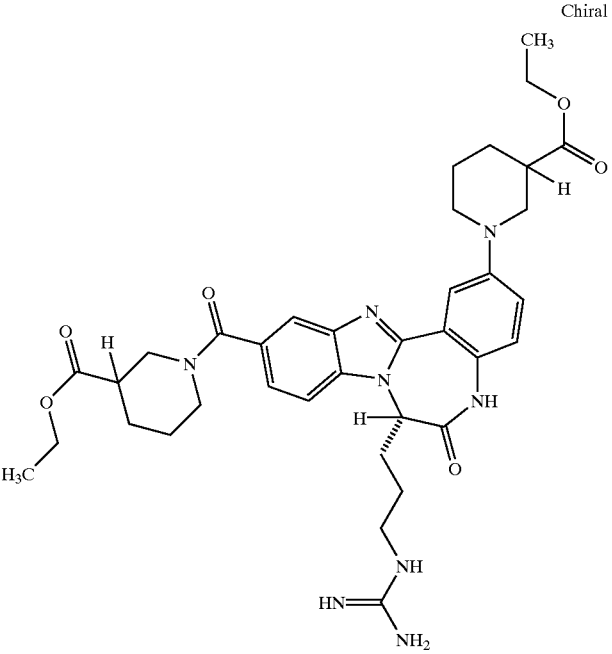 Chiral | 6000#58437 | 100.4290004 |

-continued
| | Sample ID | % Inhibition |
|---|---|---|
| 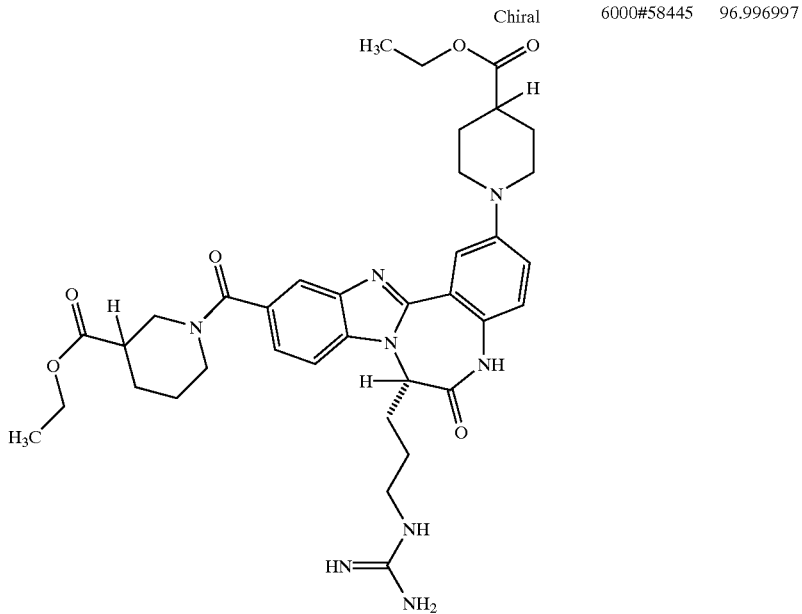 Chiral | 6000#58445 | 96.996997 |
| 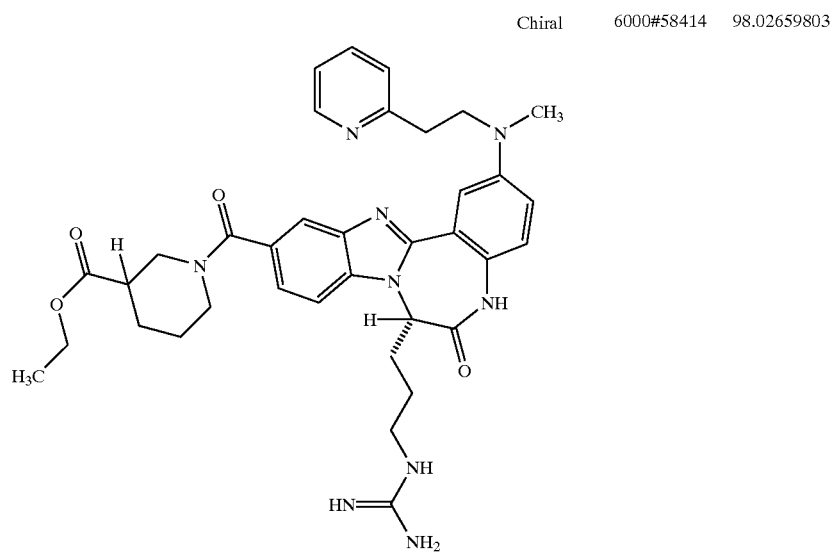 Chiral | 6000#58414 | 98.02659803 |

-continued
| | Sample ID | % Inhibition |
|---|---|---|
| Chiral | 6000#59152 | 97.17623687 |
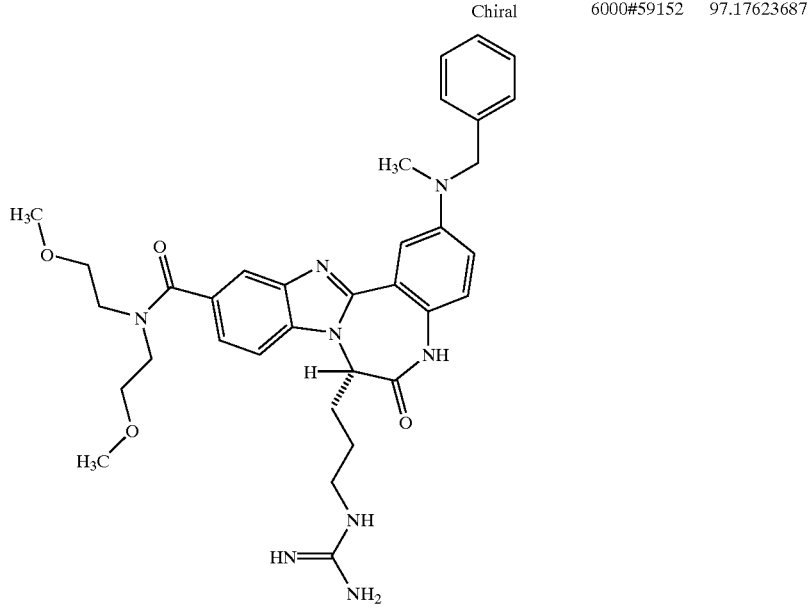
| Chiral | 6000#59355 | 97.22728931 |
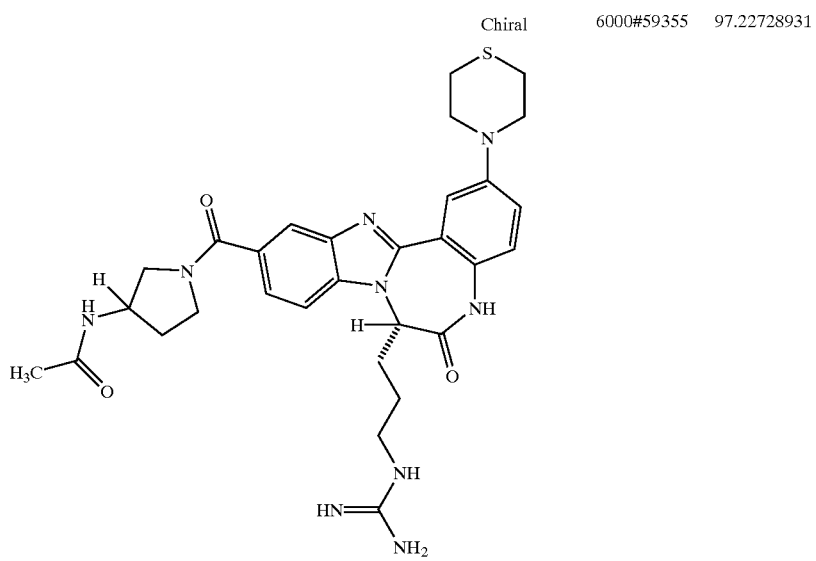

-continued

| | Sample ID | % Inhibition |
|---|---|---|
| Chiral [structure] | 6000#59317 | 96.64356074 |
| Chiral [structure] | 6000#59325 | 95.18423933 |

-continued

| | Sample ID | % Inhibition |
|---|---|---|
| Chiral | 6000#59393 | 96.06837607 |
| Chiral | 6000#59425 | 96.75213675 |

| | Sample ID | % Inhibition |
|---|---|---|
| Chiral 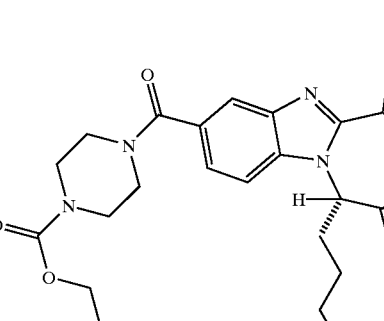 | 6000#59387 | 97.77777778 |
| Chiral 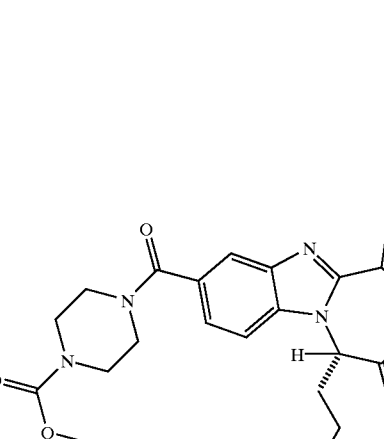 | 6000#59435 | 96.06837607 |

-continued
| | Sample ID | % Inhibition |
|---|---|---|
| 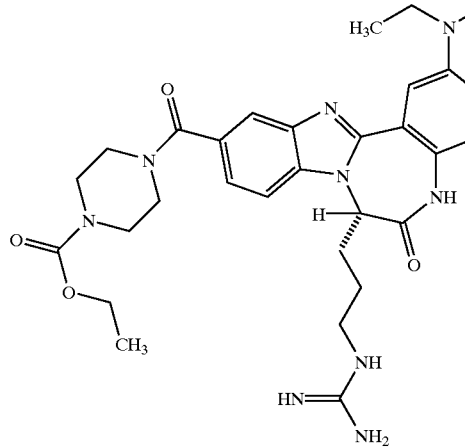 | 6000#59439 | 96.41025641 |
| 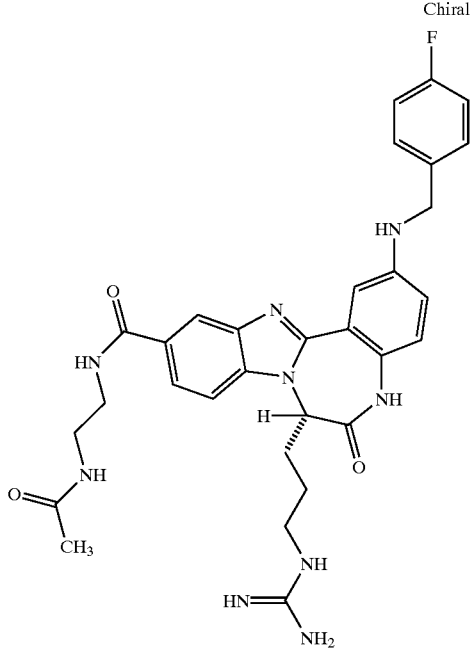 | 6000#59512 | 98.70392872 |

|  | Sample ID | % Inhibition |
|---|---|---|
| 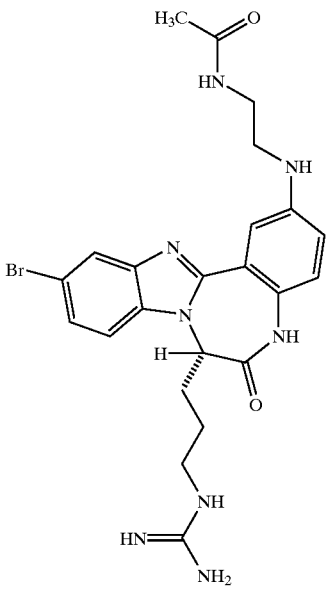 Chiral | 6000#60738 | 96.47910497 |
| 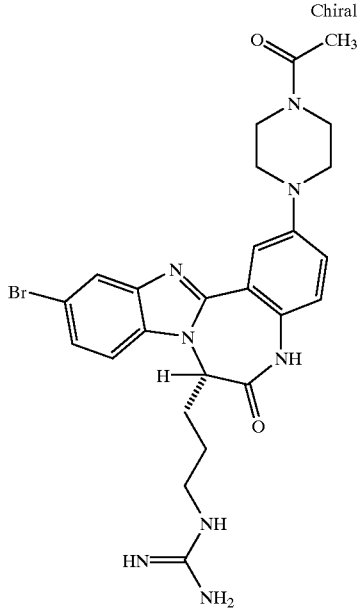 Chiral | 6000#60754 | 97.26883843 |

-continued
| | Sample ID | % Inhibition |
|---|---|---|
| Chiral 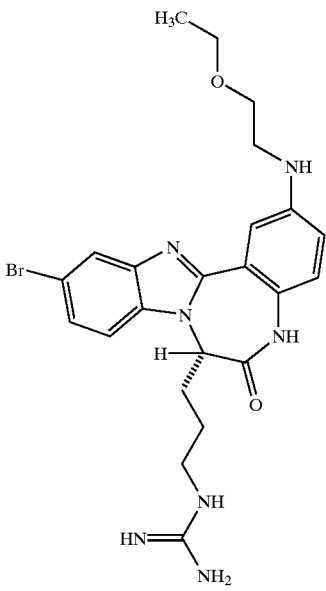 | 6000#60778 | 98.84830536 |
| Chiral 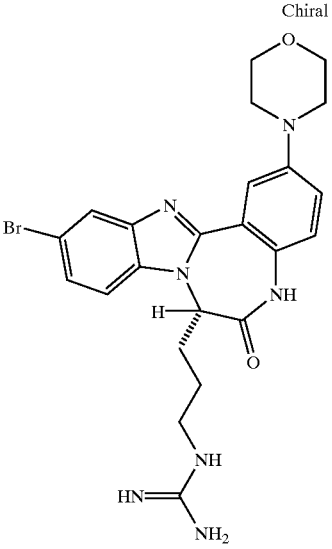 | 6000#60794 | 97.26883843 |

-continued

| | Sample ID | % Inhibition |
|---|---|---|
| Chiral (structure) | 6000#60735 | 99.90128332 |
| Chiral (structure) | 6000#60857 | 95.29719138 |

-continued
| | Sample ID | % Inhibition |
|---|---|---|
| 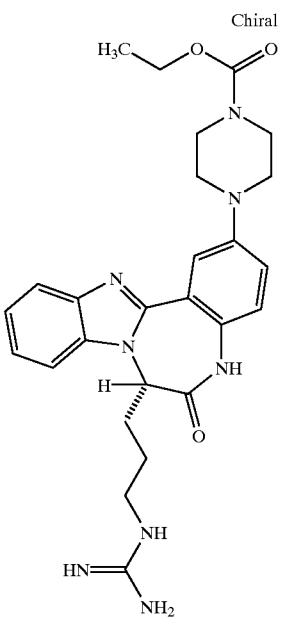 Chiral | 6000#60826 | 95.03592423 |
| 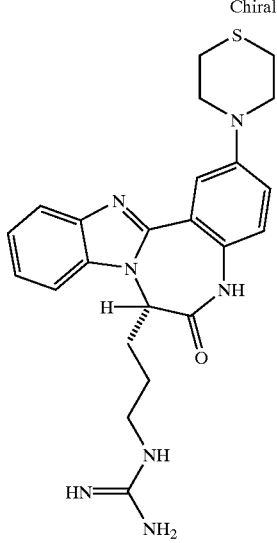 Chiral | 6000#60875 | 100.5225343 |

-continued

| | Sample ID | % Inhibition |
|---|---|---|
| 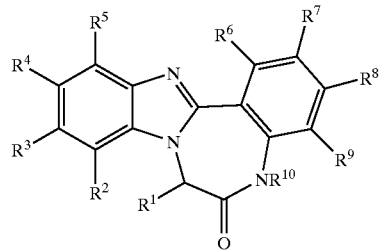 | 6000#60879 | 97.38732854 |

EXAMPLE 13

Penile Erection Due to Administration of a Tetracyclic Benzimidazole Compound Adult male rats are housed 2–3 per cage and are acclimated to the standard vivarium light cycle (12 hr. light, 12 hr. dark), rat chow and water for a least a week prior to testing. All experiments are performed between 9 a.m. and noon and rats are placed in cylindrical, clear plexiglass chambers during the 60 minute observation period. Mirrors are positioned below and to the sides of the chambers, to improve viewing.

Observations begin 10 minutes after an unstraperitoneal injection of either saline or compound. An observer counts the number of grooming motions, stretches, yawns and penile erections (spontaneously occurring, not elicited by genital grooming) and records them every 5 minutes, for a total of 60 minutes. The observer is unaware of the treatment and animals are tested once, with n=6 in each group. Values in the figures represent the group mean and standard error of the mean. HP 228 can be used as a positive control for penile erections. Significant differences between groups are determined by an overall analysis of variance and the Student Neunmann-Keuls post hoc test can be used to identify individual differences between groups ($p \leq 0.05$).

Although the invention has been described with reference to the examples provided above, it should be understood that various modifications can be made by those skilled in the art without departing from the invention. Accordingly, the invention is set out in the following claims.

We claim:
1. A single compound of the formula:

[Structure with substituents $R^1$ through $R^{10}$]

wherein:
$R^1$ is selected from the group consisting of a hydrogen atom, $C_1$ to $C_{12}$ alkyl, $C_1$ to $C_{12}$ substituted alkyl, phenyl, substituted phenyl, $C_7$ to $C_{18}$ phenylalkyl, $C_7$ to $C_{18}$ substituted phenylalkyl, $C_1$ to $C_{12}$ heterocycloalkyl, $C_1$ to $C_{12}$ substituted heterocycloalkyl, heteroaryl, substituted heteroaryl, cyano, $C_1$ to $C_{12}$ acyl, $C_1$ to $C_{12}$ substituted acyl, $C_1$ to $C_{12}$ alkoxycarbonyl, $C_1$ to $C_{12}$ substituted alkoxycarbonyl, $C_1$ to $C_{12}$ alkylaminocarbonyl, $C_1$ to $C_{12}$ substituted alkylaminocarbonyl, phenylaminocarbonyl, substituted phenylaminocarbonyl, $C_1$ to $C_{10}$ alkylthio, $C_1$ to $C_{10}$ substituted alkylthio, $C_1$ to $C_{10}$ alkylsulfonyl, $C_1$ to $C_{10}$ substituted alkylsulfonyl, $C_1$ to $C_{10}$ alkylsulfoxide, $C_1$ to $C_{10}$ substituted alkylsulfoxide, phenylthio, substituted phenylthio, phenylsulfoxide, substituted phenylsulfoxide, phenylsulfonyl, substituted phenylsulfonyl, heterocycle, substituted heterocycle, cyclic $C_2$ to $C_7$ alkylene, substituted cyclic $C_2$ to $C_7$ alkylene, cyclic $C_2$ to $C_7$ heteroalkylene, substituted cyclic $C_2$ to $C_7$ heteroalkylene, naphthyl, substituted naphthyl, $C_5$ to $C_7$ cycloalkyl, $C_5$ to $C_7$ substituted cycloalkyl, $C_5$ to $C_7$ cycloalkenyl and $C_5$ to $C_7$ substituted cycloalkenyl;

$R^2$, $R^3$, $R^5$, $R^6$, $R^8$ and $R^9$ are, independently, selected from the group consisting of a hydrogen atom, halo, hydroxy, protected hydroxy, cyano, $C_1$ to $C_{12}$ alkyl, $C_2$ to $C_{12}$ alkenyl, $C_2$ to $C_{12}$ alkynyl, $C_1$ to $C_{12}$ substituted alkyl, $C_2$ to $C_{12}$ substituted alkenyl, $C_2$ to $C_{12}$ substituted alkynyl, $C_1$ to $C_{12}$ alkoxy, $C_1$ to $C_{12}$ substituted alkoxy, $C_1$ to $C_{12}$ acyloxy, $C_1$ to $C_{12}$ acyl, $C_3$ to $C_7$ cycloalkyl, $C_3$ to $C_7$ substituted cycloalkyl, $C_5$ to $C_7$ cycloalkenyl, $C_5$ to $C_7$ substituted cycloalkenyl, heterocyclic ring, substituted heterocyclic ring, $C_7$ to $C_{18}$ phenylalkyl, $C_7$ to $C_{18}$ substituted phenylalkyl, $C_1$ to $C_{12}$ heterocycloalkyl, $C_1$ to $C_{12}$ substituted heterocycloalkyl, phenyl, substituted phenyl, naphthyl, substituted naphthyl, cyclic $C_2$ to $C_7$ alkylene, substituted cyclic $C_2$ to $C_7$ alkylene, cyclic $C_2$ to $C_7$ heteroalkylene, substituted cyclic $C_2$ to $C_7$ heteroalkylene, carboxy, protected carboxy, hydroxymethyl, protected hydroxymethyl, amino, protected amino, (monosubstituted)amino, protected (monosubstituted)amino, (disubstituted)amino, $C_1$ to $C_{10}$ alkylamino, $C_1$ to $C_{10}$ alkyl protected amino, $C_1$ to $C_{10}$ alkyl (monosubstituted)amino, $C_1$ to $C_{10}$ alkyl, protected (monosubstituted)amino, $C_1$ to $C_{10}$ alkyl (disubstituted)amino, $C_1$ to $C_{10}$ substituted alkylamino, $C_1$ to $C_{10}$ substituted alkyl protected amino, $C_1$ to $C_{10}$ substituted alkyl (monosubstituted)amino, $C_1$ to $C_{10}$ substituted alkyl protected (monosubstituted)amino, $C_1$ to $C_{10}$ substituted alkyl(disubstituted)amino, carboxamide, protected carboxamide, $C_1$ to $C_{10}$ alkylthio, $C_1$ to $C_{10}$ substituted alkylthio, $C_1$ to $C_{10}$ alkylsulfonyl, $C_1$ to $C_{10}$ substituted alkylsulfonyl, $C_1$ to $C_{10}$ alkylsulfoxide, $C_1$ to $C_{10}$ substituted alkylsulfoxide, phenylthio, substituted phenylthio, phenylsulfoxide, substituted phenylsulfoxide, phenylsulfonyl, substituted phenylsulfonyl and and the group consisting of (i) the formula —C(O)NR$^{11}$R$^{12}$, (i) the formula —C(O)R$^{11}$, (iii) the formula —NR$^{11}$R$^{12}$, (iv) the formula —SR$^{11}$, (v) the formula —OR$^{11}$ and (vi) the formula —C(O)OR$^{11}$, wherein R$^{11}$ and R$^{12}$ are, independently, selected from the group consisting of a hydrogen atom, $C_1$ to $C_{12}$ alkyl, $C_1$ to $C_{12}$ substituted alkyl, $C_2$ to $C_{12}$ alkenyl, $C_2$ to $C_{12}$ substituted alkenyl, phenyl, substituted phenyl, naphthyl, substituted naphthyl, $C_7$ to $C_{18}$ phenylalkyl, $C_7$ to $C_{18}$ substituted phenylalkyl, $C_1$ to $C_{12}$ heterocycloalkyl, $C_1$ to $C_{12}$ substituted heterocycloalkyl, heteroaryl, substituted heteroaryl, heterocycle, substituted heterocycle, $C_1$ to $C_{12}$ acyl, $C_1$ to $C_{12}$ substituted acyl, phenylsulfonyl, substituted phenylsulfonyl, $C_1$ to $C_{10}$ alkylsulfonyl, $C_1$ to $C_{10}$ substituted alkylsulfonyl, $C_1$ to $C_{12}$ alkylaminocarbonyl, $C_1$ to $C_{12}$ substituted alkylaminocarbonyl, phenylaminocarbonyl, and substituted phenylaminocarbonyl, or, in the formula —C(O)NR$^{11}$R$^{12}$, R$^{11}$ and R$^{12}$ join the nitrogen atom in the formula to form a heterocycle or substituted heterocycle;

R$^4$ is selected from the group consisting of halo, hydroxy, protected hydroxy, cyano, $C_1$ to $C_{12}$ alkyl, $C_2$ to $C_{12}$ alkenyl, $C_2$ to $C_{12}$ alkynyl, $C_1$ to $C_{12}$ substituted alkyl, $C_2$ to $C_{12}$ substituted alkenyl, $C_2$ to $C_{12}$ substituted alkynyl, $C_1$ to $C_{12}$ alkoxy, $C_1$ to $C_{12}$ substituted alkoxy, $C_1$ to $C_{12}$ acyloxy, $C_1$ to $C_{12}$ acyl, $C_3$ to $C_7$ cycloalkyl, $C_3$ to $C_7$ substituted cycloalkyl, $C_5$ to $C_7$ cycloalkenyl, $C_5$ to $C_7$ substituted cycloalkenyl, heterocyclic ring, substituted heterocyclic ring, $C_7$ to $C_{18}$ phenylalkyl, $C_7$ to $C_{18}$ substituted phenylalkyl, $C_1$ to $C_{12}$ heterocycloalkyl, $C_1$ to $C_{12}$ substituted heterocycloalkyl, phenyl, substituted phenyl, naphthyl, substituted naphthyl, cyclic $C_2$ to $C_7$ alkylene, substituted cyclic $C_2$ to $C_7$ alkylene, cyclic $C_2$ to $C_7$ heteroalkylene, substituted cyclic $C_2$ to $C_7$ heteroalkylene, carboxy, protected carboxy, hydroxymethyl, protected hydroxymethyl, amino, protected amino, (monosubstituted)amino, protected (monosubstituted)amino, (disubstituted)amino, $C_1$ to $C_{10}$ alkylamino, $C_1$ to $C_{10}$ alkyl protected amino, $C_1$ to $C_{10}$ alkyl (monosubstituted)amino, $C_1$ to $C_{10}$ alkyl, protected (monosubstituted)amino, $C_1$ to $C_{10}$ alkyl (disubstituted)amino, $C_1$ to $C_{10}$ substituted alkylamino, $C_1$ to $C_{10}$ substituted alkyl protected amino, $C_1$ to $C_{10}$ substituted alkyl (monosubstituted)amino, $C_1$ to $C_{10}$ substituted alkyl protected (monosubstituted)amino, $C_1$ R$^7$ is selected from the group consisting of a halo, hydroxy, protected hydroxy, cyano, $C_1$ to $C_{12}$ alkyl, $C_2$ to $C_{12}$ alkenyl, $C_2$ to $C_{12}$ alkynyl, $C_1$ to $C_{12}$ substituted alkyl, $C_2$ to $C_{12}$ substituted alkenyl, $C_2$ to $C_{12}$ substituted alkynyl, $C_1$ to $C_{12}$ alkoxy, $C_1$ to $C_{12}$ substituted alkoxy, $C_1$ to $C_{12}$ acyloxy, $C_1$ to $C_{12}$ acyl, $C_3$ to $C_7$ cycloalkyl, $C_3$ to $C_7$ substituted cycloalkyl, $C_5$ to $C_7$ cycloalkenyl, $C_5$ to $C_7$ substituted cycloalkenyl, heterocyclic ring, substituted heterocyclic ring, $C_7$ to $C_{18}$ phenylalkyl, $C_7$ to $C_{18}$ substituted phenylalkyl, $C_1$ to $C_{12}$ heterocycloalkyl, $C_1$ to $C_{12}$ substituted heterocycloalkyl, phenyl, substituted phenyl, naphthyl, substituted naphthyl, cyclic $C_2$ to $C_7$ alkylene, substituted cyclic $C_2$ to $C_7$ alkylene, cyclic $C_2$ to $C_7$ heteroalkylene, substituted cyclic $C_2$ to $C_7$ heteroalkylene, carboxy, protected carboxy, hydroxymethyl, protected hydroxymethyl, amino, protected amino, (monosubstituted)amino, protected (monosubstituted)amino, (disubstituted)amino, $C_1$ to $C_{10}$ alkylamino, $C_1$ to $C_{10}$ alkyl protected amino, $C_1$ to $C_{10}$ alkyl (monosubstituted)amino, $C_1$ to $C_{10}$ alkyl, protected (monosubstituted)amino, $C_1$ to $C_{10}$ alkyl (disubstituted)amino, $C_1$ to $C_{10}$ substituted alkylamino, $C_1$ to $C_{10}$ substituted alkyl protected amino, $C_1$ to $C_{10}$ substituted alkyl (monosubstituted)amino, $C_1$ to $C_{10}$ substituted alkyl protected (monosubstituted)amino, $C_1$ to $C_{10}$ substituted alkyl(disubstituted)amino, carboxamide, protected carboxamide, $C_1$ to $C_{10}$ alkylthio, $C_1$ to $C_{10}$ substituted alkylthio, $C_1$ to $C_{10}$ alkylsulfonyl, $C_1$ to $C_{10}$ substituted alkylsulfonyl, $C_1$ to $C_{10}$ alkylsulfoxide, $C_1$ to $C_{10}$ substituted alkylsulfoxide, phenylthio, substituted phenylthio, phenylsulfoxide, substituted phenylsulfoxide, phenylsulfonyl, substituted phenylsulfonyl and and the group consisting of (i) the formula —C(O)NR$^{11}$R$^{12}$, (i) the formula —C(O)R$^{11}$, (iii) the formula —NR$^{11}$R$^{12}$, (iv) the formula —SR$^{11}$, (v) the formula —OR$^{11}$, and (vi) the formula —C(O)OR$^{11}$, wherein R$^{11}$ and R$^{12}$ are, independently, selected from the group consisting of a hydrogen atom, $C_1$ to $C_{12}$ alkyl, $C_1$ to $C_{12}$ substituted alkyl, $C_2$ to $C_{12}$ alkenyl, $C_2$ to $C_{12}$ substituted alkenyl, phenyl, substituted phenyl, naphthyl, substituted naphthyl, $C_7$ to $C_{18}$ phenylalkyl, $C_7$ to $C_{18}$ substituted phenylalkyl, $C_1$ to $C_{12}$ heterocycloalkyl, $C_1$ to $C_{12}$ substituted heterocycloalkyl, heteroaryl, substituted heteroaryl, heterocycle, substituted heterocycle, $C_1$ to $C_{12}$ acyl, $C_1$ to $C_{12}$ substituted acyl, phenylsulfonyl, substituted phenylsulfonyl, $C_1$ to $C_{10}$ alkylsulfonyl, $C_1$ to $C_{10}$ substituted alkylsulfonyl, $C_1$ to $C_{12}$ alkylaminocarbonyl, $C_1$ to $C_{12}$ substituted alkylaminocarbonyl, phenylaminocarbonyl, and substituted phenylaminocarbonyl; and R$^{10}$ is selected from the group consisting of a hydrogen atom, $C_1$ to $C_{12}$ alkyl, $C_1$ to $C_{12}$ substituted alkyl, $C_2$ to $C_{12}$ alkenyl, $C_2$ to $C_{12}$ substituted alkenyl, $C_7$ to $C_{18}$ phenylalkyl, $C_7$ to $C_{18}$ substituted phenylalkyl, $C_1$ to $C_{12}$ heterocycloalkyl and $C_1$ to $C_{12}$ substituted heterocycloalkyl; or a pharmaceutically acceptable salt of a compound thereof.

2. The single compound of claim 1, wherein

R$^1$ is selected from the group consisting of a hydrogen atom, $C_1$ to $C_{12}$ alkyl, $C_1$ to $C_{12}$ substituted alkyl, phenyl, substituted phenyl, $C_7$ to $C_{18}$ phenylalkyl, $C_7$ to $C_{18}$ substituted phenylalkyl, $C_1$ to $C_{12}$ heterocycloalkyl, $C_1$ to $C_{12}$ substituted heterocycloalkyl, heteroaryl, substituted heteroaryl, $C_1$ to $C_{10}$ alkylthio, $C_1$ to $C_{10}$ substituted alkylthio, heterocycle and substituted heterocycle.

3. The single compound of claim 1, wherein

R$^2$, R$^3$, and R$^5$ are, independently, selected from the group consisting of a hydrogen atom, halo, hydroxy, protected hydroxy, cyano, $C_1$ to $C_{12}$ alkyl, $C_1$ to $C_{12}$ substituted alkyl, $C_1$ to $C_{12}$ alkoxy, $C_1$ to $C_{12}$ substituted alkoxy, carboxy, protected carboxy, $C_1$ to $C_{10}$ alkylthio, $C_1$ to $C_{10}$ substituted alkylthio, the formula —C(O)NR$^{11}$R$^{12}$ and the formula —C(O)R$^{11}$, wherein R$^{11}$ and R$^{12}$ are, independently, selected from the group consisting of a hydrogen atom, $C_1$ to $C_{12}$ alkyl, $C_1$ to $C_{12}$ substituted alkyl, phenyl, substituted phenyl, $C_7$ to $C_{18}$ phenylalkyl, $C_7$ to $C_{18}$ substituted phenylalkyl, $C_1$ to $C_{12}$ heterocycloalkyl, $C_1$ to $C_{12}$ substituted heterocycloalkyl, heteroaryl, substituted heteroaryl, heterocycle and substituted heterocycle, or, in the formula —C(O)NR$^{11}$R$^{12}$, R$^{11}$ and R$^{12}$ join the nitrogen atom in the formula to form a heterocycle or substituted heterocycle; and R$^4$ is selected from the group consisting of halo, hydroxy, protected hydroxy, cyano, $C_1$ to $C_{12}$ alkyl, $C_1$ to $C_{12}$ substituted alkyl, $C_1$ to $C_{12}$ alkoxy, $C_1$ to $C_{12}$ substituted alkoxy, carboxy, protected carboxy, $C_1$ to $C_{10}$ alkylthio, $C_1$ to $C_{10}$ substituted alkylthio, the formula —C(O)NR$^{11}$R$^{12}$ and the formula —C(O)R$^{11}$, wherein R$^{11}$ and R$^{12}$ are, independently, selected from the group consisting of a hydrogen atom, $C_1$ to $C_{12}$ alkyl, $C_1$ to $C_{12}$ substituted alkyl, phenyl, substituted phenyl, $C_7$ to $C_{18}$ phenylalkyl, $C_7$ to $C_{18}$ substituted phenylalkyl, $C_1$ to $C_{12}$ heterocycloalkyl, $C_1$ to $C_{12}$ substituted heterocycloalkyl, heteroaryl, substituted heteroaryl, heterocycle and substituted heterocycle, or, in the formula —C(O)NR$^{11}$R$^{12}$, R$^{11}$ and R$^{12}$ join the nitrogen atom in the formula to form a heterocycle or substituted heterocycle.

4. The single compound of claim 1, wherein

R$^2$, R$^3$, and R$^5$ are each a hydrogen atom, and R$^4$ is the formula —C(O)NR$^{11}$R$^{12}$ or the formula —C(O)R$^{11}$, wherein R$^{11}$ and R$^{12}$ are, independently, selected from the group consisting of a hydrogen atom, $C_1$ to $C_{12}$ alkyl, $C_1$ to $C_{12}$ substituted alkyl, phenyl, substituted phenyl, $C_7$ to $C_{18}$ phenylalkyl, $C_7$ to $C_{18}$ substituted phenylalkyl, $C_1$ to $C_{12}$ heterocycloalkyl, $C_1$ to $C_{12}$ substituted heterocycloalkyl, heteroaryl, substituted heteroaryl, heterocycle and substituted heterocycle, or, in the formula —C(O)NR$^{11}$R$^{12}$, R$^{11}$ and R$^{12}$ join the nitrogen atom in the formula to form a heterocycle or substituted heterocycle.

5. The single compound of claim 1, wherein

R$^6$, R$^8$ and R$^9$ are, independently, selected from the group consisting of a hydrogen atom, halo, heterocycle, substituted heterocycle, the formula —NR$^{11}$R$^{12}$ and the formula —SR$^{11}$, wherein R$^{11}$ and R$^{12}$ are, independently, selected from the group consisting of a hydrogen atom, $C_1$ to $C_{12}$ alkyl, $C_1$ to $C_{12}$ substituted alkyl, $C_2$ to $C_{12}$ alkenyl, $C_2$ to $C_{12}$ substituted alkenyl, $C_7$ to $C_{18}$ phenylalkyl, $C_7$ to $C_{18}$ substituted phenylalkyl, $C_1$ to $C_{12}$ heterocycloalkyl, $C_1$ to $C_{12}$ substituted heterocycloalkyl, heteroaryl, substituted heteroaryl, heterocycle and substituted heterocycle; and R$^7$ is selected from the group consisting of halo, heterocycle, substituted heterocycle, the formula —NR$^{11}$R$^{12}$ and the formula —SR$^{11}$, wherein R$^{11}$ and R$^{12}$ are, independently, selected from the group consisting of a hydrogen atom, $C_1$ to $C_{12}$ alkyl, $C_1$ to $C_{12}$ substituted alkyl, $C_2$ to $C_{12}$ alkenyl, $C_2$ to $C_{12}$ substituted alkenyl, $C_7$ to $C_{18}$ phenylalkyl, $C_7$ to $C_{18}$ substituted phenylalkyl, $C_1$ to $C_{12}$ heterocycloalkyl, $C_1$ to $C_{12}$ substituted heterocycloalkyl, heteroaryl, substituted heteroaryl, heterocycle and substituted heterocycle.

6. The single compound of claim 1, wherein

R$^6$, R$^8$ and R$^9$ are each a hydrogen atom, and R$^7$ is selected from the group consisting of halo, heterocycle, substituted heterocycle, the formula —NR$^{11}$R$^{12}$ and the formula —SR$^{11}$, wherein R$^{11}$ and R$^{12}$ are, independently, selected from the group consisting of a hydrogen atom, $C_1$ to $C_{12}$ alkyl, $C_1$ to $C_{12}$ substituted alkyl, $C_2$ to $C_{12}$ alkenyl, $C_2$ to $C_{12}$ substituted alkenyl, $C_7$ to $C_{18}$ phenylalkyl, $C_7$ to $C_{18}$ substituted phenylalkyl, $C_1$ to $C_{12}$ heterocycloalkyl, $C_1$ to $C_{12}$ substituted heterocycloalkyl, heteroaryl, substituted heteroaryl, heterocycle and substituted heterocycle.

7. The single compound of claim 1, wherein R$^{10}$ is a hydrogen atom.

8. The single compound of claim 1, wherein

R$^1$ is selected from the group consisting of a hydrogen atom, $C_1$ to $C_{12}$ alkyl, $C_1$ to $C_{12}$ substituted alkyl, phenyl, substituted phenyl, $C_7$ to $C_{18}$ phenylalkyl, $C_7$ to $C_{18}$ substituted phenylalkyl, $C_1$ to $C_{12}$ heterocycloalkyl, $C_1$ to $C_{12}$ substituted heterocycloalkyl, heteroaryl, substituted heteroaryl, $C_1$ to $C_{10}$ alkylthio, $C_1$ to $C_{10}$ substituted alkylthio, heterocycle and substituted heterocycle;

$R^2$, $R^3$, and $R^5$ are, independently, selected from the group consisting of a hydrogen atom, halo, hydroxy, protected hydroxy, cyano, $C_1$ to $C_{12}$ alkyl, $C_1$ to $C_{12}$ substituted alkyl, $C_1$ to $C_{12}$ alkoxy, $C_1$ to $C_{12}$ substituted alkoxy, carboxy, protected carboxy, $C_1$ to $C_{10}$ alkylthio, $C_1$ to $C_{10}$ substituted alkylthio, the formula —C(O)NR$^{11}$R$^{12}$ and the formula —C(O)R$^{11}$, wherein R$^{11}$ and R$^{12}$ are, independently, selected from the group consisting of a hydrogen atom, $C_1$ to $C_{12}$ alkyl, $C_1$ to $C_{12}$ substituted alkyl, phenyl, substituted phenyl, $C_7$ to $C_{18}$ phenylalkyl, $C_7$ to $C_{18}$ substituted phenylalkyl, $C_1$ to $C_{12}$ heterocycloalkyl, $C_1$ to $C_{12}$ substituted heterocycloalkyl, heteroaryl, substituted heteroaryl, heterocycle and substituted heterocycle, or, in the formula —C(O)NR$^{11}$R$^{12}$, R$^{11}$ and R$^{12}$ join the nitrogen atom in the formula to form a heterocycle or substituted heterocycle;

$R^4$ is selected from the group consisting of halo, hydroxy, protected hydroxy, cyano, $C_1$ to $C_{12}$ alkyl, $C_1$ to $C_{12}$ substituted alkyl, $C_1$ to $C_{12}$ alkoxy, $C_1$ to $C_{12}$ substituted alkoxy, carboxy, protected carboxy, $C_1$ to $C_{10}$ alkylthio, $C_1$ to $C_{10}$ substituted alkylthio, the formula —C(O)NR$^{11}$R$^{12}$ and the formula —C(O)R$^{11}$, wherein R$^{11}$ and R$^{12}$ are, independently, selected from the group consisting of a hydrogen atom, $C_1$ to $C_{12}$ alkyl, $C_1$ to $C_{12}$ substituted alkyl, phenyl, substituted phenyl, $C_7$ to $C_{18}$ phenylalkyl, $C_7$ to $C_{18}$ substituted phenylalkyl, $C_1$ to $C_{12}$ heterocycloalkyl, $C_1$ to $C_{12}$ substituted heterocycloalkyl, heteroaryl, substituted heteroaryl, heterocycle and substituted heterocycle, or, in the formula —C(O)NR$^{11}$R$^{12}$, R$^{11}$ and R$^{12}$ join the nitrogen atom in the formula to form a heterocycle or substituted heterocycle;

$R^6$, $R^8$ and $R^9$ are each a hydrogen atom, and $R^7$ is selected from the group consisting of halo, heterocycle, substituted heterocycle, the formula —NR$^{11}$R$^{12}$ and the formula —SR$^{11}$, wherein R$^{11}$ and R$^{12}$ are, independently, selected from the group consisting of a hydrogen atom, $C_1$ to $C_{12}$ alkyl, $C_1$ to $C_{12}$ substituted alkyl, $C_2$ to $C_{12}$ alkenyl, $C_2$ to $C_{12}$ substituted alkenyl, $C_7$ to $C_{18}$ phenylalkyl, $C_7$ to $C_{18}$ substituted phenylalkyl, $C_1$ to $C_{12}$ heterocycloalkyl, $C_1$ to $C_{12}$ substituted heterocycloalkyl, heteroaryl, substituted heteroaryl, heterocycle and substituted heterocycle; and $R^{10}$ is a hydrogen atom.

9. The single compound of claim 1, wherein $R^1$ is selected from the group consisting of a hydrogen atom, methyl, 2-propyl, 2-butyl, aminocarbonylethyl, 2-methylmercaptoethyl, phenyl, benzyl, cyclohexylmethyl, 4-methoxybenzyl, 4-chlorobenzyl, 3-indolylmethyl, 4-(trifluoroacetyl)aminobutyl and 3-guanidinopropyl;

$R^2$, $R^3$, $R^5$, $R^6$, $R^8$, $R^9$ and $R^{10}$ are each a hydrogen atom;

$R^4$ is the formula —C(O)NR$^{11}$R$^{12}$, wherein R$^{11}$ and R$^{12}$ join the nitrogen atom in the depicted formula to form a substitient selected from the group consistng of 1-pyrrolidino, 4-methyl-1-homopiperazino, 4-(4-fluorophenyl)-1-piperazino, 4-(2-hydroxyethoxyethyl)-1-piperazino, 4-(2-pyridyl)-1-piperazino, 4-hydroxy-1-piperidino, 4-amino-2,2,6,6-tetramethyl-1-piperidino, 3-ethoxycarbonyl-1-piperidino, 4-(4-methoxyphenyl)-3-methyl-1-piperazino, 4-aminocarbonyl-1-piperidino, heptamethyleneimino, 4-(2-furoyl)-1-piperazino, 4-(3-trifluoromethylphenyl)-1-piperazino, 3-acetamido-1-pyrrolidino, 4-ethoxycarbonyl-1-piperazino, 4-ethoxycarbonyl-1-piperidino and 4-thiomorpholino, or R$^{11}$ and R$^{12}$ are, independently, selected from the group consisting of a hydrogen atom, (1-ethyl-2-pyrrolidinyl)methyl, 2-thiazolyl, 5-methoxycarbonylpentyl, 2-ethoxycarbonylethyl, 3-(methylthio)phenyl, N-methyl-(1-methyl-4-piperidino), 2-(pyridin-2-yl)ethyl, 2-hydroxyethyl, 4-(trifluoromethyl)benzyl, N,N-dimethylaminoethyl, 3-(2-oxo-1-pyrrolidino)propyl, 1-ethoxycarbonyl-4-piperidino, pyridin-2-ylmethyl, bis(2-methoxyethyl), 2-acetylaminoethyl, 3-(methylthio)propyl, 2-(1-morpholino)ethyl, 5-indazolyl, cyclopropyl, N-ethyl-(pyridin-4-ylmethyl), cyclopentyl, cycloheptyl, pyridin-3-ylmethyl, 4-(trifluoromethyl)benzyl, 2-(thien-2-yl)ethyl, 3-(N-pyrrolidino)propyl and 3-(1-imidazolyl)propyl; and $R^7$ is selected from the group consisting of cyclopropylamino, 2-(1-morpholino)ethylamino, piperazino, 2-methyl-4-(3-methylphenyl)-1-piperazino, 4-aminocarbonylpiperidino, 2-(pyridin-2-yl)ethylamino, 2-(N,N-dimethylamino)ethylamino, 3-(aminomethyl)benzylamino, (5-phenyl-1H-1,2,4-triazol-3-yl)thio, 3-(4-morpholino)propylamino, tetrahydrofurfurylamino, 4-(2,5-dimethylphenyl)-1-piperazino, hexamethyleneimino, N-methyl-2-(pyridin-2-yl)ethylamino, 2-(dimethylamino)ethylamino, 4-(aminomethyl)benzylamino, (3-carboxypyridin-6-yl)thio, 2-acetylaminoethylamino, 2-(ethoxycarbonyl)ethylamino, 4-(2,3-dimethylphenyl)-1-piperazino, 4-(2-pyridyl)-1-piperazino, 3-(2-pipecolino)propylamino, 2-aminoethylamino, cyclohexylamino, imidazol-2-ylthio, 4-ethoxycarbonyl-1-piperazino, 3-methylthiopropylamino, 4-(4-fluorophenyl)piperazino, 1-benzyl-3-pyrrolidinoamino, N-methyl-4-piperidylamino, 3-aminopropylamino, N-benzylmethylamino, (3,5-dimethyl-2,6-pyrimidin-2-yl)thio, 4-acetyl-1-piperazino, 2,3-dimethoxybenzylamino, 4-(3,4-dichlorophenyl)-1-piperazino, 3-ethoxycarbonyl-1-piperidino, pyridin-3-ylmethylamino, N-methyl-2-(diethylamino)ethylamino, N-methylphenethylamino, (5-methyl-1,3,4-thiadiazol-2-yl)thio, 8-amino-3,6-dioxaoctyamino, 3-acetamido-1-pyrrolidino, 4-benzyl-1-piperazino, 4-ethoxycarbonyl-1-piperazino, 2-piperadinoethylamino, 3-dimethylaminopropylamino, cycloheptylamino, (1H-1,2,4-triazol-3-yl)thio, 4-ethoxycarbonylmethyl-1-piperazino, 4-(diethylamino)-2-butenylamino, 4-(4-nitrophenyl)-1-piperazino, 1-ethoxycarbonyl-4-piperidylamino, 1-benzyl-4-piperidylamino, N-methyl-3-(dimethylamino)propylamino, 4-(trifluoromethyl)benzylamino, (4-methyl-1,2,4-triazol-3-yl)thio, 2-ethoxyethylamino, tyramino, 4-(3-trifluoromethylphenyl)-1-piperazino, 1,3,3-trimethyl-6-aza-6-bicyclo(3,2,1)octyl, 3,3'-bis(dimethylamino)dipropylamino, butylamino, 3-(trifluoromethyl)benzylamino, pyridin-2-ylthio, 4-(2-furoyl)-1-piperazino, cyclooctylamino, 4-(4-acetylphenyl)-1-piperazino, 4-(4-methylphenyl)-3-methyl-1-piperazino, 2-fluorophenethylamino, 3-fluorophenethylamino, 4-fluorobenzylamino, fluoro, morpholino, thiomorpholino, 4-(5-chloro-2-methylphenyl)-1-piperazino, (1-ethyl-2-pyrrolidino)

methylamino, 2,2,6,6-tetramethyl-4-piperidylamino, diethylamino and 3,3,5-trimethylcyclohexyamino.

10. The single compound of claim 1, wherein:
$R^7$ is selected from the group consisting of hydroxy, protected hydroxy, cyano, $C_1$ to $C_{12}$ alkyl, $C_2$ to $C_{12}$ alkenyl, $C_2$ to $C_{12}$ alkynyl, $C_1$ to $C_{12}$ substituted alkyl, $C_2$ to $C_{12}$ substituted alkenyl, $C_2$ to $C_{12}$ substituted alkynyl, $C_1$ to $C_{12}$ alkoxy, $C_1$ to $C_{12}$ substituted alkoxy, $C_1$ to $C_{12}$ acyloxy, $C_1$ to $C_{12}$ acyl, $C_3$ to $C_7$ cycloalkyl, $C_3$ to $C_7$ substituted cycloalkyl, $C_5$ to $C_7$ cycloalkenyl, $C_5$ to $C_7$ substituted cycloalkenyl, heterocyclic ring, substituted heterocyclic ring, $C_7$ to $C_{18}$ phenylalkyl, $C_7$ to $C_{18}$ substituted phenylalkyl, $C_1$ to $C_{12}$ heterocycloalkyl, $C_1$ to $C_{12}$ substituted heterocycloalkyl, phenyl, substituted phenyl, naphthyl, substituted naphthyl, cyclic $C_2$ to $C_7$ alkylene, substituted cyclic $C_2$ to $C_7$ alkylene, cyclic $C_2$ to $C_7$ heteroalkylene, substituted cyclic $C_2$ to $C_7$ heteroalkylene, carboxy, protected carboxy, hydroxymethyl, protected hydroxymethyl, amino, protected amino, (monosubstituted)amino, protected (monosubstituted)amino, (disubstituted)amino, $C_1$ to $C_{10}$ alkylamino, $C_1$ to $C_{10}$ alkyl protected amino, $C_1$ to $C_{10}$ alkyl (monosubstituted)amino, $C_1$ to $C_{10}$ alkyl, protected (monosubstituted)amino, $C_1$ to $C_{10}$ alkyl (disubstituted)amino, $C_1$ to $C_{10}$ substituted alkylamino, $C_1$ to $C_{10}$ substituted alkyl protected amino, $C_1$ to $C_{10}$ substituted alkyl (monosubstituted)amino, $C_1$ to $C_{10}$ substituted alkyl protected (monosubstituted)amino, $C_1$ to $C_{10}$ substituted alkyl(disubstituted)amino, carboxamide, protected carboxamide, $C_1$ to $C_{10}$ alkylthio, $C_1$ to $C_{10}$ substituted alkylthio, $C_1$ to $C_{10}$ alkylsulfonyl, $C_1$ to $C_{10}$ substituted alkylsulfonyl, $C_1$ to $C_{10}$ alkylsulfoxide, $C_1$ to $C_{10}$ substituted alkylsulfoxide, phenylthio, substituted phenylthio, phenylsulfoxide, substituted phenylsulfoxide, phenylsulfonyl, substituted phenylsulfonyl and and the group consisting of (i) the formula —C(O)NR$^{11}$R$^{12}$, (i) the formula —C(O)R$^{11}$, (iii) the formula —NR$^{11}$R$^{12}$, (iv) the formula —SR$^{11}$, (v) the formula —OR$^{11}$, and (vi) the formula —C(O)OR$^{11}$, wherein $R^{11}$ and $R^{12}$ are, independently, selected from the group consisting of a hydrogen atom, $C_1$ to $C_{12}$ alkyl, $C_1$ to $C_{12}$ substituted alkyl, $C_2$ to $C_{12}$ alkenyl, $C_2$ to $C_{12}$ substituted alkenyl, phenyl, substituted phenyl, naphthyl, substituted naphthyl, $C_7$ to $C_{18}$ phenylalkyl, $C_7$ to $C_{18}$ substituted phenylalkyl, $C_1$ to $C_{12}$ heterocycloalkyl, $C_1$ to $C_{12}$ substituted heterocycloalkyl, heteroaryl, substituted heteroaryl, heterocycle, substituted heterocycle, $C_1$ to $C_{12}$ acyl, $C_1$ to $C_{12}$ substituted acyl, phenylsulfonyl, substituted phenylsulfonyl, $C_1$ to $C_{10}$ alkylsulfonyl, $C_1$ to $C_{10}$ substituted alkylsulfonyl, $C_1$ to $C_{12}$ alkylaminocarbonyl, $C_1$ to $C_{12}$ substituted alkylaminocarbonyl, phenylaminocarbonyl, and substituted phenylaminocarbonyl.

11. The single compound of claim 1, wherein:
$R^1$ is selected from the group consisting of $C_1$ to $C_{12}$ alkyl, $C_1$ to $C_{12}$ substituted alkyl, phenyl, substituted phenyl, $C_7$ to $C_{18}$ phenylalkyl, $C_7$ to $C_{18}$ substituted phenylalkyl, $C_1$ to $C_{12}$ heterocycloalkyl, $C_1$ to $C_{12}$ substituted heterocycloalkyl, heteroaryl, substituted heteroaryl, cyano, $C_1$ to $C_{12}$ acyl, $C_1$ to $C_{12}$ substituted acyl, $C_1$ to $C_{12}$ alkoxycarbonyl, $C_1$ to $C_{12}$ substituted alkoxycarbonyl, $C_1$ to $C_{12}$ alkylaminocarbonyl, $C_1$ to $C_{12}$ substituted alkylaminocarbonyl, phenylaminocarbonyl, substituted phenylaminocarbonyl, $C_1$ to $C_{10}$ alkylthio, $C_1$ to $C_{10}$ substituted alkylthio, $C_1$ to $C_{10}$ alkylsulfonyl, $C_1$ to $C_{10}$ substituted alkylsulfonyl, $C_1$ to $C_{10}$ alkylsulfoxide, $C_1$ to $C_{10}$ substituted alkylsulfoxide, phenylthio, substituted phenylthio, phenylsulfoxide, substituted phenylsulfoxide, phenylsulfonyl, substituted phenylsulfonyl, heterocycle, substituted heterocycle, cyclic $C_2$ to $C_7$ alkylene, substituted cyclic $C_2$ to $C_7$ alkylene, cyclic $C_2$ to $C_7$ heteroalkylene, substituted cyclic $C_2$ to $C_7$ heteroalkylene, naphthyl, substituted naphthyl, $C_5$ to $C_7$ cycloalkyl, $C_5$ to $C_7$ substituted cycloalkyl, $C_5$ to $C_7$ cycloalkenyl and $C_5$ to $C_7$ substituted cycloalkenyl.

12. A single compound of the formula:

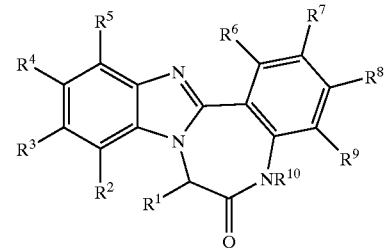

wherein:
$R^1$ is selected from the group consisting of a hydrogen atom, $C_1$ to $C_{12}$ alkyl, $C_1$ to $C_{12}$ substituted alkyl, phenyl, substituted phenyl, $C_7$ to $C_{18}$ phenylalkyl, $C_7$ to $C_{18}$ substituted phenylalkyl, $C_1$ to $C_{12}$ heterocycloalkyl, $C_1$ to $C_{12}$ substituted heterocycloalkyl, heteroaryl, substituted heteroaryl, cyano, $C_1$ to $C_{12}$ acyl, $C_1$ to $C_{12}$ substituted acyl, $C_1$ to $C_{12}$ alkoxycarbonyl, $C_1$ to $C_{12}$ substituted alkoxycarbonyl, $C_1$ to $C_{12}$ alkylaminocarbonyl, $C_1$ to $C_{12}$ substituted alkylaminocarbonyl, phenylaminocarbonyl, substituted phenylaminocarbonyl, $C_1$ to $C_{10}$ alkylthio, $C_1$ to $C_{10}$ substituted alkylthio, $C_1$ to $C_{10}$ alkylsulfonyl, $C_1$ to $C_{10}$ substituted alkylsulfonyl, $C_1$ to $C_{10}$ alkylsulfoxide, $C_1$ to $C_{10}$ substituted alkylsulfoxide, phenylthio, substituted phenylthio, phenylsulfoxide, substituted phenylsulfoxide, phenylsulfonyl, substituted phenylsulfonyl, heterocycle, substituted heterocycle, cyclic $C_2$ to $C_7$ alkylene, substituted cyclic $C_2$ to $C_7$ alkylene, cyclic $C_2$ to $C_7$ heteroalkylene, substituted cyclic $C_2$ to $C_7$ heteroalkylene, naphthyl, substituted naphthyl, $C_5$ to $C_7$ cycloalkyl, $C_5$ to $C_7$ substituted cycloalkyl, $C_5$ to $C_7$ cycloalkenyl and $C_5$ to $C_7$ substituted cycloalkenyl;

$R^2$, $R^3$, $R^4$, $R^5$, $R^6$, $R^8$ and $R^9$ are, independently, selected from the group consisting of a hydrogen atom, halo, hydroxy, protected hydroxy, cyano, $C_1$ to $C_{12}$ alkyl, $C_2$ to $C_{12}$ alkenyl, $C_2$ to $C_{12}$ alkynyl, $C_1$ to $C_{12}$ substituted alkyl, $C_2$ to $C_{12}$ substituted alkenyl, $C_2$ to $C_{12}$ substituted alkynyl, $C_1$ to $C_{12}$ alkoxy, $C_1$ to $C_{12}$ substituted alkoxy, $C_1$ to $C_{12}$ acyloxy, $C_1$ to $C_{12}$ acyl, $C_3$ to $C_7$ cycloalkyl, $C_3$ to $C_7$ substituted cycloalkyl, $C_5$ to $C_7$ cycloalkenyl, $C_5$ to $C_7$ substituted cycloalkenyl, heterocyclic ring, substituted heterocyclic ring, $C_7$ to $C_{18}$ phenylalkyl, $C_7$ to $C_{18}$ substituted phenylalkyl, $C_1$ to $C_{12}$ heterocycloalkyl, $C_1$ to $C_{12}$ substituted heterocycloalkyl, phenyl, substituted phenyl, naphthyl, substituted naphthyl, cyclic $C_2$ to $C_7$ alkylene, substituted cyclic $C_2$ to $C_7$ alkylene, cyclic $C_2$ to $C_7$ heteroalkylene, substituted cyclic $C_2$ to $C_7$ heteroalkylene, carboxy, protected carboxy, hydroxymethyl, protected hydroxymethyl, amino, protected amino, (monosubstituted)amino, protected (monosubstituted)amino, (disubstituted)amino, $C_1$ to $C_{10}$ alkylamino, $C_1$ to $C_{10}$ alkyl protected amino, $C_1$ to $C_{10}$ alkyl (monosubstituted)amino, $C_1$ to $C_{10}$ alkyl, protected (monosubstituted)amino, $C_1$ to $C_{10}$ alkyl (disubstituted)amino, $C_1$ to $C_{10}$ substituted alkylamino, $C_1$ to $C_{10}$ substituted alkyl protected amino, $C_1$ to $C_{10}$ substituted alkyl (monosubstituted)amino, $C_1$ to $C_{10}$ substituted alkyl protected (monosubstituted)amino, $C_1$ to $C_{10}$ substituted alkyl(disubstituted)amino, carboxamide, protected carboxamide, $C_1$ to $C_{10}$ alkylthio, $C_1$ to $C_{10}$ substituted alkylthio, $C_1$ to $C_{10}$ alkylsulfonyl, $C_1$ to $C_{10}$ substituted alkylsulfonyl, $C_1$ to $C_{10}$ alkylsulfoxide, $C_1$ to $C_{10}$ substituted alkylsulfoxide, phenylthio, substituted phenylthio, phenylsulfoxide, substituted phenylsulfoxide, phenylsulfonyl, substituted phenylsulfonyl and and the group consisting of (i) the formula —$C(O)NR^{11}R^{12}$, (i) the formula —$C(O)R^{11}$, (iii) the formula —$NR^{11}R^{12}$, (iv) the formula —$SR^{11}$, (v) the formula —$OR^{11}$ and (vi) the formula —$C(O)OR^{11}$, wherein $R^{11}$ and $R^{12}$ are, independently, selected from the group consisting of a hydrogen atom, $C_1$ to $C_{12}$ alkyl, $C_1$ to $C_{12}$ substituted alkyl, $C_2$ to $C_{12}$ alkenyl, $C_2$ to $C_{12}$ substituted alkenyl, phenyl, substituted phenyl, naphthyl, substituted naphthyl, $C_7$ to $C_{18}$ phenylalkyl, $C_7$ to $C_{18}$ substituted phenylalkyl, $C_1$ to $C_{12}$ heterocycloalkyl, $C_1$ to $C_{12}$ substituted heterocycloalkyl, heteroaryl, substituted heteroaryl, heterocycle, substituted heterocycle, $C_1$ to $C_{12}$ acyl, $C_1$ to $C_{12}$ substituted acyl, phenylsulfonyl, substituted phenylsulfonyl, $C_1$ to $C_{10}$ alkylsulfonyl, $C_1$ to $C_{10}$ substituted alkylsulfonyl, $C_1$ to $C_{12}$ alkylaminocarbonyl, $C_1$ to $C_{12}$ substituted alkylaminocarbonyl, phenylaminocarbonyl, and substituted phenylaminocarbonyl;

or, where $R^2$, $R^3$, $R^4$ or $R^5$ is the formula —$C(O)NR^{11}R^{12}$, $R^{11}$ and $R^{12}$ join the nitrogen atom in the formula to form a heterocycle or substituted heterocycle;

$R^7$ is selected from the group consisting of heterocycle, substituted heterocycle and (i) the formula —$C(O)NR^{11}R^{12}$, (i) the formula —$C(O)R^{11}$, (iii) the formula —$NR^{11}R^{12}$, (iv) the formula —$SR^{11}$, (v) the formula —$OR^{11}$, and (vi) the formula —$C(O)OR^{11}$, wherein $R^{11}$ and $R^{12}$ are, independently, selected from the group consisting of a hydrogen atom, $C_1$ to $C_{12}$ alkyl, $C_1$ to $C_{12}$ substituted alkyl, $C_2$ to $C_{12}$ alkenyl, $C_2$ to $C_{12}$ substituted alkenyl, phenyl, substituted phenyl, naphthyl, substituted naphthyl, $C_7$ to $C_{18}$ phenylalkyl, $C_7$ to $C_{18}$ substituted phenylalkyl, $C_1$ to $C_{12}$ heterocycloalkyl, $C_1$ to $C_{12}$ substituted heterocycloalkyl, heteroaryl, substituted heteroaryl, heterocycle, substituted heterocycle, $C_1$ to $C_{12}$ acyl, $C_1$ to $C_{12}$ substituted acyl, phenylsulfonyl, substituted phenylsulfonyl, $C_1$ to $C_{10}$ alkylsulfonyl, $C_1$ to $C_{10}$ substituted alkylsulfonyl, $C_1$ to $C_{12}$ alkylaminocarbonyl, $C_1$ to $C_{12}$ substituted alkylaminocarbonyl, phenylaminocarbonyl, and substituted phenylaminocarbonyl; and $R^{10}$ is selected from the group consisting of a hydrogen atom, $C_1$ to $C_{12}$ alkyl, $C_1$ to $C_{12}$ substituted alkyl, $C_2$ to $C_{12}$ alkenyl, $C_2$ to $C_{12}$ substituted alkenyl, $C_7$ to $C_{18}$ phenylalkyl, $C_7$ to $C_{18}$ substituted phenylalkyl, $C_1$ to $C_{12}$ heterocycloalkyl and $C_1$ to $C_{12}$ substituted heterocycloalkyl; or a pharmaceutically acceptable salt of a compound thereof.

13. The single compound of claim 12, wherein $R^1$ is selected from the group consisting of a hydrogen atom, methyl, 2-propyl, 2-butyl, aminocarbonylethyl, 2-methylmercaptoethyl, phenyl, benzyl, cyclohexylmethyl, 4-methoxybenzyl, 4-chlorobenzyl, 3-indolylmethyl, 4-(trifluoroacetyl)aminobutyl and 3-guanidinopropyl;

$R^2$, $R^3$, $R^4$ and $R^5$ are, independently, selected from the group consisitng of a hydrogen atom, methyl, carboxy, bromo, fluoro, chloro and trifluoromethyl;

$R^6$, $R^8$, $R^9$ and $R^{10}$ are each a hydrogen atom; and $R^7$ is selected from the group consisting of cyclopropylamino, 2-(1-morpholino)ethylamino, piperazino, 2-methyl-4-(3-methylphenyl)-1-piperazino, 4-aminocarbonylpiperidino, 2-(pyridin-2-yl)ethylamino, 2-(N,N-dimethylamino)ethylamino, 3-(aminomethyl)benzylamino, (5-phenyl-1H-1,2,4-triazol-3-yl)thio, 3-(4-morpholino)propylamino, tetrahydrofurfurylamino, 4-(2,5-dimethylphenyl)-1-piperazino, hexamethyleneimino, N-methyl-2-(pyridin-2-yl)ethylamino, 2-(dimethylamino)ethylamino, 4-(aminomethyl)benzylamino, (3-carboxypyridin-6-yl)thio, 2-acetylaminoethylamino, 2-(ethoxycarbonyl)ethylamino, 4-(2,3-dimethylphenyl)-1-piperazino, 4-(2-pyridyl)-1-piperazino, 3-(2-pipecolino)propylamino, 2-aminoethylamino, cyclohexylamino, imidazol-2-ylthio, 4-ethoxycarbonyl-1-piperazino, 3-methylthiopropylamino, 4-(4-fluorophenyl)piperazino, 1-benzyl-3-pyrrolidinoamino, N-methyl-4-piperidylamino, 3-aminopropylamino, N-benzylmethylamino, (3,5-dimethyl-2,6-pyrimidin-2-yl)thio, 4-acetyl-1-piperazino, 2,3-dimethoxybenzylamino, 4-(3,4-dichlorophenyl)-1-piperazino, 3-ethoxycarbonyl-1-piperidino, pyridin-3-ylmethylamino, N-methyl-2-(diethylamino)ethylamino, N-methylphenethylamino, (5-methyl-1,3,4-thiadiazol-2-yl)thio, 8-amino-3,6-dioxaoctyamino, 3-acetamido-1-pyrrolidino, 4-benzyl-1-piperazino, 4-ethoxycarbonyl-1-piperazino, 2-piperadinoethylamino, 3-dimethylaminopropylamino, cycloheptylamino, (1H-1,2,4-triazol-3-yl)thio, 4-ethoxycarbonylmethyl-1-piperazino, 4-(diethylamino)-2-butenylamino, 4-(4-nitrophenyl)-1-piperazino, 1-ethoxycarbonyl-4-piperidylamino, 1-benzyl-4-piperidylamino, N-methyl-3-(dimethylamino)propylamino, 4-(trifluoromethyl)benzylamino, (4-methyl-1,2,4-triazol-3-yl)thio, 2-ethoxyethylamino, tyramino, 4-(3-trifluoromethylphenyl)-1-piperazino, 1,3,3-trimethyl-6-aza-6-bicyclo(3,2,1)octyl, 3,3'-bis(dimethylamino)dipropylamino, butylamino, 3-(trifluoromethyl)benzylamino, pyridin-2-ylthio, 4-(2-furoyl)-1-piperazino, cyclooctylamino, 4-(4-acetylphenyl)-1-piperazino, 4-(4-methylphenyl)-3-methyl-1-piperazino, 2-fluorophenethylamino, 3-fluorophenethylamino, 4-fluorobenzylamino, morpholino, thiomorpholino, 4-(5-chloro-2-methylphenyl)-1-piperazino, (1-ethyl-2-pyrrolidino)methylamino, 2,2,6,6-tetramethyl-4-piperidylamino, diethylamino and 3,3,5-trimethylcyclohexyamino.

14. The single compound of claim 12, wherein:

$R^7$ is selected from the group consisting of heterocycle, substituted heterocycle and (i) the formula —$NR^{11}R^{12}$ and (iv) the formula —$SR^{11}$, wherein $R^{11}$ and $R^{12}$ are, independently, selected from the group consisting of a hydrogen atom, $C_1$ to $C_{12}$ alkyl, $C_1$ to $C_{12}$ substituted alkyl, $C_2$ to $C_{12}$ alkenyl, $C_2$ to $C_{12}$ substituted alkenyl, phenyl, substituted phenyl, naphthyl, substituted naphthyl, C₇ to C₁₈ phenylalkyl, C₇ to C₁₈ substituted phenylalkyl, C₁ to C₁₂ heterocycloalkyl, C₁ to C₁₂ substituted heterocycloalkyl, heteroaryl, substituted heteroaryl, heterocycle, substituted heterocycle, C₁ to C₁₂ acyl, C₁ to C₁₂ substituted acyl, phenylsulfonyl, substituted phenylsulfonyl, C₁ to C₁₀ alkylsulfonyl, C₁ to C₁₀ substituted alkylsulfonyl, C₁ to C₁₂ alkylaminocarbonyl, C₁ to C₁₂ substituted alkylaminocarbonyl, phenylaminocarbonyl, and substituted phenylaminocarbonyl.

15. A single compound of the formula:

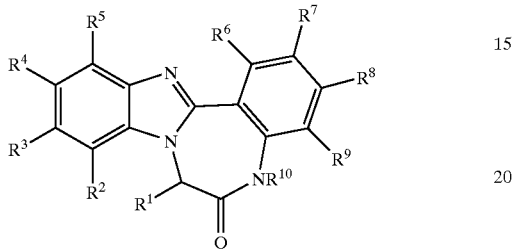

wherein:

R¹ is selected from the group consisting of C₁ to C₁₂ alkyl, C₁ to C₁₂ substituted alkyl, phenyl, substituted phenyl, C₇ to C₁₈ phenylalkyl, C₇ to C₁₈ substituted phenylalkyl, C₁ to C₁₂ heterocycloalkyl, C₁ to C₁₂ substituted heterocycloalkyl, heteroaryl, substituted heteroaryl, cyano, C₁ to C₁₂ acyl, C₁ to C₁₂ substituted acyl, C₁ to C₁₂ alkoxycarbonyl, C₁ to C₁₂ substituted alkoxycarbonyl, C₁ to C₁₂ alkylaminocarbonyl, C₁ to C₁₂ substituted alkylaminocarbonyl, phenylaminocarbonyl, substituted phenylaminocarbonyl, C₁ to C₁₀ alkylthio, C₁ to C₁₀ substituted alkylthio, C₁ to C₁₀ alkylsulfonyl, C₁ to C₁₀ substituted alkylsulfonyl, C₁ to C₁₀ alkylsulfoxide, C₁ to C₁₀ substituted alkylsulfoxide, phenylthio, substituted phenylthio, phenylsulfoxide, substituted phenylsulfoxide, phenylsulfonyl, substituted phenylsulfonyl, heterocycle, substituted heterocycle, cyclic C₂ to C₇ alkylene, substituted cyclic C₂ to C₇ alkylene, cyclic C₂ to C₇ heteroalkylene, substituted cyclic C₂ to C₇ heteroalkylene, naphthyl, substituted naphthyl, C₅ to C₇ cycloalkyl, C₅ to C₇ substituted cycloalkyl, C₅ to C₇ cycloalkenyl and C₅ to C₇ substituted cycloalkenyl;

R², R³, R⁴, R⁵, R⁶, R⁸ and R⁹ are, independently, selected from the group consisting of a hydrogen atom, halo, hydroxy, protected hydroxy, cyano, C₁ to C₁₂ alkyl, C₂ to C₁₂ alkenyl, C₂ to C₁₂ alkynyl, C₁ to C₁₂ substituted alkyl, C₂ to C₁₂ substituted alkenyl, C₂ to C₁₂ substituted alkynyl, C₁ to C₁₂ alkoxy, C₁ to C₁₂ substituted alkoxy, C₁ to C₁₂ acyloxy, C₁ to C₁₂ acyl, C₃ to C₇ cycloalkyl, C₃ to C₇ substituted cycloalkyl, C₅ to C₇ cycloalkenyl, C₅ to C₇ substituted cycloalkenyl, heterocyclic ring, substituted heterocyclic ring, C₇ to C₁₈ phenylalkyl, C₇ to C₁₈ substituted phenylalkyl, C₁ to C₁₂ heterocycloalkyl, C₁ to C₁₂ substituted heterocycloalkyl, phenyl, substituted phenyl, naphthyl, substituted naphthyl, cyclic C₂ to C₇ alkylene, substituted cyclic C₂ to C₇ alkylene, cyclic C₂ to C₇ heteroalkylene, substituted cyclic C₂ to C₇ heteroalkylene, carboxy, protected carboxy, hydroxymethyl, protected hydroxymethyl, amino, protected amino, (monosubstituted)amino, protected (monosubstituted)amino, (disubstituted)amino, C₁ to C₁₀ alkylamino, C₁ to C₁₀ alkyl protected amino, C₁ to C₁₀ alkyl (monosubstituted)amino, C₁ to C₁₀ alkyl, protected (monosubstituted)amino, C₁ to C₁₀ alkyl (disubstituted)amino, C₁ to C₁₀ substituted alkylamino, C₁ to C₁₀ substituted alkyl protected amino, C₁ to C₁₀ substituted alkyl (monosubstituted)amino, C₁ to C₁₀ substituted alkyl protected (monosubstituted)amino, C₁ to C₁₀ substituted alkyl(disubstituted)amino, carboxamide, protected carboxamide, C₁ to C₁₀ alkylthio, C₁ to C₁₀ substituted alkylthio, C₁ to C₁₀ alkylsulfonyl, C₁ to C₁₀ substituted alkylsulfonyl, C₁ to C₁₀ alkylsulfoxide, C₁ to C₁₀ substituted alkylsulfoxide, phenylthio, substituted phenylthio, phenylsulfoxide, substituted phenylsulfoxide, phenylsulfonyl, substituted phenylsulfonyl and and the group consisting of (i) the formula —C(O)NR¹¹R¹², (i) the formula —C(O)R¹¹, (iii) the formula —NR¹¹R¹², (iv) the formula —SR¹¹, (v) the formula —OR¹¹ and (vi) the formula —C(O)OR¹¹, wherein R¹¹ and R¹² are, independently, selected from the group consisting of a hydrogen atom, C₁ to C₁₂ alkyl, C₁ to C₁₂ substituted alkyl, C₂ to C₁₂ alkenyl, C₂ to C₁₂ substituted alkenyl, phenyl, substituted phenyl, naphthyl, substituted naphthyl, C₇ to C₁₈ phenylalkyl, C₇ to C₁₈ substituted phenylalkyl, C₁ to C₁₂ heterocycloalkyl, C₁ to C₁₂ substituted heterocycloalkyl, heteroaryl, substituted heteroaryl, heterocycle, substituted heterocycle, C₁ to C₁₂ acyl, C₁ to C₁₂ substituted acyl, phenylsulfonyl, substituted phenylsulfonyl, C₁ to C₁₀ alkylsulfonyl, C₁ to C₁₀ substituted alkylsulfonyl, C₁ to C₁₂ alkylaminocarbonyl, C₁ to C₁₂ substituted alkylaminocarbonyl, phenylaminocarbonyl, and substituted phenylaminocarbonyl;

or, where R², R³, R⁴ or R⁵ is the formula —C(O)NR¹¹R¹², R¹¹ and R¹² join the nitrogen atom in the formula to form a heterocycle or substituted heterocycle;

R⁷ is selected from the group consisting of hydroxy, protected hydroxy, cyano, C₁ to C₁₂ alkyl, C₂ to C₁₂ alkenyl, C₂ to C₁₂ alkynyl, C₁ to C₁₂ substituted alkyl, C₂ to C₁₂ substituted alkenyl, C₂ to C₁₂ substituted alkynyl, C₁ to C₁₂ alkoxy, C₁ to C₁₂ substituted alkoxy, C₁ to C₁₂ acyloxy, C₁ to C₁₂ acyl, C₃ to C₇ cycloalkyl, C₃ to C₇ substituted cycloalkyl, C₅ to C₇ cycloalkenyl, C₅ to C₇ substituted cycloalkenyl, heterocyclic ring, substituted heterocyclic ring, C₇ to C₁₈ phenylalkyl, C₇ to C₁₈ substituted phenylalkyl, C₁ to C₁₂ heterocycloalkyl, C₁ to C₁₂ substituted heterocycloalkyl, phenyl, substituted phenyl, naphthyl, substituted naphthyl, cyclic C₂ to C₇ alkylene, substituted cyclic C₂ to C₇ alkylene, cyclic C₂ to C₇ heteroalkylene, substituted cyclic C₂ to C₇ heteroalkylene, carboxy, protected carboxy, hydroxymethyl, protected hydroxymethyl, amino, protected amino, (monosubstituted)amino, protected (monosubstituted)amino, (disubstituted)amino, C₁ to C₁₀ alkylamino, C₁ to C₁₀ alkyl protected amino, C₁ to C₁₀ alkyl (monosubstituted)amino, C₁ to C₁₀ alkyl, protected (monosubstituted)amino, C₁ to C₁₀ alkyl (disubstituted)amino, C₁ to C₁₀ substituted alkylamino, C₁ to C₁₀ substituted alkyl protected amino, C₁ to C₁₀ substituted alkyl (monosubstituted)amino, C₁ to C₁₀ substituted alkyl protected (monosubstituted)amino, C₁ to C₁₀ substituted alkyl(disubstituted)amino, carboxamide, protected carboxamide, C₁ to C₁₀ alkylthio, C₁ to C₁₀ substituted alkylthio, C₁ to C₁₀ alkylsulfonyl, C₁ to C₁₀ substituted alkylsulfonyl, C₁ to $C_{10}$ alkylsulfoxide, $C_1$ to $C_{10}$ substituted alkylsulfoxide, phenylthio, substituted phenylthio, phenylsulfoxide, substituted phenylsulfoxide, phenylsulfonyl, substituted phenylsulfonyl and and the group consisting of (i) the formula —C(O)NR$^{11}$R$^{12}$, (i) the formula —C(O)R$^{11}$, (iii) the formula —NR$^{11}$R$^{12}$, (iv) the formula —SR$^{11}$, (v) the formula —OR$^{11}$, and (vi) the formula —C(O)OR$^{11}$, wherein R$^{11}$ and R$^{12}$ are, independently, selected from the group consisting of a hydrogen atom, $C_1$ to $C_{12}$ alkyl, $C_1$ to $C_{12}$ substituted alkyl, $C_2$ to $C_{12}$ alkenyl, $C_2$ to $C_{12}$ substituted alkenyl, phenyl, substituted phenyl, naphthyl, substituted naphthyl, $C_7$ to $C_{18}$ phenylalkyl, $C_7$ to $C_{18}$ substituted phenylalkyl, $C_1$ to $C_{12}$ heterocycloalkyl, $C_1$ to $C_{12}$ substituted heterocycloalkyl, heteroaryl, substituted heteroaryl, heterocycle, substituted heterocycle, $C_1$ to $C_{12}$ acyl, $C_1$ to $C_{12}$ substituted acyl, phenylsulfonyl, substituted phenylsulfonyl, $C_1$ to $C_{10}$ alkylsulfonyl, $C_1$ to $C_{10}$ substituted alkylsulfonyl, $C_1$ to $C_{12}$ alkylaminocarbonyl, $C_1$ to $C_{12}$ substituted alkylaminocarbonyl, phenylaminocarbonyl, and substituted phenylaminocarbonyl; and R$^{10}$ is selected from the group consisting of a hydrogen atom, $C_1$ to $C_{12}$ alkyl, $C_1$ to $C_{12}$ substituted alkyl, $C_2$ to $C_{12}$ alkenyl, $C_2$ to $C_{12}$ substituted alkenyl, $C_7$ to $C_{18}$ phenylalkyl, $C_7$ to $C_{18}$ substituted phenylalkyl, $C_1$ to $C_{12}$ heterocycloalkyl and $C_1$ to $C_{12}$ substituted heterocycloalkyl; or a pharmaceutically acceptable salt of a compound thereof.

16. A single compound of the formula:

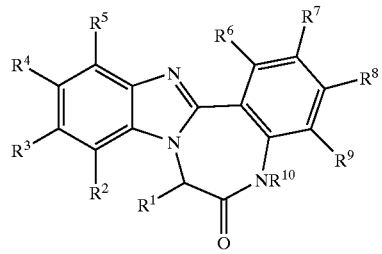

wherein:

R$^1$ is selected from the group consisting of a hydrogen atom, $C_1$ to $C_{12}$ alkyl, $C_1$ to $C_{12}$ substituted alkyl, phenyl, substituted phenyl, $C_7$ to $C_{18}$ phenylalkyl, $C_7$ to $C_{18}$ substituted phenylalkyl, $C_1$ to $C_{12}$ heterocycloalkyl, $C_1$ to $C_{12}$ substituted heterocycloalkyl, heteroaryl, substituted heteroaryl, cyano, $C_1$ to $C_{12}$ acyl, $C_1$ to $C_{12}$ substituted acyl, $C_1$ to $C_{12}$ alkoxycarbonyl, $C_1$ to $C_{12}$ substituted alkoxycarbonyl, $C_1$ to $C_{12}$ alkylaminocarbonyl, $C_1$ to $C_{12}$ substituted alkylaminocarbonyl, phenylaminocarbonyl, substituted phenylaminocarbonyl, $C_1$ to $C_{10}$ alkylthio, $C_1$ to $C_{10}$ substituted alkylthio, $C_1$ to $C_{10}$ alkylsulfonyl, $C_1$ to $C_{10}$ substituted alkylsulfonyl, $C_1$ to $C_{10}$ alkylsulfoxide, $C_1$ to $C_{10}$ substituted alkylsulfoxide, phenylthio, substituted phenylthio, phenylsulfoxide, substituted phenylsulfoxide, phenylsulfonyl, substituted phenylsulfonyl, heterocycle, substituted heterocycle, cyclic $C_2$ to $C_7$ alkylene, substituted cyclic $C_2$ to $C_7$ alkylene, cyclic $C_2$ to $C_7$ heteroalkylene, substituted cyclic $C_2$ to $C_7$ heteroalkylene, naphthyl, substituted naphthyl, $C_5$ to $C_7$ cycloalkyl, $C_5$ to $C_7$ substituted cycloalkyl, $C_5$ to $C_7$ cycloalkenyl and $C_5$ to $C_7$ substituted cycloalkenyl;

one of R$^3$ and R$^4$ is selected from the group consisting of halo, hydroxy, protected hydroxy, cyano, $C_1$ to $C_{12}$ alkyl, $C_2$ to $C_{12}$ alkenyl, $C_2$ to $C_{12}$ alkynyl, $C_1$ to $C_{12}$ substituted alkyl, $C_2$ to $C_{12}$ substituted alkenyl, $C_2$ to $C_{12}$ substituted alkynyl, $C_1$ to $C_{12}$ alkoxy, $C_1$ to $C_{12}$ substituted alkoxy, $C_1$ to $C_{12}$ acyloxy, $C_1$ to $C_{12}$ acyl, $C_3$ to $C_7$ cycloalkyl, $C_3$ to $C_7$ substituted cycloalkyl, $C_5$ to $C_7$ cycloalkenyl, $C_5$ to $C_7$ substituted cycloalkenyl, heterocyclic ring, substituted heterocyclic ring, $C_7$ to $C_{18}$ phenylalkyl, $C_7$ to $C_{18}$ substituted phenylalkyl, $C_1$ to $C_{12}$ heterocycloalkyl, $C_1$ to $C_{12}$ substituted heterocycloalkyl, phenyl, substituted phenyl, naphthyl, substituted naphthyl, cyclic $C_2$ to $C_7$ alkylene, substituted cyclic $C_2$ to $C_7$ alkylene, cyclic $C_2$ to $C_7$ heteroalkylene, substituted cyclic $C_2$ to $C_7$ heteroalkylene, carboxy, protected carboxy, hydroxymethyl, protected hydroxymethyl, amino, protected amino, (monosubstituted)amino, protected (monosubstituted)amino, (disubstituted)amino, $C_1$ to $C_{10}$ alkylamino, $C_1$ to $C_{10}$ alkyl protected amino, $C_1$ to $C_{10}$ alkyl (monosubstituted)amino, $C_1$ to $C_{10}$ alkyl, protected (monosubstituted)amino, $C_1$ to $C_{10}$ alkyl (disubstituted)amino, $C_1$ to $C_{10}$ substituted alkylamino, $C_1$ to $C_{10}$ substituted alkyl protected amino, $C_1$ to $C_{10}$ substituted alkyl (monosubstituted)amino, $C_1$ to $C_{10}$ substituted alkyl protected (monosubstituted)amino, $C_1$ to $C_{10}$ substituted alkyl(disubstituted)amino, carboxamide, protected carboxamide, $C_1$ to $C_{10}$ alkylthio, $C_1$ to $C_{10}$ substituted alkylthio, $C_1$ to $C_{10}$ alkylsulfonyl, $C_1$ to $C_{10}$ substituted alkylsulfonyl, $C_1$ to $C_{10}$ alkylsulfoxide, $C_1$ to $C_{10}$ substituted alkylsulfoxide, phenylthio, substituted phenylthio, phenylsulfoxide, substituted phenylsulfoxide, phenylsulfonyl, substituted phenylsulfonyl and and the group consisting of (i) the formula —C(O)NR$^{11}$R$^{12}$, (i) the formula —C(O)R$^{11}$, (iii) the formula —NR$^{11}$R$^{12}$, (iv) the formula —SR$^{11}$, (v) the formula —OR$^{11}$ and (vi) the formula —C(O)OR$^{11}$, wherein R$^{11}$ and R$^{12}$ are, independently, selected from the group consisting of a hydrogen atom, $C_1$ to $C_{12}$ alkyl, $C_1$ to $C_{12}$ substituted alkyl, $C_2$ to $C_{12}$ alkenyl, $C_2$ to $C_{12}$ substituted alkenyl, phenyl, substituted phenyl, naphthyl, substituted naphthyl, $C_7$ to $C_{18}$ phenylalkyl, $C_7$ to $C_{18}$ substituted phenylalkyl, $C_1$ to $C_{12}$ heterocycloalkyl, $C_1$ to $C_{12}$ substituted heterocycloalkyl, heteroaryl, substituted heteroaryl, heterocycle, substituted heterocycle, $C_1$ to $C_{12}$ acyl, $C_1$ to $C_{12}$ substituted acyl, phenylsulfonyl, substituted phenylsulfonyl, $C_1$ to $C_{10}$ alkylsulfonyl, $C_1$ to $C_{10}$ substituted alkylsulfonyl, $C_1$ to $C_{12}$ alkylaminocarbonyl, $C_1$ to $C_{12}$ substituted alkylaminocarbonyl, phenylaminocarbonyl, and substituted phenylaminocarbonyl, or, in the formula —C(O) NR$^{11}$R$^{12}$, R$^{11}$ and R$^{12}$ join the nitrogen atom in the formula to form a heterocycle or substituted heterocycle;

the other of R$^3$ and R$^4$, and R$^2$, R$^5$, R$^6$, R$^8$ and R$^9$ are, independently, selected from the group consisting of a hydrogen atom, halo, hydroxy, protected hydroxy, cyano, $C_1$ to $C_{12}$ alkyl, $C_2$ to $C_{12}$ alkenyl, $C_2$ to $C_{12}$ alkynyl, $C_1$ to $C_{12}$ substituted alkyl, $C_2$ to $C_{12}$ substituted alkenyl, $C_2$ to $C_{12}$ substituted alkynyl, $C_1$ to $C_{12}$ alkoxy, $C_1$ to $C_{12}$ substituted alkoxy, $C_1$ to $C_{12}$ acyloxy, $C_1$ to $C_{12}$ acyl, $C_3$ to $C_7$ cycloalkyl, $C_3$ to $C_7$ substituted cycloalkyl, $C_5$ to $C_7$ cycloalkenyl, $C_5$ to $C_7$ substituted cycloalkenyl, heterocyclic ring, substituted heterocyclic ring, $C_7$ to $C_{18}$ phenylalkyl, $C_7$ to $C_{18}$ substituted phenylalkyl, $C_1$ to $C_{12}$ heterocycloalkyl, $C_1$ to $C_{12}$ substituted heterocycloalkyl, phenyl, substituted phenyl, naphthyl, substituted naphthyl, cyclic $C_2$ to $C_7$ alkylene, substituted cyclic $C_2$ to $C_7$ alkylene, cyclic $C_2$ to $C_7$ heteroalkylene, substituted cyclic $C_2$ to $C_7$ heteroalkylene, carboxy, protected carboxy, hydroxymethyl, protected hydroxymethyl, amino, protected amino, (monosubstituted)amino, protected (monosubstituted)amino, (disubstituted)amino, $C_1$ to $C_{10}$ alkylamino, $C_1$ to $C_{10}$ alkyl protected amino, $C_1$ to $C_{10}$ alkyl (monosubstituted)amino, $C_1$ to $C_{10}$ alkyl, protected (monosubstituted)amino, $C_1$ to $C_{10}$ alkyl (disubstituted)amino, $C_1$ to $C_{10}$ substituted alkylamino, $C_1$ to $C_{10}$ substituted alkyl protected amino, $C_1$ to $C_{10}$ substituted alkyl (monosubstituted)amino, $C_1$ to $C_{10}$ substituted alkyl protected (monosubstituted)amino, $C_1$ to $C_{10}$ substituted alkyl(disubstituted)amino, carboxamide, protected carboxamide, $C_1$ to $C_{10}$ alkylthio, $C_1$ to $C_{10}$ substituted alkylthio, $C_1$ to $C_{10}$ alkylsulfonyl, $C_1$ to $C_{10}$ substituted alkylsulfonyl, $C_1$ to $C_{10}$ alkylsulfoxide, $C_1$ to $C_{10}$ substituted alkylsulfoxide, phenylthio, substituted phenylthio, phenylsulfoxide, substituted phenylsulfoxide, phenylsulfonyl, substituted phenylsulfonyl and and the group consisting of (i) the formula —C(O)NR$^{11}$R$^{12}$, (i) the formula —C(O)R$^{11}$, (iii) the formula —NR$^{11}$R$^{12}$, (iv) the formula —SR$^{11}$, (v) the formula —OR$^{11}$ and (vi) the formula —C(O)OR$^{11}$, wherein R$^{11}$ and R$^{12}$ are, independently, selected from the group consisting of a hydrogen atom, $C_1$ to $C_{12}$ alkyl, $C_1$ to $C_{12}$ substituted alkyl, $C_2$ to $C_{12}$ alkenyl, $C_2$ to $C_{12}$ substituted alkenyl, phenyl, substituted phenyl, naphthyl, substituted naphthyl, $C_7$ to $C_{18}$ phenylalkyl, $C_7$ to $C_{18}$ substituted phenylalkyl, $C_1$ to $C_{12}$ heterocycloalkyl, $C_1$ to $C_{12}$ substituted heterocycloalkyl, heteroaryl, substituted heteroaryl, heterocycle, substituted heterocycle, $C_1$ to $C_{12}$ acyl, $C_1$ to $C_{12}$ substituted acyl, phenylsulfonyl, substituted phenylsulfonyl, $C_1$ to $C_{10}$ alkylsulfonyl, $C_1$ to $C_{10}$ substituted alkylsulfonyl, $C_1$ to $C_{12}$ alkylaminocarbonyl, $C_1$ to $C_{12}$ substituted alkylaminocarbonyl, phenylaminocarbonyl, and substituted phenylaminocarbonyl;

or, where R$^2$, R$^3$, R$^4$ or R$^5$ is the formula —C(O)NR$^{11}$R$^{12}$, R$^{11}$ and R$^{12}$ join the nitrogen atom in the formula to form a heterocycle or substituted heterocycle;

R$^7$ is selected from the group consisting of a halo, hydroxy, protected hydroxy, cyano, $C_1$ to $C_{12}$ alkyl, $C_2$ to $C_{12}$ alkenyl, $C_2$ to $C_{12}$ alkynyl, $C_1$ to $C_{12}$ substituted alkyl, $C_2$ to $C_{12}$ substituted alkenyl, $C_2$ to $C_{12}$ substituted alkynyl, $C_1$ to $C_{12}$ alkoxy, $C_1$ to $C_{12}$ substituted alkoxy, $C_1$ to $C_{12}$ acyloxy, $C_1$ to $C_{12}$ acyl, $C_3$ to $C_7$ cycloalkyl, $C_3$ to $C_7$ substituted cycloalkyl, $C_5$ to $C_7$ cycloalkenyl, $C_5$ to $C_7$ substituted cycloalkenyl, heterocyclic ring, substituted heterocyclic ring, $C_7$ to $C_{18}$ phenylalkyl, $C_7$ to $C_{18}$ substituted phenylalkyl, $C_1$ to $C_{12}$ heterocycloalkyl, $C_1$ to $C_{12}$ substituted heterocycloalkyl, phenyl, substituted phenyl, naphthyl, substituted naphthyl, cyclic $C_2$ to $C_7$ alkylene, substituted cyclic $C_2$ to $C_7$ alkylene, cyclic $C_2$ to $C_7$ heteroalkylene, substituted cyclic $C_2$ to $C_7$ heteroalkylene, carboxy, protected carboxy, hydroxymethyl, protected hydroxymethyl, amino, protected amino, (monosubstituted)amino, protected (monosubstituted)amino, (disubstituted)amino, $C_1$ to $C_{10}$ alkylamino, $C_1$ to $C_{10}$ alkyl protected amino, $C_1$ to $C_{10}$ alkyl (monosubstituted)amino, $C_1$ to $C_{10}$ alkyl, protected (monosubstituted)amino, $C_1$ to $C_{10}$ alkyl (disubstituted)amino, $C_1$ to $C_{10}$ substituted alkylamino, $C_1$ to $C_{10}$ substituted alkyl protected amino, $C_1$ to $C_{10}$ substituted alkyl (monosubstituted)amino, $C_1$ to $C_{10}$ substituted alkyl protected (monosubstituted)amino, $C_1$ to $C_{10}$ substituted alkyl(disubstituted)amino, carboxamide, protected carboxamide, $C_1$ to $C_{10}$ alkylthio, $C_1$ to $C_{10}$ substituted alkylthio, $C_1$ to $C_{10}$ alkylsulfonyl, $C_1$ to $C_{10}$ substituted alkylsulfonyl, $C_1$ to $C_{10}$ alkylsulfoxide, $C_1$ to $C_{10}$ substituted alkylsulfoxide, phenylthio, substituted phenylthio, phenylsulfoxide, substituted phenylsulfoxide, phenylsulfonyl, substituted phenylsulfonyl and and the group consisting of (i) the formula —C(O)NR$^{11}$R$^{12}$, (i) the formula —C(O)R$^{11}$, (iii) the formula —NR$^{11}$R$^{12}$, (iv) the formula —SR$^{11}$, (v) the formula —OR$^{11}$, and (vi) the formula —C(O)OR$^{11}$, wherein R$^{11}$ and R$^{12}$ are, independently, selected from the group consisting of a hydrogen atom, $C_1$ to $C_{12}$ alkyl, $C_1$ to $C_{12}$ substituted alkyl, $C_2$ to $C_{12}$ alkenyl, $C_2$ to $C_{12}$ substituted alkenyl, phenyl, substituted phenyl, naphthyl, substituted naphthyl, $C_7$ to $C_{18}$ phenylalkyl, $C_7$ to $C_{18}$ substituted phenylalkyl, $C_1$ to $C_{12}$ heterocycloalkyl, $C_1$ to $C_{12}$ substituted heterocycloalkyl, heteroaryl, substituted heteroaryl, heterocycle, substituted heterocycle, $C_1$ to $C_{12}$ acyl, $C_1$ to $C_{12}$ substituted acyl, phenylsulfonyl, substituted phenylsulfonyl, $C_1$ to $C_{10}$ alkylsulfonyl, $C_1$ to $C_{10}$ substituted alkylsulfonyl, $C_1$ to $C_{12}$ alkylaminocarbonyl, $C_1$ to $C_{12}$ substituted alkylaminocarbonyl, phenylaminocarbonyl, and substituted phenylaminocarbonyl; and R$^{10}$ is selected from the group consisting of a hydrogen atom, $C_1$ to $C_{12}$ alkyl, $C_1$ to $C_{12}$ substituted alkyl, $C_2$ to $C_{12}$ alkenyl, $C_2$ to $C_{12}$ substituted alkenyl, $C_7$ to $C_{18}$ phenylalkyl, $C_7$ to $C_{18}$ substituted phenylalkyl, $C_1$ to $C_{12}$ heterocycloalkyl and $C_1$ to $C_{12}$ substituted heterocycloalkyl; or a pharmaceutically acceptable salt of a compound thereof.

* * * * *